Figure 1:
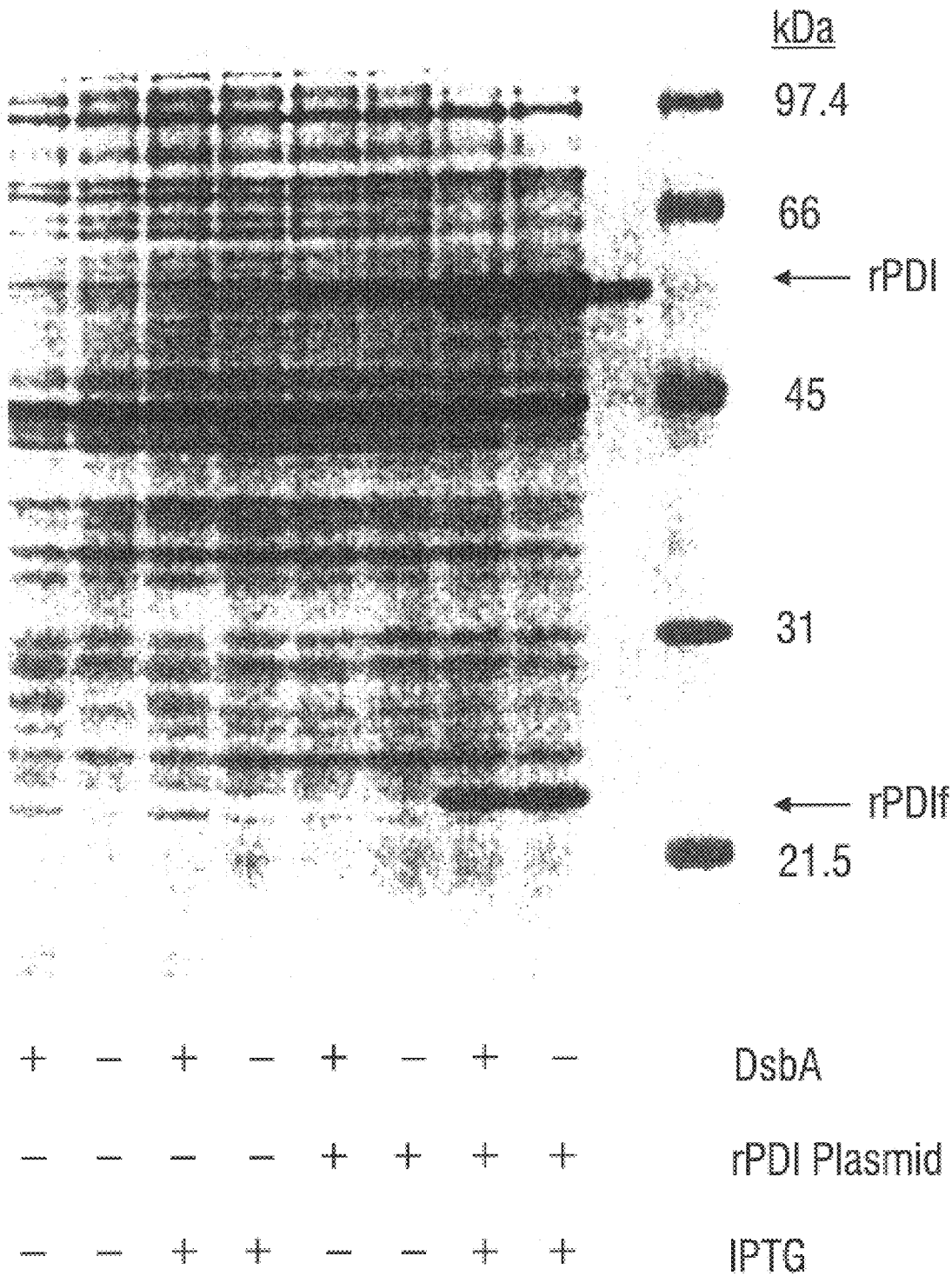

United States Patent [19]
Georgiou et al.

[11] Patent Number: 6,027,888
[45] Date of Patent: Feb. 22, 2000

[54] METHODS FOR PRODUCING SOLUBLE, BIOLOGICALLY-ACTIVE DISULFIDE-BOND CONTAINING EUKARYOTIC PROTEINS IN BACTERIAL CELLS

[75] Inventors: George Georgiou, Austin, Tex.; Marc Ostermeier, State College, Pa.

[73] Assignee: Board of Regents, The University of Texas System, Austin, Tex.

[21] Appl. No.: 08/834,516

[22] Filed: Apr. 4, 1997

Related U.S. Application Data

[60] Provisional application No. 60/014,950, Apr. 5, 1996.

[51] Int. Cl.⁷ .............................. C12Q 1/68; C12P 21/00; C12N 1/00; C07H 21/04
[52] U.S. Cl. ........................ 435/6; 435/69.1; 435/91.1; 435/243; 435/320.1; 530/350; 536/23.2; 536/23.5
[58] Field of Search .............................. 435/6, 69.1, 91.1, 435/243, 320.1; 530/350; 536/23.2, 23.5

[56] References Cited

U.S. PATENT DOCUMENTS

| | | | |
|---|---|---|---|
| 4,431,740 | 2/1984 | Bell et al. | 435/252.33 |
| 4,652,525 | 3/1987 | Rutter et al. | 435/252.33 |
| 4,661,453 | 4/1987 | Pollard | 435/212 |
| 5,077,392 | 12/1991 | Rudolph et al. | 530/387.1 |
| 5,139,939 | 8/1992 | Ohashi et al. | 435/70.1 |
| 5,223,256 | 6/1993 | Stern et al. | 424/94.63 |
| 5,223,408 | 6/1993 | Goeddel et al. | 435/69.3 |
| 5,270,181 | 12/1993 | McCoy et al. | 435/69.7 |
| 5,292,646 | 3/1994 | McCoy et al. | 435/69.7 |
| 5,304,472 | 4/1994 | Bass et al. | 435/69.1 |
| 5,336,602 | 8/1994 | Brinkmann et al. | 435/69.1 |
| 5,342,763 | 8/1994 | Swartz | 435/69.1 |
| 5,453,363 | 9/1995 | Rudolph et al. | 435/69.1 |
| 5,453,364 | 9/1995 | Paoletti | 435/69.3 |
| 5,486,471 | 1/1996 | Mulvihill et al. | 435/226 |
| 5,508,192 | 4/1996 | Georgiou et al. | 435/252.8 |
| 5,578,466 | 11/1996 | Hayano et al. | 435/69.7 |
| 5,616,486 | 4/1997 | Anderson et al. | 435/226 |

FOREIGN PATENT DOCUMENTS

| | | |
|---|---|---|
| 0 225 177 | 11/1986 | European Pat. Off. . |
| 0 278 355 | 2/1988 | European Pat. Off. . |
| 0 293793 | 5/1988 | European Pat. Off. . |
| 0 304311 | 8/1988 | European Pat. Off. . |
| 0 353 188 | 7/1989 | European Pat. Off. . |
| 0 356 965 | 8/1989 | European Pat. Off. . |
| 0 361 475 | 9/1989 | European Pat. Off. . |
| 0 368 342 | 11/1989 | European Pat. Off. . |
| 0 382 174 | 2/1990 | European Pat. Off. . |
| 0 400 545 | 5/1990 | European Pat. Off. . |
| 0 509841 | 4/1992 | European Pat. Off. . |
| 0 510 658 | 4/1992 | European Pat. Off. . |
| WO 87/03904 | 7/1987 | WIPO . |
| WO 87/04462 | 7/1987 | WIPO . |
| WO88/10307 | 12/1988 | WIPO 435/172.3 |
| WO 89/12681 | 12/1989 | WIPO . |
| WO 90/02174 | 3/1990 | WIPO . |
| WO 90/03388 | 4/1990 | WIPO . |
| WO 93/24635 | 12/1993 | WIPO . |
| WO 93/25676 | 12/1993 | WIPO . |
| WO 94/08012 | 4/1994 | WIPO . |
| WO 96/14422 | 5/1996 | WIPO . |

OTHER PUBLICATIONS

Orkin et al. Report and recomendations of the panel to assess the NIH investment in research on gene therapy, Dec. 7, 1995
Weatherall, D. J. Scope and limitations of gene therapy. British Medical Bulletin. vol. 51(1):1–11, Jan. 1995.
Verma et al. Gene therapy– promises, problems and prospects. Nature vol. 389:239–242, Sep. 18, 1997.
International Search Report dated Jul. 9, 1997 (UTFB:632P—).
Bardwell et al., "The bonds that tie: Catalyzed disulfide bond formation," *Cell*, 74:769–771, 1993.
Bardwell et al., "A pathway for disulfide bond formation in vivo," *Proc. Natl. Acad. Sci. USA*, 90:1038–1042, 1993.
Bardwell et al., "Identification of a protein required for disulfide bond formation in vivo," *Cell*, 67:581–589, 1991.
Bardwell, "Building bridges: Disulphide bond formation in the cell," *Mol. Microbiol.*, 14(2):199–205, 1994..
Bulleid, "Protein disulfide–isomerase: Role in biosynthesis of secretory proteins," *Adv. Prot. Chem.*, 44:125–150, 1993.
Cai et al., "Chaperone–like activity of protein disulfide isomerase in the refolding of a protein with no disulfide bonds," *J. Biol. Chem.*, 269(40):24550–24552, 1994.
Creighton et al., "Kinetic Role of a meta–stable native–like two–disulfide species in the folding transition of bovine pancreatic trypsin inhibitor," *J. Mol. Biol.*, 179:497–526, 1984.
Creighton et al., "On the biosynthesis of bovine pancreatic trypsin inhibitor (BPTI)," *J. Mol. Biol.*, 232:1176–1196, 1993.
Creighton, "Catalysis by protein–disulphide isomerase of the unfolding and refolding of proteins with disulphide bonds," *J. Mol. Biol.*, 142:43–62, 1980.
Dailey et al., "Mutants in disulfide bond formation that disrupt flagellar assembly in *Escherichia coli*," *Proc. Natl. Acad. Sci. USA*, 90:1043–1047, 1993.
Darby et al., "Dissecting the mechanism of protein disulfide isomerase: catalysis of disulfide bond formation in a model peptide," *Biochemistry*, 33:7937–7947, 1994.

(List continued on next page.)

*Primary Examiner*—David Guzo
*Assistant Examiner*—William Sandals
*Attorney, Agent, or Firm*—Arnold, White & Durkee

[57] ABSTRACT

Disclosed are methods of producing eukaryotic disulfide bond-containing polypeptides in bacterial hosts, and compositions resulting therefrom. Co-expression of a eukaryotic foldase and a disulfide bond-containing polypeptide in a bacterial host cell is demonstrated. In particular embodiments, the methods have been used to produce mammalian pancreatic trypsin inhibitor and tissue plasminogen activator (tPA) in soluble, biologically-active forms, which are isolatable from the bacterial periplasm. Also disclosed are expression systems, recombinant vectors, and transformed host cells.

40 Claims, 7 Drawing Sheets

OTHER PUBLICATIONS

De Sutter et al., "Production of enzymatically active rat protein disulfide isomerase in *Escherichia coli*," *Gene*, 141:163–170, 1994.

De Sutter et al., "Disulphide bridge formation in the periplasm of *Escherichia coli*: β–lactamase::human IgG3 hinge fusions as a model system," *Mol. Micro.*, 6(15):2201–2208, 1992.

Freedman et al., "Protein disulphide isomerase: Building bridges in protein folding," *TIBS*, 19:331–336, 1994.

Freedman et al., "Role of protein disulphide isomerase in the expression of native proteins," *Biochem. Soc. Symp.*, 55:167–192, 1994.

Fukuzono et al., Production of Biologically Active Mature Brain–derived Neurotrophic Factor in *escherichia coli*, Biosci. Biotech. Biochem., 59(9):1727–1731,1995.

Georgiou and Valax, "Expression of correctly folded proteins in *escherichia coli*," Current Opinion in Biotechnology, 7:190–197, 1996.

Goldenberg, "Native and non–native intermediates in the BPTI folding pathway," *TIBS*, 17:257–261, 1992.

Grauschopf et al., "Why is DsbA such an oxidizing disulfide catalyst?," *Cell*, 83:947–955, 1995.

Grunfeld et al., "Effector–assisted refolding of recombinant tissue–plasminogen activator produced in *Escherichia coli*," *Appl. Biochem. Biotechnol.*, 33:117–38, 1992.

Guilhot et al., "Evidence that the pathway of disulfide bond formation in *Escherichia coli* involves interactions between the cysteines of DsbB and DsbA," *Pro. Natl. Acad. Sci. USA*, 92:9895–9899, 1995.

Hockney, "Recent developments in heterologous protein production in *Escherichia coli*," *Trends Biotech.*, 12:456–463, 1994.

Hwang et al., "Oxidized Redox State of Glutathione in the Endoplasmic Reticulum," *Science*, 257:1496–1502, 1992.

Jander et al., "Two cysteines in each periplasmic domain of the membrane protein DsbB are required for its function in protein disulfide bond formation," *EMBO J.*, 13(21):5121–5127, 1994.

Joly and Swartz, "Protein Folding Activities of *Escherichia coli* Protein Disulfide Isomerase," *Biochemistry*, 33:4231–4236, 1994.

Kamitani et al., "Identification and characterization of an *Escherichia coli* gene required for the formation of correctly folded alkaline phosphatase, a periplasmic enzyme," *EMBO J.*, 11(1);57–62, 1992.

Kishigami et al., "Resox states of DsbA in the periplasm of *Escherichia coli*," FEBS Letters, 364:55–58, 1995.

Knappik et al., "The effect of folding catalysts on the in vivo folding process of different antibody fragments expressed in *Escherichia coli*," *Bio/Technology*, 11(1):77–83, 1993.

LaMantia et al., "The essential function of yeast protein disulfide isomerase does not reside in its isomerase activity," *Cell*, 74:899–908, 1993.

Lyles and Gilbert, "Mutations in the thioredoxin sites of protein disulfide isomerase reveal functional nonequivalence of the N– and C–terminal domains," *J. Biol. Chem.*, 269:30946–30952, 1994.

Marks et al., "Production of native, correctly folded bovine pancreatic trypsin inhibitor by *Escherichia coli*," *J. Biol. Chem.*, 261(16):7115–7118, 1986.

Martin et al., "Crystal structure of the DsbA protein required for disulphide bond formatin in vivo," *Nature*, 365:464–468, 1993.

McGrath et al., "The Sequence and Reactive Site of Ecotin," *J. Biol. Chem.*, 266(10):6620–6625, 1991.

Missiakas et al., "Identification and characterization of a new disulfide isomerase–like protein (DsbD) in *Escherichia coli*," *EMBO J.*, 14(14):3415–3424, 1995.

Missiakas et al., "Identification and characterization of the *Escherichia coli* gene dsbB, whose product is involved in the formation of disulfide bonds In vivo," *Proc. Natl. Acad. Sci. USA*, 90:7084–7088, 1993.

Missiakas et al., "The *Escherichia coli* dsbC (xprA) gene encodes a periplasmic protein involved in disulfide bond formation," *EMBO J.*, 13(8):2013–2020, 1994.

Nilsson et al., "Secretion incompetence of bovine pancreatic trypsin inhibitor expressed in *Escherichia coli*," *J. Biol. Chem.*, 266(5):2970–2977, 1991.

Noiva et al., "Protein Disulfide Isomerase," *J. Biol. Chem.*, 267(6):3553–3556, 1992.

Noiva et al., "Peptide binding by protein disulfide isomerase, a resident protein of the endoplasmic reticulum lumen," *J. Biol. Chem.*, 266(29):19645–19649, 1991.

Ostermeier et al., "The Folding of bovine pancreatic trypsin inhibitor in the *Escherichia coli* periplasm," *J. Biol. Chem.*, 269(33):21072–21077, 1994.

Ostermeier et al., "Eukaryotic protein disulfide isomerase complements *Escherichia coli* dsbA mutants and increases the yield of heterologous secreted protein with disulfide bonds," *J. Biol. Chem.*, 271(18):10616–10622, 1996.

Pollitt et al., "Role of primary structure and disulfide bond formation in β–lactamase secretion."*J. Bacteriol.*, 153(1):27–32, 1983.

Puig and Gilbert, "Anti–chaperone behavior of BiP during the protein disulfide isomerase–catalyzed refolding of reduced denatured lysozyme," *J. Biol. Chem.*, 269:25889–25896, 1994.

Puig et al., "Protein disulfide isomerase exhibits chaperone and anti–chaperone activity in the oxidative refolding of lysozyme," *J. Biol. Chem.*, 269(10):7746–7771, 1994.

Puig et al., "The role of the thiol/disulfide centers and peptide binding site in the chaperone and anti–chaperone activities of protein disulfide isomerase," *J. Biol. Chem.* 269:19128–19135, 1994.

Rijken and Groeneveld, "Isolation and Functional Characterization of the Heavy and Light Chains of Human Tissue–Type Plasminogen Activator," *J. Biol. Chem.*, 26(7):3098–3102, 1986.

Rudolph et al., "In vitro folding of inclusion body proteins," *FASEB J*, 10:49–56, 1996.

Shevchik et al., "Characterization of DsbC, a periplasmic protein of *Erwinia chrysanthemi* and *Escherichia coli* with disulfide isomerase activity," *EMBO J.*, 13(8):2007–2012, 1994.

Simmons et al., "Translational level is a critical factor for the secretion of heterologous proteins in *Escherichia coli*," *Nature Biotechnology*, 14:626–634, 1996.

van Mierlo et al., "Partially folded conformation of the (30–51) intermediate in the disulphide folding pathway of bovine pancreatic trypsin inhibitor," *J. Mol. Biol.*, 229:1125–1146, 1993.

Waldenström et al., "Synthesis and secretion of a fibrinolytically active–type plasminogen activator variant in *Escherichia coli*," *Gene*, 99:243–248, 1991.

Walker et al., "Effect of redox environment on the in vitro and in vivo folding of RTEM–1 β–Lactamase and *Escherichia coli* alkaline phosphatase," *J. Biol. Chem.*, 269(45):28487–28493, 1994.

Weissman et al. "Efficient catalysis of disulphide bond rearrangements by protein disulphide isomerase," *Nature*, 365:185–188, 1993.

Weissman et al. "Kinetic role of nonnative species in the folding of bovine pancreatic trypsin inhibitor," *Proc. Natl. Acad. Sci. USA*, 89:9900–9904, 1992.

Weissman et al. "Reexamination of the folding of BPTI: predominance of native intermediates," *Science*, 253:1386–1393, 1991.

Wittrup, Disulfide Bond Formation and Eukaryotic Secretory Productivity, Current Opinion in Biotechnology, 6:203–208, 1995.

Wülfing et al., "Correctly folded T–cell receptor fragments in the periplasm of *Escherichia coli*," *J. Mol. Biol.*, 242:655–669, 1994.

Wülfing et al., "Protein folding in the periplasm of *Escherichia coli*," *Mol. Microbiol.*, 12(5):685–692, 1994.

Wunderlich et al., "Bacterial protein disulfide isomerase: efficient catalysis of oxidative protein folding at acidic pH," *Biochemistry*, 32:12251–12256, 1993.

Wunderlich et al., "Redox properties of protein disulfide isomerase (DsbA) from *Escherichia coli*," *Protein Sci.*, 2:717–726, 1993.

Wunderlich et al., "In vivo control of redox potential during protein folding catalyzed by bacterial protein disulfide–isomerase (DsbA)," *J. Biol. Chem.*, 268(33):24547–24550, 1993.

Zapun et al., "Effects of DsbA on the disulfide folding of bovine pancreatic trypsin inhibitor and α–Lactalbumin," *Biochemistry*, 33:5202–5211, 1994.

Zapun et al., "Folding in vitro of bovine pancreatic trypsin inhibitor in the presence of proteins of the endoplasmic reticulum," *Proteins: Structure, Function, and Genetics*, 14:10–15, 1992.

Zapun et al., "Replacement of the active–site cysteine residues of DsbA, a protein required for disulfide bond formation in vivo," *Biochemistry*, 33:1907–1914, 1994.

Zapun et al., "The reactive and destabilizing disulfide bond of DsbA, a protein required for protein disulfide bond formation in vivo," *Biochemistry*, 32:5083–5092, 1993.

METHODS FOR PRODUCING SOLUBLE, BIOLOGICALLY-ACTIVE DISULFIDE-BOND CONTAINING EUKARYOTIC PROTEINS IN BACTERIAL CELLS

The present application is a continuing application based on U.S. Provisional patent application Ser. No. 60/014,950, filed Apr. 5, 1996, the entire content of which is specifically incorporated herein by reference.

The United States government has certain rights in the present invention pursuant to Grant 1R01-GM47520-01A1 from the National Institutes of Health.

BACKGROUND OF THE INVENTION

1.1 Field of the Invention

The present invention relates generally to the field of molecular biology. More particularly, certain embodiments concern methods and compositions related to improved methods of producing biologically-active, soluble eukaryotic disulfide bond-containing eukaryotic polypeptides in bacterial cells. In preferred embodiments, disulfide-bond containing eukaryotic fusion proteins such as tissue plasminogen activator (tPA) and pancreatic trypsin inhibitor (PTI) are produced in recombinant transformed *Escherichia coli* cells using recombinant vector systems which direct the co-expression of the eukaryotic protein and a eukaryotic foldase, such as protein disulfide isomerase (PDI).

1.2 Description of the Related Art

1.2.1 PROTEIN EXPRESSION IN BACTERIAL HOSTS

A significant achievement in molecular biology has been the use of recombinant bacterial cells to produce eukaryotic proteins. This method has been particularly useful for production of medically important polypeptides that are obtained in low yield from natural sources. Often otherwise difficult to obtain in quantity, such proteins are "overexpressed" in the host cell and subsequently isolated and purified. Preinsulin for example may be produced in a recombinant prokaryotic microorganism carrying DNA encoding rat preinsulin (U.S. Pat. Nos. 4,431,740 and 4,652,525, specifically incorporated herein by reference).

Expression of multiple disulfide bond-containing eukaryotic polypeptides, and particularly mammalian proteins, in bacterial cells has frequently produced disappointing and unsatisfactory results because conditions and environment in the host cells were not conducive to correct folding. Disulfide bond formation is a process mainly restricted to proteins outside the cytoplasmic compartment such as those secreted into the lumen of the endoplasmic reticulum (ER) or the periplasm of gram negative bacteria. Correct folding may depend on the formation of cysteine-cysteine linkages and subsequent stabilization of the protein into an enzymatically active structure. However, the cytoplasm is in fact a reducing environment due to the presence of thioredoxin reductase or reduced glutathione, thus blocking oxidation so that disulfide bonds do not form. The endoplasmic reticulum (ER) apparently is more conducive to oxidation due to the presence of oxygen or oxidized glutathione.

Recent studies indicate that disulfide bond formation in vivo is a catalyzed process, whether in the ER or periplasm. In *E. coli*, a pathway for the formation of disulfide bonds in secreted proteins has been described, involving two proteins, DsbA and DsbB (Bardwell et al., 1993; Missiakas et al., 1993).

A role for these Dsb proteins is supported by the observation that mutants of *E. coli* that lack DsbA or DsbB are defective with respect to disulfide bond formation (Dailey and Berg, 1993). In the yeast *Saccharomyces cerevisiae*, a similar defect is found in certain mutants defective in protein disulfide isomerase (PDI) gene. Disulfide bond formation in carboxypeptidase Y in these mutants is impaired.

1.2.2 EXPRESSION OF EUKARYOTIC PROTEINS IN BACTERIAL HOSTS

It is known that disulfide bonds are critical in some proteins in order for proper folding and even in transport and secretion. Yet many proteins cannot be efficiently expressed in bacterial hosts due to failure of disulfide bond formation. Cytoplasmic expression systems in bacteria are not conducive to disulfide bond formation because of a reducing environment. The presence of proteases in the cytoplasm may cause rapid degradation of the protein, resulting in low yields.

Most exported proteins contain disulfide bonds which confer increased thermodynamic stability to the folded polypeptide chain. The sequence of events involved in cysteine oxidation and correct pairing to form native disulfide bonds is a critical step in protein folding. Due to constraints related to the reactivity or structural accessibility of cysteine thiols in proteins, disulfide bonds often form very slowly. A complex cellular machinery, whose components and mode of action are only now beginning to be understood, has evolved to catalyze these processes in vivo. In Gram-negative bacteria such as *E. coli*, the cytoplasm is highly reducing and therefore disulfide formation normally occurs after a polypeptide chain has been translocated across the inner membrane (Wülfing and Plückthun, 1994; Bardwell, 1994). Genetic analysis has identified at least six genes coding for cell envelope proteins that play a role in disulfide bond formation. Four of these proteins have been characterized in some detail (Bardwell, 1994; Missiakas et al., 1995). DsbA is a 21.5 kDa enzyme having a thioredoxin-like subdomain with an extremely reactive and highly oxidizing disulfide bond but poor disulfide isomerization activity (Bardwell et al., 1991; Kamitani et al., 1992; Zapun et al., 1993; Wunderlich and Glockshuber, 1993a; 1993b; Joly and Swartz, 1994). DsbB is a cytoplasmic membrane protein which is required for the reoxidation of DsbA (Guilhot et al., 1995; Bardwell et al., 1993; Missiakas et al., 1993; Dailey and Berg, 1993). DsbC is another soluble cysteine oxidoreductase and has much higher disulfide isomerase activity than DsbA (Bardwell, 1994; Missiakas et al., 1994). Finally, the recently discovered DsbD is an inner membrane protein which has been proposed to function as a reducing source in the periplasm and to be required for maintaining proper redox conditions (Missiakas et al., 1995).

Bacterial proteins become oxidized and fold rapidly soon after export from the cytoplasm. However, the formation of native disulfide bonds in heterologous proteins with multiple cysteines is often very inefficient (Wunderlich and Glockshuber, 1993a; 1993b; De Sutter et al., 1992). Partially folded molecules are highly susceptible to degradation, thus resulting in very low yields (Wülfing and Plückthun, 1994). The shortcomings of the disulfide bond formation machinery of *E. coli* with respect to eukaryotic proteins have been illuminated by analyzing the folding pathway of the Bovine PTI (BPTI) expressed in the periplasmic space (Ostermeier and Georgiou, 1994). BPTI is a 6.5-kDa protease inhibitor with three disulfide bonds. In *E. coli*, just as in vitro, the rate limiting step in folding is the isomerization of two disulfide intermediates. The bacterial periplasmic space is thought to be strongly oxidizing (Wunderlich and Glockshuber, 1993a; 1993b; Walker and Gilbert, 1994; Kishigami et al., 1995) and appears to lack sufficient disulfide isomerase activity required for the folding of heterologous multi-disulfide proteins. In sharp contrast to the bacterial periplasm, disulfide bond formation in eukaryotes occurs in the endoplasmic reticulum, a compartment which is maintained at relatively reducing conditions (Hwang et al., 1992). Disulfide bond formation and isomerization in the ER is catalyzed by PDI, an abundant 55-kDa enzyme which apart from its thioredoxin-like active site shares little homology with prokaryotic proteins. PDI contains two active sites that are not functionally equivalent, has been shown to both promote and inhibit protein aggregation, and can exist in different oligomerization states (Freedman et al., 1994; Lyles and Gilbert, 1994; Puig and Gilbert, 1994; Puig et al., 1994).

1.2.3 CURRENT METHODS OF PRODUCING EUKARYOTIC PROTEINS ARE INEFFICIENT

Expression enhancers for increasing yield of eukaryotic proteins expressed in *E. coli* cells have been reported (U.S. Pat. No. 5,336,602). The expression enhancer is simultaneously expressed with a protein of interest where the rate of expression is shown to increase by comparison with expression of the protein of interest in the absence of an enhancer. However, while yield is increased over expression when enhancer is not present, there are no indications that either correct folding is achieved or that full activity is obtained.

Eur. Pat. Appl. No. EP 510,658 describes an improvement of the yield of secreted disulfide-bonded proteins in bacterial cell by providing a simultaneous expression of a recombinant vector encoding the prokaryotic protein disulfide isomerase of *E. coli* and the addition of thiol reagents to the culture medium to promote correct folding of the secreted polypeptide of interest. Unfortunately, the method produced negligible secreted protein unless sufficient thiol reagent was added to the culture medium, and if too much thiol reagent was present, cells were killed and the total protein isolated declined dramatically.

tPA is one example of a pharmaceutically-important drug produced by recombinant methods. Unfortunately the current methods for producing tPA from bacterial cell culture are both costly and laborious. One such method for the production of tPA in heterologous host organisms relies on the production of inactive tPA intracellularly in inclusion bodies, and the subsequent isolation and purification of such inclusion bodies, followed by activation of the tPA once freed from the inclusion bodies. U.S. Pat. No. 5,077,392 discloses a renaturation method for refolding denatured proteins obtained after expression in inclusion bodies. tPA was isolated as a denatured reduced protein and on subsequent oxidation refolded under oxidizing conditions to obtain what was reported as up to a 26% yield of "reactivated" protein. While the method appeared to improve polypeptide yield, the process involves multiple, time-consuming steps, due to the initial recovery of the insoluble, inactive protein.

Other methods of producing tPA have employed eukaryotic cell culture methods, which are also expensive and time-consuming. Mammalian cells have been used in attempts to improve production of highly active polypeptides such as tPA. U.S. Pat. No. 4,661,453 discloses production of tPA in substantial quantities in rat prostate adenocarcinoma cells. The tPA isolated from the cell culture medium shows tPA activity, however the method is quite expensive since the mammalian cells have an origin in spontaneous adenocarcinoma cancer cells, and must be selected for the ability to produce tPA. The method has not been shown to be feasible for commercial production of proteins such as tPA on an economic scale. Even methods involving the production of tPA in recombinant chinese hamster ovary (CHO) cells, result in a cost-per-unit-dose of approximately $1200 in the current pharmaceutical market.

1.2.4 DEFICIENCIES IN THE PRIOR ART

Currently there is a lack of efficient methods of producing complex eukaryotic proteins with multiple disulfide bonds on an economic scale. Likewise, there is a need to develop methods which produce proteins that are correctly folded and active without the need for reactivation or subsequent processing once isolated from a host cell.

Therefore, what is lacking in the prior art are methods, recombinant vectors, host cells, and compositions comprising high-level expression of eukaryotic disulfide bond-containing polypeptides (such as tPA and BPTI) which are soluble, correctly-folded, active, and readily isolatable from cell extracts of prokaryotic hosts.

2. SUMMARY OF THE INVENTION

The present invention overcomes one or more of these and other drawbacks inherent in the prior art by providing novel methods, recombinant host cells, vectors and compositions resulting therefrom for efficiently producing eukaryotic polypeptides containing disulfide bonds in bacterial host cells which are active, correctly folded, and secreted from the bacterial cell to provide economic and convenient means for the recovery, isolation, and purification of the recombinant polypeptide of interest. The present invention represents a significant breakthrough in the fields of molecular biology, protein chemistry, and pharmaceutics, in producing eukaryotic recombinant polypeptides in prokaryotic hosts through novel methods and recombinant vectors which direct the coexpression of eukaryotic polypeptides of interest with a eukaryotic foldase such as protein disulfide isomerase. Recovery of correctly folded, active, soluble recombinant polypeptides in significant quantity is now possible by employing the disclosed methods and compositions.

In one embodiment, the present invention provides a process for producing in a bacterial cell, a biologically-active, soluble eukaryotic polypeptide having at least about three disulfide bonds. The process generally involves expressing in the cell a first DNA segment encoding a disulfide isomerase operably linked to a signal sequence and a second DNA segment encoding a eukaryotic polypeptide operably linked to a signal sequence under conditions effective to produce the eukaryotic polypeptide. Preferably, the polypeptide is a mammalian polypeptide, with human and bovine polypeptides being particularly preferred. In important embodiments, the eukaryotic polypeptide is a tissue plasminogen activator or pancreatic trypsin inhibitor, and the disulfide isomerase is protein disulfide isomerase isolated from rat, yeast, or human origin.

The eukaryotic polypeptide to be produced in the bacterial host will preferably comprise at least about three, four or five disulfide bonds. Or more preferably, about six, seven, eight, or nine disulfide bonds. Or still more preferably, at least about ten, eleven, twelve, thirteen, fourteen, fifteen, sixteen, or seventeen disulfide bonds. When the eukaryotic polypeptide is tPA, the peptide preferably comprises at least about seventeen disulfide bonds.

The signal sequence is preferably selected from the group consisting of OmpA, LamB, StII, MalE, Lpp, and PelB, with OmpA and StII sequences be particularly preferred. Preferred promoters for the expression of the two DNA segments are selected from the group consisting of lac-lpp, lpp, trc, tac, T7, $P_{BAD}$, phoA and $\lambda_{PL}$, with lac-lpp promoters being particular useful in the practice of the invention. Plasmids such as pLPPsOmpArPDI are preferred for the expression of the disulfide isomerase, and plasmids such as pTPA177 or pACYCBPTI are particularly desirable for expression of the eukaryotic polypeptides of interest.

The bacterial cell may be cultured in a medium comprising one or more reducing agents selected from the group consisting of glutathione, cysteine, cystamine, thioglycollate, dithiothreitol and dithioerythritol, and preferably, the bacterial cell is an Enterobacteriaceae cell such as Escherichia or Salmonella spp. cells. Highly preferred cells are E. coli ATCC 98380, SF103, SF110, UT5600 and RB7911 cells. ATCC 98380 was deposited on Mar. 28, 1997 with the American Type Culture Collection, 12301 Parklawn Drive, Rockville, Md. 20852 in accordance with U.S. Patent and Trademark Office requirements for microorganism deposits. The deposit has been made in accordance with the terms of the Budapest Treaty on the international recognition of the deposit of microorganisms for the purposes of patent procedure. In accordance with the terms of the Budapest Treaty: (a) the deposit will be made accessible to the Commissioner upon request during the pendency of this application; (b) all restrictions to access by the public of this deposit will be irrevocably removed upon granting of the patent; (c) this deposit will be maintained in the public depository for a period of thirty years or five years after the last request, or for the effective life of the patent, whichever is longer; and, (d) this deposit will be replaced if it should ever become non-viable.

An important aspect of the invention is the production in bacterial cells of soluble, biologically-active eukaryotic polypeptides. In important embodiments, the soluble protein is secreted to the periplasm or to the outer membrane of the bacterial cell, and the polypeptide is isolatable from a culture supernatant or a soluble fraction of the bacterial cell. Preferably, the eukaryotic polypeptide produced in the bacterial host assumes a conformation substantially identical to the conformation assumed by the polypeptide when produced in a eukaryotic host cell. Preferably, the eukaryotic polypeptide produced in the bacterial cell has a specific activity equal to or greater than the specific activity of the polypeptide when produced in a eukaryotic host cell. When the eukaryotic polypeptide is a tissue plasminogen activator protein, a specific activity of at least about 5 to about 12 $\mu g/l/OD_{600\ nm}$ of culture is obtained. This corresponds to a specific activity of approximately 2000 to 48000 $IU/l/OD_{600\ nm}$. When the eukaryotic polypeptide is a pancreatic trypsin-inhibitor protein, a specific activity of about 10 $\mu g/mg$ of total cell protein is obtained.

A further aspect of the invention is an expression system for producing in a bacterial cell, a biologically-active, soluble eukaryotic polypeptide. The expression system generally comprises a first DNA segment and a second DNA segment, with the first segment encoding a disulfide isomerase and the second segment encoding a eukaryotic polypeptide having at least about three disulfide bonds. As stated above, the protein produced is preferably a disulfide-bond containing polypeptide such as tissue plasminogen activator or pancreatic trypsin inhibitor, and the disulfide isomerase is preferably a rat, yeast, or human PDI. The DNA segments preferably further comprise a signal sequence such as OmpA, LamB, StII, MalE, Lpp, or PelB, and are expressed by a promoter such as lac-lpp, ara, lac, lpp, trc, tac, T7, $P_{BAD}$, phoA or $\lambda_{PL}$. Preferred examples of the expression system include pLPPsOmpArPDI co-expressed in a bacterial cell with either pTPA177 or pACYCBPTI. The bacterial cell may be cultured in a medium comprising one or more reducing agents selected from the group consisting of glutathione, cysteine, cystamine, thioglycollate, dithiothreitol and dithioerythritol, and preferably, the bacterial cell is an Enterobacteriaceae cell such as Escherichia or Salmonella spp. cells. Highly preferred cells are E. coli ATCC 98380, SF103, SF110, UT5600 and RB7911 cells.

Preferably the eukaryotic polypeptide expressed by this system has a specific activity of at least about 1 to about 1000 $\mu g/l/OD_{600\ nm}$ of culture, or more preferably, about 5 to about 500 $\mu g/l/OD_{600\ nm}$ of culture, or more preferably, about 10 to about 100 $\mu g/l/OD_{600\ nm}$ of culture, with specific activities in the range of at least about 5 to about 12 $\mu g/l/OD_{600\ nm}$ units of culture being highly preferred.

The expression system may comprise a single recombinant vector which expresses both the disulfide isomerase-encoding DNA segment and the polypeptide of interest-encoding second DNA segment. Alternatively, the expression system may comprise two or more distinct plasmids one of which expresses the first DNA segment and a second of which expresses the second DNA segment. In the case of the latter arrangement, it is preferably that both vectors are capable of replication and expression in a single bacterial cell. An example of such as system is a bacterial cell comprising the vector pLPPsOmpArPDI in combination with a second vector such as pACYCBPTI or pTPA177.

A further aspect of the invention is a recombinant vector comprising a first transcriptional unit encoding a mammalian protein disulfide isomerase operably linked to a first signal sequence and a second transcriptional unit comprising a DNA segment encoding a mammalian polypeptide having at least about three disulfide bonds operably linked to a second signal sequence.

As stated above, the protein produced is preferably a disulfide-bond containing polypeptide such as tissue plasminogen activator or pancreatic trypsin inhibitor, and the disulfide isomerase is preferably a rat, yeast, or human PDI. The DNA segments preferably further comprise a signal sequence such as OmpA, LamB, StII, MalE, Lpp, or PelB, and are expressed by a promoter such as lac-lpp, ara, lac, lpp, trc, tac, T7, $P_{BAD}$, phoA or $\lambda_{PL}$. Preferred examples of the recombinant vectors include pLPPsOmpArPDI, pTPA177 and pACYCBPTI. The vectors are preferably introduced and maintained in a bacterial cell which may be cultured in a medium comprising one or more reducing agents selected from the group consisting of glutathione, cysteine, cystamine, thioglycollate, dithiothreitol and dithioerythritol, and preferably, the bacterial cell is an Enterobacteriaceae cell such as Escherichia or Salmonella spp. cells. Highly preferred cells are E. coli ATCC 98380, SF103, SF110, UT5600 and RB7911 cells.

As such, a recombinant host cell transformed with an expression system or vector described above is a further embodiment of the invention. Preferred examples of the recombinant host cell include ATCC 98380, and SF103, SF110, UT5600 or RB7911 cells transformed with the recombinant vector pLPPsOmpArPDI as well as either of plasmids pTPA177 or pACYCBPTI.

A further aspect of the invention is a composition comprising a biologically-active, soluble, recombinant tissue plasminogen activator protein or peptide operably linked to a bacterial export signal peptide. Preferably the tissue plasminogen activator is a mammalian tissue plasminogen activator such as human tPA. In particular aspects, the composition comprises a bacterial export signal peptide selected from the group consisting of OmpA, LamB, StII, MalE, Lpp, and PelB. In preferred embodiments, the tPA is encoded by a DNA segment positioned under the control of a promoter selected from the group consisting of lac-lpp, lpp, trc, tac, T7, $P_{BAD}$, phoA and $\lambda_{PL}$.

Preferably the tPA composition has a specific activity of at least about 1 to about 1000 µg/l/OD$_{600\ nm}$ of culture, or more preferably, about 5 to about 500 µg/l/OD$_{600\ nm}$ of culture, or more preferably, about 10 to about 100 µg/l/OD$_{600\ nm}$ of culture, with specific activities in the range of at least about 5 to about 12 µg/l/OD$_{600\ nm}$ units of culture being highly preferred.

A further aspect of the invention is a composition comprising a biologically-active, soluble, recombinant pancreatic trypsin inhibitor protein or peptide operably linked to a bacterial export signal peptide. Preferably the pancreatic trypsin inhibitor protein is a mammalian pancreatic trypsin inhibitor protein such as human or bovine PTI. In particular aspects, the composition comprises a bacterial export signal peptide selected from the group consisting of OmpA, LamB, StII, MalE, Lpp, and PelB. In preferred embodiments, the PTI is encoded by a DNA segment positioned under the control of a promoter selected from the group consisting of lac-lpp, lpp, trc, tac, T7, $P_{BAD}$, phoA and $\lambda_{PL}$.

Preferably the PTI composition has a specific activity of at least about 1 to about 1000 µg/l/OD$_{600\ nm}$ of culture, or more preferably, about 5 to about 500 µg/l/OD$_{600\ nm}$ of culture, or more preferably, about 10 to about 100 µg/l/OD$_{600\ nm}$ of culture, with specific activities in the range of at least about 5 to about 12 µg/l/OD$_{600\ nm}$ units of culture being highly preferred.

These and other embodiments of the invention are further understood in light of the teaching herein.

2.1 METHODS FOR PRODUCING EUKARYOTIC POLYPEPTIDES IN BACTERIAL CELLS

The present invention discloses methods for producing recombinant multi-disulfide polypeptides such as PTI, tPA, antibody fragments, protease inhibitors, therapeutic enzymes, lymphokines, neurotrophic factors, and related polypeptides and derivatives, mutants, and fusion proteins derived therefrom. One of the problems with tPA isolated from natural sources is low yields and extensive purification processes. The present invention in an important embodiment illustrates a strategy for overproducing tPA from a bacterial host, employing DNA constructs encoding human tPA and rat PDI to transform Gram-negative bacterial cells and coexpress the two proteins to produce active, soluble, secreted recombinant tPA polypeptides in vivo. In addition to the production of the complete tPA molecule, derivatives of tPA lacking the finger-like region, one or both of the kringle sub-domains or the epidermal growth factor subdomain may also be expressed in functional form. Such mutants as well as mutated tPA molecules with amino acid substitutions that affect the proteolytic activity exhibit useful pharmacological and/or pharmacokinetic properties, and are all contemplated to fall within the scope of the present invention.

An important aspect of the invention concerns methods for producing a biologically-active, recombinant eukaryotic polypeptide that contains multiple disulfide bonds. The method involves co-expressing in a suitable prokaryotic cell, such as a bacterial cell, a DNA segment encoding a prokaryotic signal sequence-eukaryotic disulfide isomerase fusion protein and a DNA segment encoding a prokaryotic signal sequence-eukaryotic recombinant polypeptide fusion protein under suitable physiological conditions to produce the recombinant eukaryotic fusion protein of interest. It is contemplated that the fusion protein of interest may be any eukaryotic protein for which expression in a prokaryotic host is desirable, but in particular, eukaryotic proteins which contain two or more disulfide bonds, and preferably those which contain at least three or four disulfide bonds or more.

Such preferred recombinant polypeptides include mammalian tissue plasminogen activator, mammalian pancreatic trypsin inhibitor, antibody fragments, insulin, protease inhibitors, therapeutic enzymes, lymphokines, cytokines, growth factors, neurotrophic factors and the like. The polypeptides may be native or mutated polypeptides, and preferred sources for such mammalian polypeptides include human, bovine, equine, porcine, lupine, and rodent sources, with human proteins being particularly preferred. The disulfide isomerase may be any such eukaryotic foldase which is capable of isomerizing disulfide bonds in a prokaryotic host. One such isomerase which is particularly preferred is mammalian protein disulfide isomerase. Most preferably, rat, human, bovine or porcine protein disulfide isomerases are contemplated to be useful in the practice of the invention.

The signal sequence employed in the practice of the invention may be any such sequence which encodes a signal capable of directing the export of the fusion protein to the bacterial periplasm or outer membrane, or alternatively into the culture supernatant in which such cells are grown. Typically, the signal sequence, or leader peptide, may be any of those well-known to those of skill in the art to be capable of directing the export of proteins in vivo in bacterial cells. A particularly preferred sequence is the *E. coli* alkaline phosphatase OmpA signal sequence, but equally preferred signal sequences include the Lpp, LamB, MalE, PelB or StII signal sequences and the like.

2.2 EXPRESSION SYSTEMS FOR PRODUCING EUKARYOTIC POLYPEPTIDES IN BACTERIA

In another preferred embodiment, the invention concerns an expression system that expresses both a disulfide isomerase such as one of the disulfide isomerases described herein, and an eukaryotic recombinant polypeptide of interest. The expression system has been used to produce recombinant OmpA-tPA and OmpA-BPTI when the OmpA-PDI polypeptide was coexpressed in the same recombinant host cells. The expression system is useful in the expression of recombinant polypeptides which have multiple disulfide bonds, even up to and including those with fourteen disulfide bonds.

The expression system in a general sense is composed of two expression units: one containing a DNA segment which encodes the disulfide isomerase fusion protein, and a second unit containing a DNA segment which encodes the recombinant fusion protein of interest. As described above, the two expression units may either be contained on a single recombinant vector, or alternatively, may be contained on two separate and distinct recombinant vectors. In the case of the latter, any two recombinant vectors may be utilized so long as the replicons are compatible in the same host cell and that the expression unit of each vector functions in the same cell to permit the co-expression of the two expression units. For example, the inventors contemplate the coexpression of pLPPsOmpArPDI and pACYCBPTI to be particularly useful in the production of BPTI from bacterial host cells, and the coexpression of pLPPsOmpArPDI and pTPA177 to be particularly useful in the production of tPA from bacterial host cells.

Expression of the fusion proteins may be promoted by any of a number of suitable promoter sequences which are well-known to promote the transcription of genes and/or operons in bacterial cells. In preferred embodiments, the DNA segments of the present invention are expressed from a lac-lpp, tac, ara, lac, trc, PhoA $P_{BAD}$, $\lambda_{PL}$, lpp, or T7 promoter. The components of the expression system described herein may be located on separate recombinant vectors with each transcriptional unit under the control of its own promoter, or alternatively, the components of the expression system may be located within a single recombinant vector. In the latter case, the disulfide isomerase-encoding transcriptional unit may be controlled by one promoter, while the recombinant disulfide bond-containing polypeptide-encoding transcriptional unit may be controlled by a separate promoter, or alternatively, the two transcriptional units may be in the form of a "tandem" transcriptional unit with both being controlled by a single promoter located 5' of both coding regions. The inventors have found the lac-lpp promoter to be particularly useful in the practice of the present invention.

Once a suitable (full length if desired) clone or clones have been obtained, whether they be CDNA based or genomic, one may proceed to prepare an expression system for the recombinant preparation of the eukaryotic polypeptides of the present invention. The engineering of DNA segment(s) for expression in a prokaryotic or eukaryotic system may be performed by techniques generally known to those of skill in recombinant expression. It is believed that expression in bacterial hosts, and *E. coli* in particular, will be preferred in the expression of high levels of correctly folded, active, soluble disulfide bond-containing eukaryotic polypeptides.

The cDNAs for such foldases and disulfide-containing proteins of interest may be separately expressed in bacterial systems, with the encoded proteins being expressed as fusions with β-galactosidase, ubiquitin, *Schistosoma japonicum* glutathione S-transferase, and the like. It is believed that bacterial expression using the methods described will ultimately have advantages over present prokaryotic expression systems which produce limited quantities of the proteins of interest intracellularly, inactive, in the form of inclusion bodies. This is particularly true for preparations of recombinant tPA.

It is proposed that transformation of host cells with DNA segments encoding the foldase (such as PDI) and the protein of interest will provide a convenient means for obtaining high levels of active secreted polypeptide. However, separate expression followed by reconstitution or reactivation of the protein once secreted is also certainly within the scope of the invention. For example, the inventors contemplate that the extracellular addition of thiol reagents such as glutathione will be useful in enhancing the recovery of certain proteins in large quantity using the methods described herein. Both cDNA and genomic sequences are suitable for expression, as the host cell will, of course, process the genomic transcripts to yield functional mRNA for translation into protein.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

In accordance with the general guidelines described above, a preferred method for expressing human tPA DNA has been found to be the transformation of *E. coli* SF103 cells with the expression vectors termed pTPA177 and pLPPsOmpArPDI. The pTPA177 expression vector is constructed from pACYC184, and contains the OmpA leader-tPA gene fusion.

Likewise, a preferred method for expressing bovine PTI DNA has been found to be the transformation of *E. coli* SF103 cells with the expression vectors termed pACYCBPTI and pLPPsOmpArPDI. The pACYCBPTI expression vector is constructed from pACYC184, and contains the OmpA leader-BPTI gene fusion.

pLPPsOmpArPDI contains the gene for the mature rat PDI fused to the OmpA signal sequence under the control of the lpp-lac promoter.

Preferred expression systems for the production of recombinant proteins may be contained either on a single plasmid vector containing the isomerase and disulfide.

It is contemplated that the recombinant polypeptides of the invention may be "overexpressed", i.e., expressed in increased levels relative to its natural expression in eukaryotic cells, or even relative to the expression of other proteins in the recombinant prokaryotic host cells. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in native cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding the foldase along with a gene encoding a disulfide bond-containing polypeptide of interest (e.g., tPA or BPTI) have been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The inventors have noticed that the level of expression from the introduced gene(s) of interest can vary in different clones, probably as a function of the particular recombinant gene construct used. Thus, the level of expression of a particular recombinant gene can be chosen by evaluating different clones derived from each transformation study; once that line is chosen, the constitutive promoter ensures that the desired level of expression is permanently maintained.

2.3 RECOMBINANT VECTORS FOR EXPRESSING EUKARYOTIC POLYPEPTIDES IN BACTERIA

In a related embodiment, the invention discloses a recombinant vector comprising a first transcriptional unit encoding a mammalian protein disulfide isomerase operatively linked to a signal sequence and a second transcriptional unit comprising a DNA segment encoding a mammalian tissue plasminogen activator or a mammalian pancreatic trypsin inhibitor.

A preferred plasmid for the expression of a protein disulfide isomerase transcriptional unit is pLPPsOmpArPDI.

A preferred plasmid for cloning the eukaryotic "target" polypeptide-encoding DNA fragment is pACYC184, although any other vector which may be maintained in the bacterial host and is compatible with the PDI-encoding expression vector may also be used. In particular, pACYC184 was used to create pACYCBPTI and pTPA177 which contain DNA sequences encoding bovine pancreatic trypsin inhibitor and human tissue plasminogen activator, respectively.

2.4 RECOMBINANT HOST CELLS

In particular, the invention provides recombinant Gram-negative host cells, preferably *E. coli* or Salmonella spp., transformed with nucleic acid segments encoding eukaryotic disulfide bond-containing polypeptides and an eukaryotic foldase from which the correctly-folded, active disulfide bond-containing polypeptide may be isolated. In sharp contrast to native un-engineered host cells, these transformed host cells have the ability to catalyze the formation and isomerization of disulfide bonds in eukaryotic proteins. Wild-type unengineered bacteria cannot normally form the correct folded structure of these proteins due to an inability to isomerize disulfide bonds in eukaryotic proteins.

The foldase is preferably a disulfide isomerase, and more preferably a protein disulfide isomerase. Such PDIs may be isolated from mammalian cells, plant cells, mycelial fungi, or yeast cells. Eukaryotic foldases such as the yeast Eug1 and its homologs are also contemplated to be useful in the practice of the present invention. Particularly preferred eukaryotic PDIs are obtained from mammalian or yeast sources. Exemplary mammalian sources for the foldases include human, bovine, rodent, porcine, equine, and lupine mammals. Exemplary yeast sources for the foldases include Saccharomyces spp. Pichia spp. (in particular Pichia pastoris) and Candida spp.

Prokaryotic hosts are preferred for expression of the proteins of the present invention. Some examples of prokaryotic hosts are *E. coli* strain SF103, RR1, LE392, B, $\lambda^{1776}$ (ATCC 31537) as well as *E. coli* W3110 (F$^-$, $\lambda^-$, prototrophic, ATCC 273325). Enterobacteriaceae species such as *Salmonella typhimurium* and *Serratia marcescens*, and various Pseudomonas species may also be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species (Bolivar et al., 1977), or pACYC184 as described above. pBR322 contains genes for ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins.

In addition, phage vectors containing replicon and control sequences that are compatible with the host microorganism can be used as transforming vectors in connection with these hosts. For example, bacteriophage such as λGEM™–11 may be utilized in making a recombinant vector which can be used to transform susceptible host cells such as *E. coli* LE392.

Those promoters most commonly used in recombinant DNA construction include the β-lactamase (penicillinase) and lactose promoter systems (Chang et al., 1978; Itakura et al., 1977; Goeddel et al., 1979) or the tryptophan (trp) promoter system (Goeddel et al., 1980). While these are the most commonly used, other microbial promoters have been discovered and utilized, and details concerning their nucleotide sequences have been published, enabling a skilled worker to ligate them functionally with plasmid vectors.

In addition to prokaryotes, eukaryotic microbes, such as yeast cultures may also be employed in various aspects of the present invention. *Saccharomyces cerevisiae*, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpL gene which provides a selection marker for a mutant strain of yeast lacking the ability to grow in tryptophan, for example ATCC 44076 or PEP4-1 (Jones, 1977). The presence of the trpL lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

2.5 ISOLATION OF SOLUBLE EUKARYOTIC POLYPEPTIDES FROM BACTERIAL CELLS

Another aspect of the invention concerns the isolation of biologically-active recombinant eukaryotic disulfide bond-containing polypeptides from the soluble fraction of bacterial cells.

The inventors have demonstrated that methods described herein may result in secretion of the recombinant fusion polypeptides to the bacterial periplasmic space. It is also contemplated that particular gene constructs may be utilized which alternatively direct the export of the fusion proteins of interest to either the outer membrane or even result in the secretion of the fusion proteins to the culture supernatant, from which the particular polypeptides may be isolated using conventional techniques for the isolation and purification of proteins. Particularly preferred cells for use in the practice of the invention include Gram-negative species, and in particular, members of the Enterobacteriaceae, with *E. coli* and *Salmonella* spp. cells being particularly preferred. Most preferred strains for use in the practice of the invention include *E. coli* strains such as SF103, SF110, UT5600, or RB791 (as disclosed in U.S. Pat. No. 5,508,192, specifically incorporated herein by reference).

The invention also provides for compositions comprising a biologically-active, tissue plasminogen activator operatively linked to a bacterial export signal peptide, and compositions comprising a biologically-active, pancreatic trypsin inhibitor operatively linked to a bacterial export signal peptide.

Using the methods disclosed herein, the inventors have developed novel compositions comprising a soluble biologically-active tissue plasminogen activator operatively linked to a bacterial export signal peptide which has a specific activity of 5–30 $\mu$g/L/OD$_{600}$ unit of culture. The tPA composition obtained was isolatable from the bacterial periplasm.

2.6 PURIFICATION OF EUKARYOTIC PROTEINS FROM THE BACTERIAL PERIPLASM

Because wild-type prokaryotic hosts lack the appropriate enzymes to perform isomerization, and because native bacteria cannot secrete properly folded and active forms of eukaryotic polypeptides, a significant limitation in the purification of valuable recombinant proteins has existed. The present invention, however, overcomes limitations in the art by providing recombinant host cells which produce correctly-folded, biologically-active eukaryotic proteins in soluble, secreted form.

The recombinant proteins of the present invention may contain multiple disulfide bonds. Particularly preferred are proteins which contain at least three disulfide bonds or more. More particularly, preferred proteins include those eukaryotic proteins which contain at least about five or more, or even twelve or more, or most preferably even about fourteen to about seventeen or more disulfide bonds. The inventors have demonstrated success with the method expressing proteins having fewer than four disulfide bonds (such as mammalian pancreatic trypsin inhibitor), and surprisingly have demonstrated success with proteins having fourteen or more disulfide bonds, such as mammalian tPA.

Surprisingly, the inventors have determined that the correct formation of disulfide bonds in proteins of interest can be mediated by engineering prokaryotic host cells to express an eukaryotic foldase (and in particular disulfide isomerases) in conjunction with the specific eukaryotic protein of interest which contain disulfide bonds. This co-expression of a foldase enzyme and the disulfide bond-containing peptide of interest now permits the efficient production of active peptides in recombinant bacterial host cells.

By expressing eukaryotic foldases, and particularly disulfide isomerases, in bacteria concomitantly with nucleic acid segments encoding particular recombinant proteins of interest, yields of the recombinant eukaryotic proteins by prokaryotic hosts have been remarkably increased.

In preferred embodiments, the novel methods disclosed herein have employed bacterial cells such as *E. coli* to produce high yields of multi-disulfide bond-containing eukaryotic enzymes. For example, the inventors have succeeded in producing significant quantities of active, correctly folded tPA in a bacterial cell. This protein has 14 disulfide bonds that must form correctly in order for the protein to be active. The invention is the first demonstration of production of significant quantities of tPA from bacterial host cells which is not associated with insoluble intracellular inclusion bodies. Likewise, the invention has been used to facilitate the production of another commercially important enzyme, pancreatic trypsin inhibitor, and in particular, bovine PTI, using bacterial hosts which co-express an eukaryotic foldase such as PDI. The invention represents a breakthrough in the production of commercial quantities of such multi-disulfide bond-containing proteins of economic interest by providing rapid, inexpensive methodologies for secretion of such proteins by the engineered bacterial cells.

In another preferred embodiment, the invention has demonstrated that recombinant host cells devoid of intrinsic prokaryotic PDI-like activity may be successfully complemented using the eukaryotic foldase-encoding nucleic acid compositions disclosed herein. The inventors have demonstrated that both rat and yeast-derived PDI-encoding DNA segments may be used to provide disulfide bond isomerizing activity to bacterial strains devoid of such activity.

Further aspects of the present invention concern the purification, and in particular embodiments, the substantial purification, of a disulfide bond-containing polypeptide, and in particular a purified tPA or purified PTI protein composition. The term "purified tPA" as used herein, is intended to refer to a tPA composition, isolatable from recombinant bacterial host cells, wherein the tPA is purified to any degree relative to its naturally-obtainable state, i.e., in this case, relative to its purity within a cell extract. A purified tPA composition therefore also refers to a tPA polypeptide, free from the environment in which it may naturally occur or from the recombinant host cell in which it was produced. Likewise, the term "purified PTI" as used herein, is intended to refer to a PTI composition, isolatable from recombinant bacterial host cells, wherein the PTI is purified to any degree relative to its naturally-obtainable state, i.e., in this case, relative to its purity within a cell extract. A purified PTI composition therefore also refers to a PTI polypeptide, free from the environment in which it may naturally occur or from the recombinant host cell in which it was produced.

Generally, "purified" will refer to a tPA or PTI polypeptide composition which has been subjected to fractionation to remove various recombinant host cell components, and which composition substantially retains its tPA or PTI activity. Where the term "substantially purified" is used, this will refer to a composition in which the protein of interest forms the major component of the composition, such as constituting about 25%, about 50%, or even about 75% or greater of the soluble proteins isolated from the periplasm of the recombinant host cells described herein.

Various methods for quantifying the degree of purification of such peptides will be known to those of skill in the art in light of the present disclosure. These include, for example, determining the specific activity of an active fraction, or assessing the number of polypeptides within a fraction by SDS/PAGE analysis. For example, a preferred method for assessing the purity of a tPA composition is to calculate the specific activity of the fraction containing the tPA composition, to compare it to the specific activity of the initial soluble protein extract, and to thus calculate the degree of purity, herein assessed by a "-fold purification number".

As is generally known in the art, to determine the specific activity, one would calculate the number of units of activity per milligram of total protein. In the purification procedure, the specific activity of the starting material, i.e., of the soluble periplasmic extract, would represent the specific activity of the protein of interest in its un-purified state. At each step in the purification and concentration of the protein of interest, one would generally expect the specific activity of the particular enzyme to increase above this value, as it is purified relative to its un-purified state. In preferred embodiments, it is contemplated that one would assess the degree of purity of a given periplasmic fraction comprising recombinant tPA or PTI by comparing its specific activity to the specific activity of the starting material, and representing this as x-fold purification. The use of "fold purification" is advantageous as the purity of an inhibitory fraction can thus be compared to another despite any differences which may exist in the actual units of activity or specific activity.

Generally, "purified" will refer to a protein or polypeptide composition which has been subjected to fractionation to remove various non-peptide components such as other cell components. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques.

As mentioned above, although preferred for use in certain embodiments, there is no general requirement that the recombinant polypeptides always be provided in their most purified state. Indeed, it is contemplated that less substantially purified polypeptides, which are nonetheless enriched in activity relative to the natural state, will have utility in certain embodiments. Partially purified disulfide bond-containing recombinant polypeptide fractions for use in such embodiments may be obtained by subjecting a recombinant host cell periplasmic fraction to one or a combination of the purification steps commonly used for their purification from soluble fractions as described above.

2.7 NUCLEIC ACID SEGMENTS ENCODING EUKARYOTIC FUSION POLYPEPTIDES

The process of selecting and preparing a nucleic acid segment which includes the preferred nucleic acid sequences encoding the peptides of interest is well-known to those of skill in the art. This may alternatively be described as preparing a nucleic acid fragment, or cloning a specific gene. Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (incorporated herein by reference), by introducing selected sequences into recombinant vectors for recombinant production, and by other recombinant DNA techniques generally known to those of skill in the art of molecular biology.

3. BRIEF DESCRIPTION OF THE DRAWINGS

The drawings form part of the present specification and are included to further demonstrate certain aspects of the present invention. The invention may be better understood by reference to one or more of these drawings in combination with the detailed description of specific embodiments presented herein.

FIG. 1. Expression of rPDI in a dsbA mutant. Bacterial cultures JCB570 (dsbA$^+$) and JCB571 (dsbA$^-$) were grown overnight at 37° C. and diluted 100 fold into fresh media. After 30 min, the cultures were divided in two equal parts, one of which received IPTG at a final concentration of 0.5 mM. Cells were harvested at $OD_{600\,nm}=0.4$ and fractionated by osmotic shock. electrophoresis on the osmotic shock supernatant was carried out on 12.5% acrylamide gels under reducing conditions. The rPDIf fragment, which represents a C-terminal fragment of rPDI including the second active site, arises due to an internal translation initiation within rpdi (De Sutter et al., 1994).

Figure 2A:
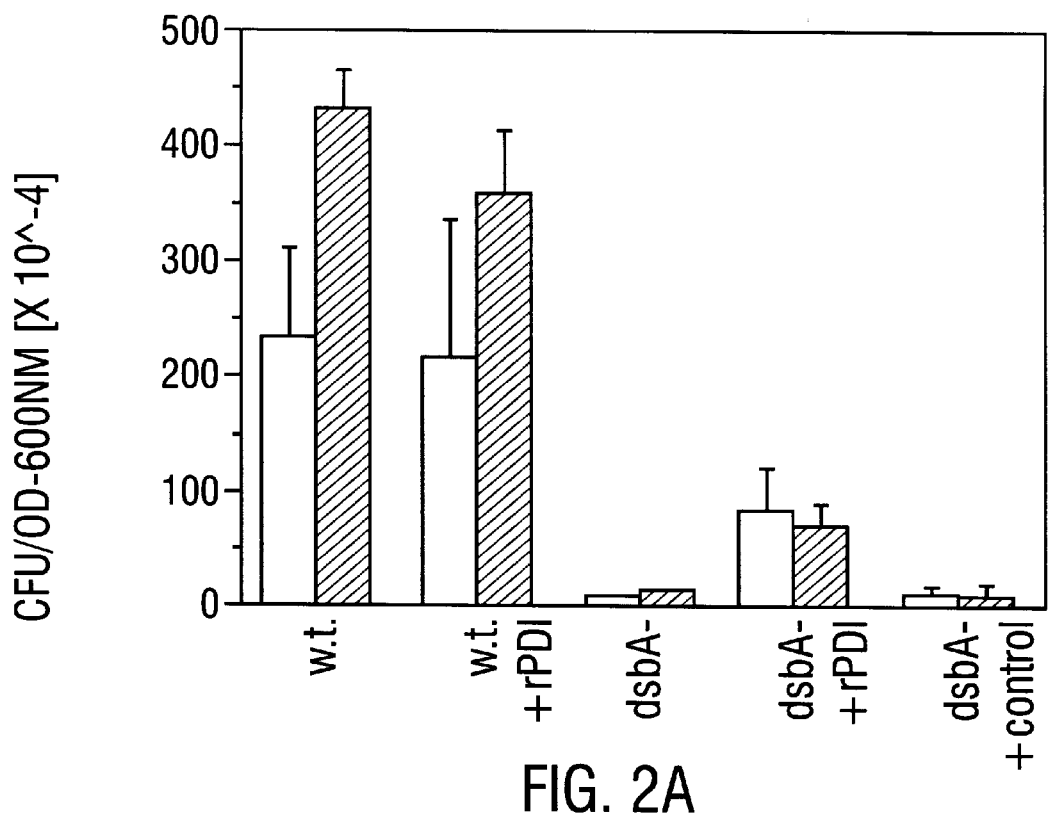

FIG. 2A. rPDI rescues phenotypes of dsbA mutants. F-pilus assembly. Uninduced cells were either infected with the filamentous phage JB4 (Cm$^r$ M13) or used as the donor for conjugation with SF103 as the recipient. Strains: w.t.= JCB502F'; dsbA$^-$=JCB572 F'; Plasmids: rPDI= pLPPsOmpArPDI; control=pTI103. Data represent the average from three independent studies.

Figure 2B:
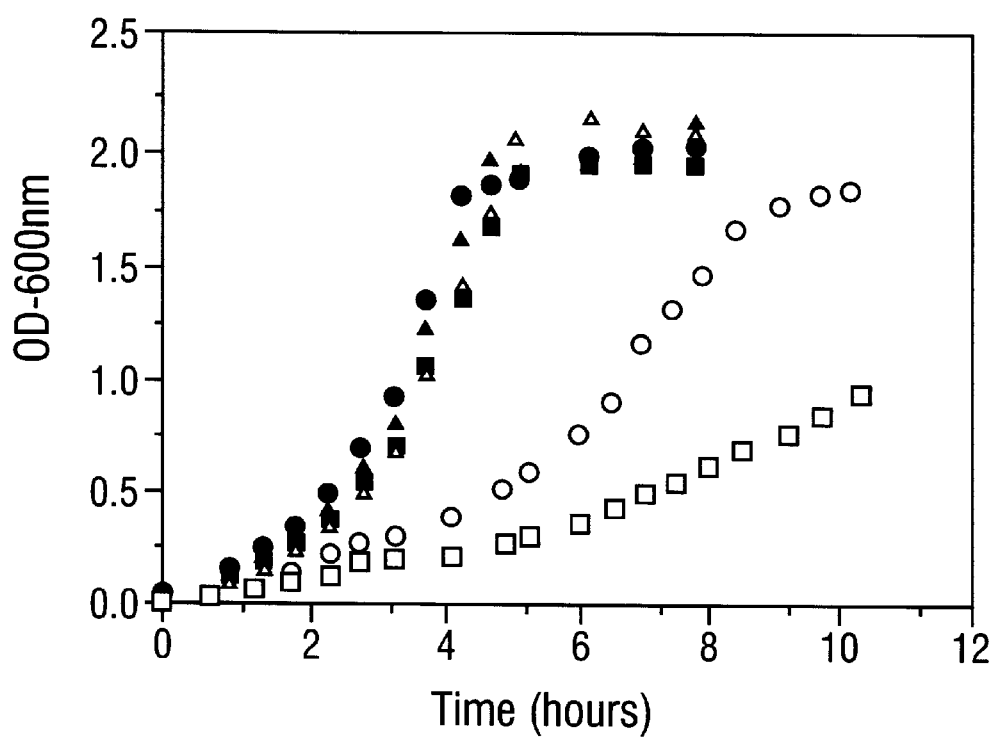

FIG. 2B. rPDI rescues phenotypes of dsbA mutants. Growth in M9 minimal media. Solid symbols: JCB570 (dsbA$^+$), open symbols: JCB571 (dsbA$^-$); (●,○)=no plasmid, (▲,△)=pLPPsOmpArPDI, (■,□)=pTI103 (control plasmid).

Figure 3A:
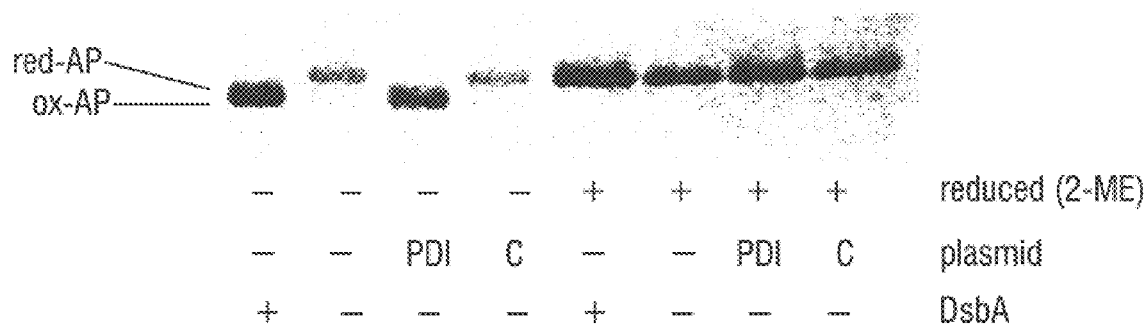

FIG. 3A. Shown is the rPDI rescue of disulfide formation in dsbA$^-$ cells. Oxidation of alkaline phosphatase in dsbA$^-$ and dsbB$^-$ cells with or without rPDI. Bacterial cultures JCB570 (dsbA$^+$ dsbB$^+$), JCB571 (dsbA$^-$ dsbB$^+$) JCB789 (dsbA$^+$ dsbB$^-$) and JCB758 (dsbA$^-$ dsbB$^-$) were labeled with $^{35}$S-TRANSLABEL for 45 sec. followed by a 10 min chase with excess methionine and cysteine. Proteins were precipitated with 10% trichloroacetic acid, treated with iodoacetamide and immunoprecipitated with antisera against alkaline phosphatase. Immune complexes were resolved by electrophoresis under non-reducing or reducing conditions and visualized by autoradiography. The positions of reduced (red-AP), oxidized (ox-AP) and precursor (pre-AP) are indicated.

Figure 3B:
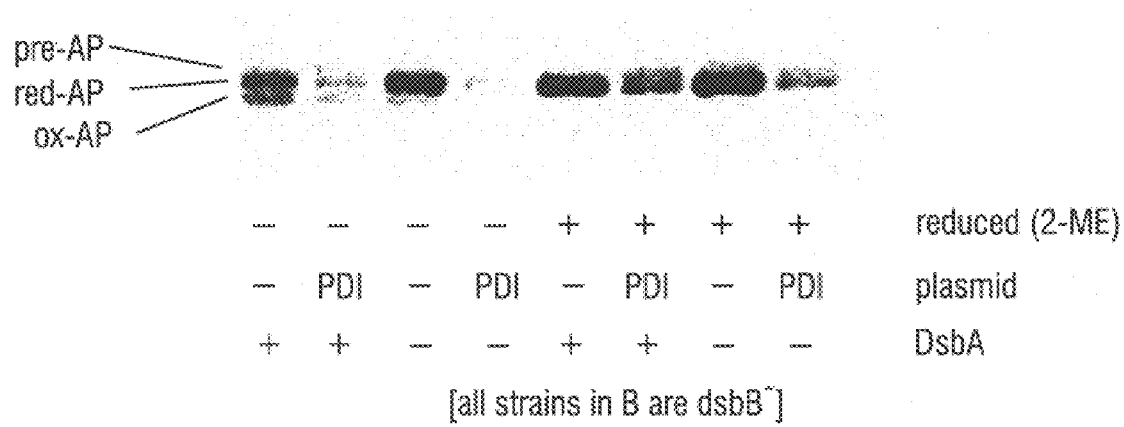

FIG. 3B. Shown are the effects of rPDI on disulfide formation in dsbB$^-$ cells. Oxidation of alkaline phosphatase in dsbA$^-$ and dsbB$^-$ cells with or without rPDI. Bacterial cultures JCB570 (dsbA$^+$ dsbB$^+$), JCB571 (dsbA$^-$ dsbB$^+$) JCB789 (dsbA$^+$ dsbB$^-$) and JCB758 (dsbA$^-$ dsbB$^-$) were labeled with $^{35}$S-TRANSLABEL for 45 sec. followed by a 10 min chase with excess methionine and cysteine. Proteins were precipitated with 10% trichloroacetic acid, treated with iodoacetamide and immunoprecipitated with antisera against alkaline phosphatase. Immune complexes were resolved by electrophoresis under non-reducing or reducing conditions and visualized by autoradiography. The positions of reduced (red-AP), oxidized (ox-AP) and precursor (pre-AP) are indicated.

Figure 4:
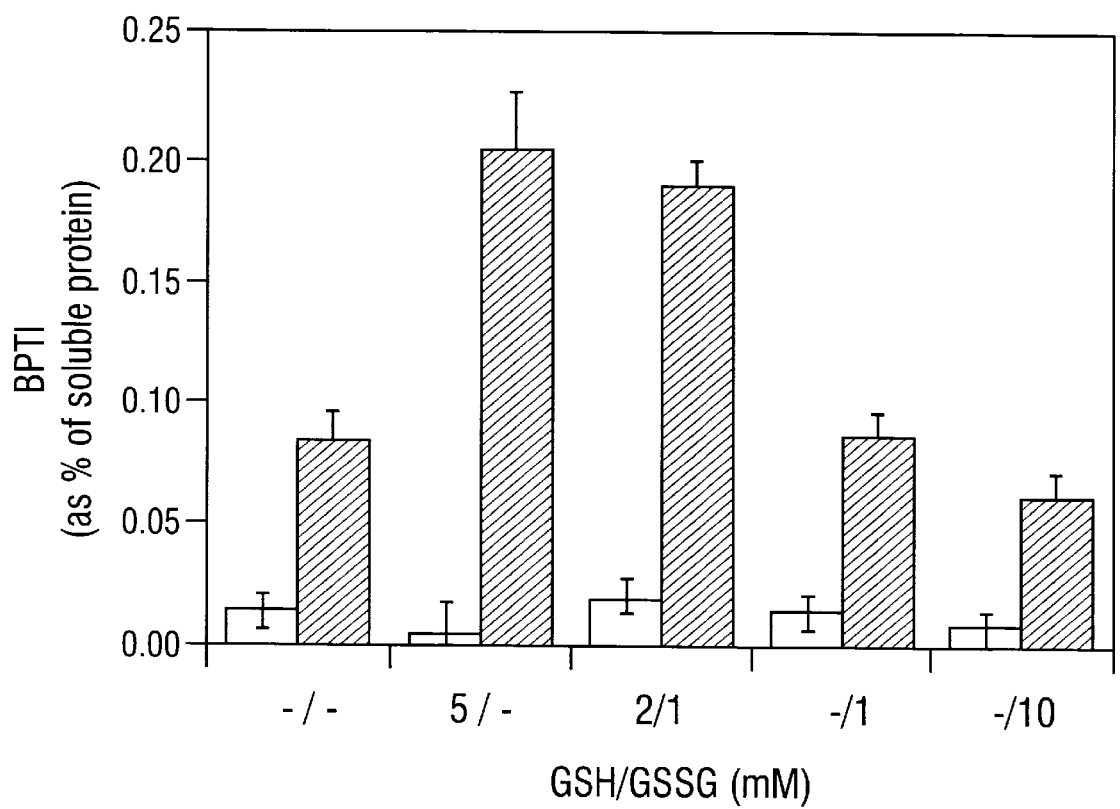

FIG. 4. Coexpression of rPDI improves the yield of BPTI as detected by FLISA. Bacterial cultures JCB570 containing pACYCBPTI (open bars) or pLPPsOmpArPDI and pACY-CBPTI (solid bars) were induced with 0.1 mM IPTG at $OD_{600\,nm}=0.3-0.35$. GSH and/or GSSG as indicated was added 20 min after induction. Five hours after induction the cells were harvested and the concentration of BPTI in the soluble fraction was detected by ELISA. The data reported here represent the average of three independent studies; for each sample ELISAs were performed at least in triplicate.

Figure 5A:
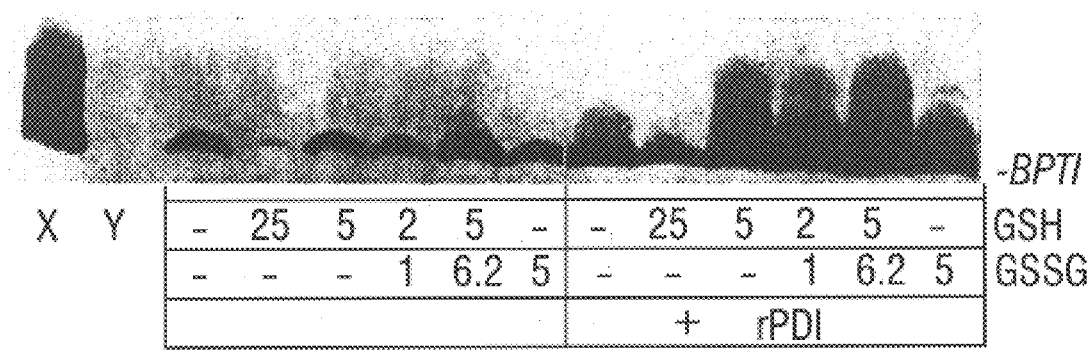

FIG. 5A. Western blot showing expression of BPTI with and without coexpression of rPDI. Bacterial cultures JCB570 (wild type), JCB571 (dsbA⁻) and JCB789 (dsbB⁻) carrying pACYCBPTI were induced (except those marked with a "U") with 0.1 mM IPTG at $OD_{600\,nm}$=0.3–0.35. GSH and GSSG at the indicated mM concentrations were added 20 min after induction. Five hours after induction the cells were harvested and the soluble fraction affinity precipitated with trypsin-agarose beads, electrophoresed through 16% SDS-PAGE Tricine gels and detected by Western blot. Shown are wild-type cells. Lane 1–2 soluble fraction of non-plasmid containing wild type cells with (X) and without (Y) an addition of 2 μg BPTI.

Figure 5B:
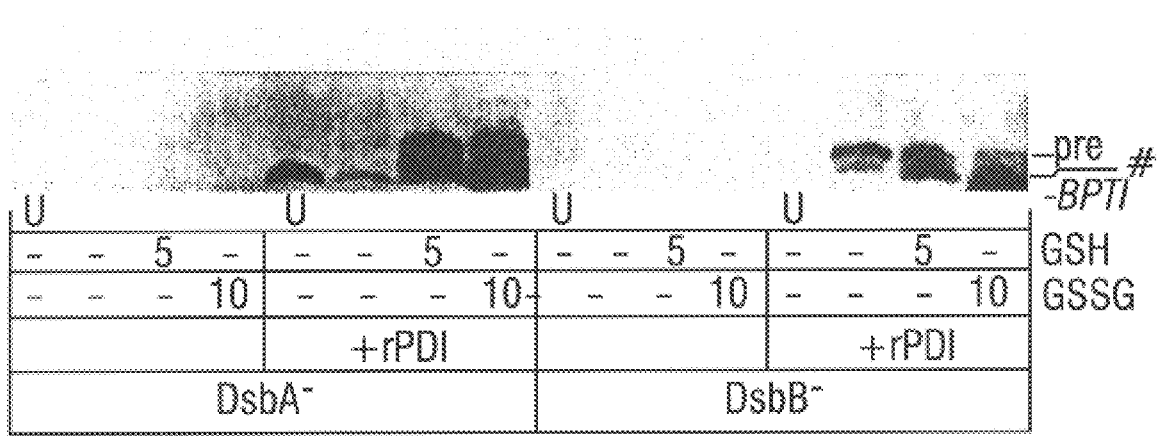

FIG. 5B. Western blot showing expression of BPTI with and without coexpression of rPDI. Bacterial cultures JCB570 (wild type), JCB571 (dsbA⁻) and JCB789 (dsbB⁻) carrying pACYCBPTI were induced (except those marked with a "U") with 0.1 mM IPTG at $OD_{600\,nm}$=0.3–0.35. GSH and GSSG at the indicated mM concentrations were added 20 min after induction. Five hours after induction the cells were harvested and the soluble fraction affinity precipitated with trypsin-agarose beads, electrophoresed through 16% SDS-PAGE Tricine gels and detected by Western blot. Shown are Dsb mutant cells. Symbols: U=uninduced cells; pre=preOmpABPTI; #=degradation product of preOmpArPDI; rPDI=carrying plasmid pLPPsOmpArPDI.

Figure 6:
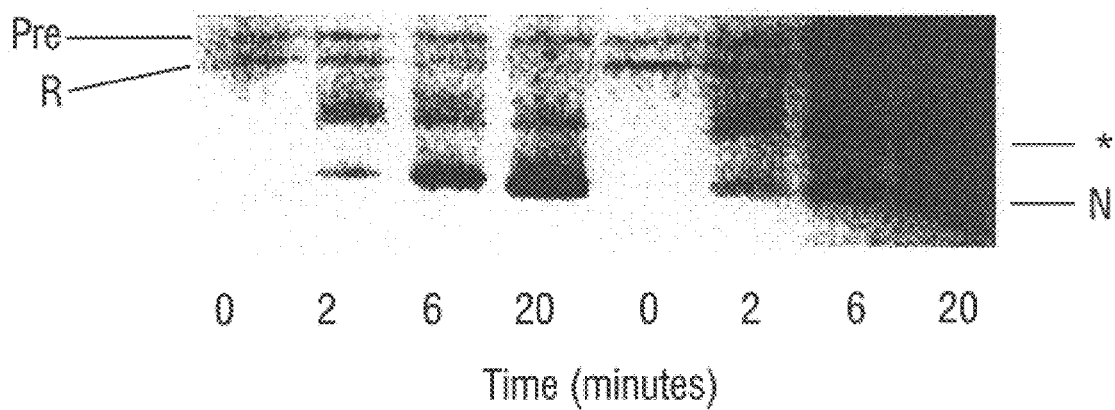

FIG. 6. Accumulation of two disulfide folding intermediates of BPTI in *E. coli* coexpressing rPDI as monitored by non-reducing electrophoresis. Proteins immunoprecipitated from cultures labeled with L-[³⁵S]cysteine for 1 min and quenched with 100 mM iodoacetamide were resolved on non-reducing gels containing 8 M urea. Times indicated are min after the chase. Lanes 1–4, no addition of glutathione. Lanes 5–8, 2 mM GSH added 30 min before pulse. The positions of preOmpA-BPTI (Pre), reduced carboxymethylated BPTI (R), native BPTI (N) and two disulfide intermediates (*) are indicated.

Figure 7A:
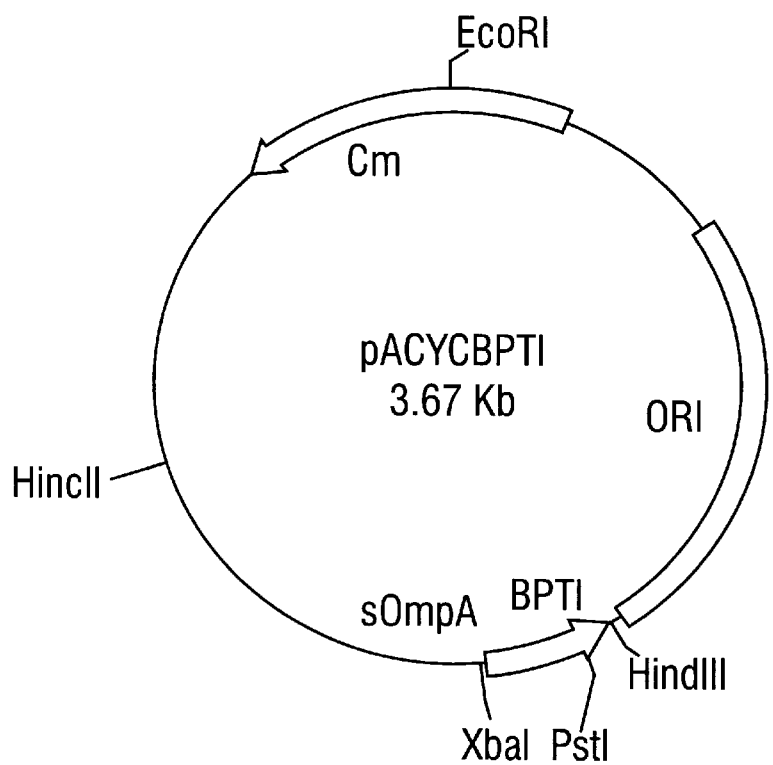
Figure 7B:
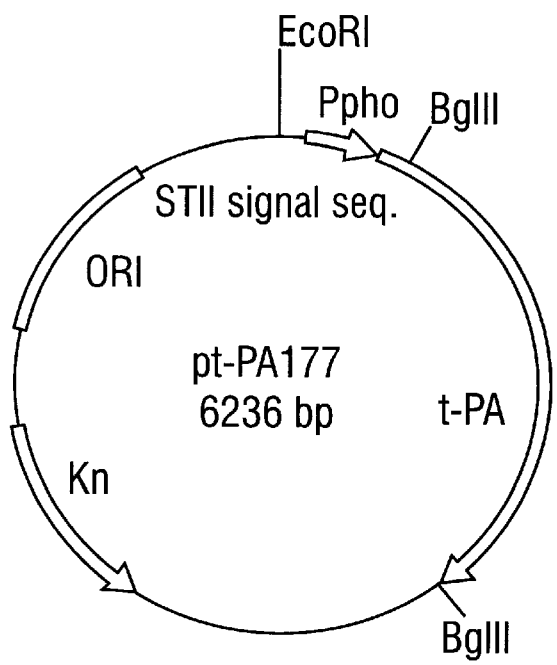

FIG. 7. Restriction maps of the vectors pACYCBPTI and pTPA177.

Figure 8:
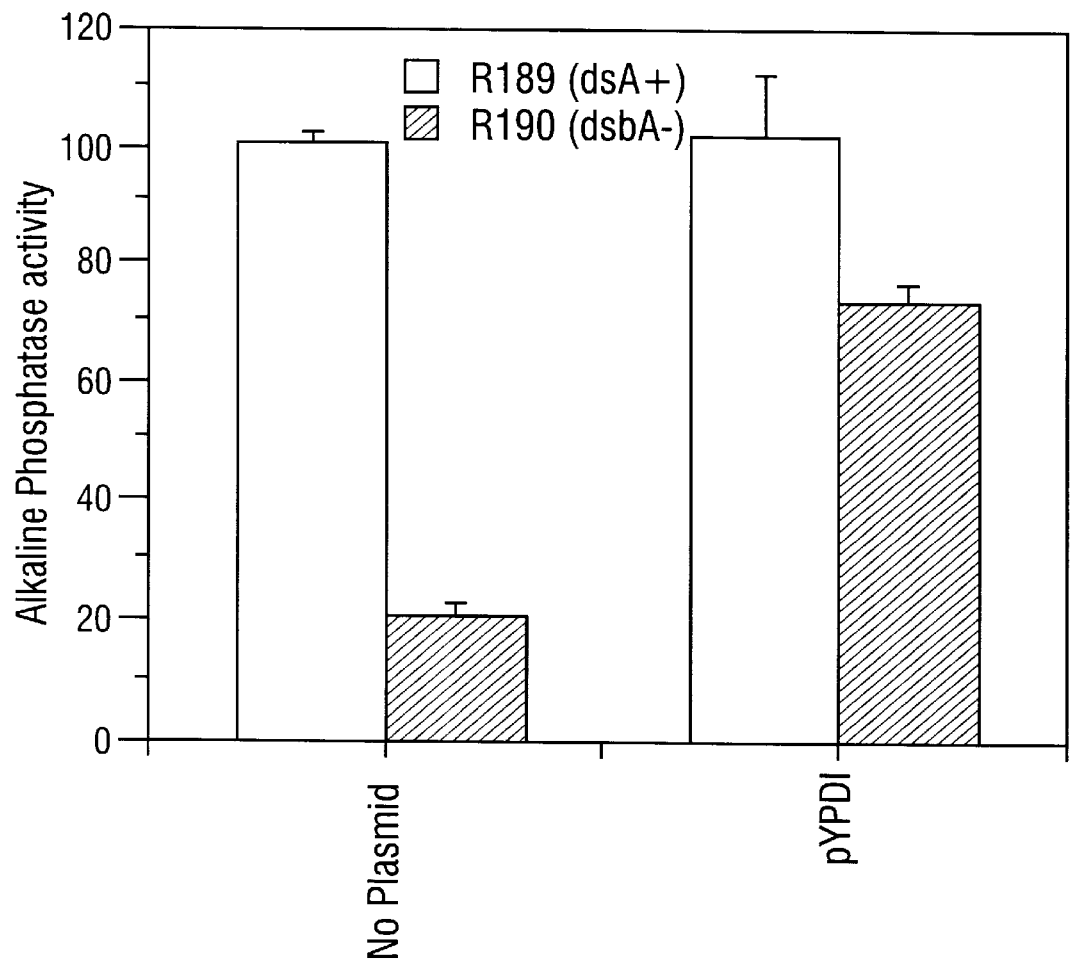

FIG. 8. PhoA activity in R189 and R190 cells containing either no plasmid or pYPDI.

4. DESCRIPTION OF ILLUSTRATIVE EMBODIMENTS

4.1 PROTEIN FOLDING IN VIVO

Extensive studies of the physicochemical aspects of the protein folding problem over the last 40 years have shed light on the nature of the rate limiting steps during the formation of the native conformation. Rate limiting steps in folding include non-covalent processes, such as the alignment of protein subdomains, subunit assembly etc., and covalent processes, for example disulfide bond formation, peptidylproline isomerization, proprotein processing and others. In-vivo, the rate of the covalent steps is catalyzed by a host of cellular enzymes. On the other hand, partially folded species that accumulate because of slow conformational changes are protected from non-productive interactions by the action of chaperones (Gething and Sambrook, 1992). The reductionist approach of analyzing in vitro each of these steps separately has elucidated many mechanistic aspects of the folding problem. However, the folding of proteins in nature occurs in the concentrated milieu of the cellular environment and is probably coupled to biosynthesis and/or export. These additional factors together with the multitude of processes that affect folding in the first place, make it practically impossible to understand how folding proceeds in the cell solely from in vitro data.

The regulation of protein folding is essential for the normal function of the cell and its response to different environments. In addition, protein folding underlies the cause of many human disorders (Wetzel, 1994). A detailed analysis of the in vivo folding pathway can shed light on the influence of various cellular parameters and the nature of rate limiting steps in the folding of proteins in the cell. Such information will ultimately elucidate the molecular basis of this major biological mechanism and could have considerable medical implications.

At present, the protein for which the most detailed information on the kinetics and energetics of folding and on the structure of all the key intermediates is available, is BPTI. BPTI can be secreted to the periplasmic space of *E. coli* where it folds to the native state. Even though BPTI is a heterologous protein, it interacts with bacterial components and its folding is absolutely dependent on the function of *E. coli* oxidoreductases (Ostermeier and Georgiou, 1994).

4.2 PROTEIN FOLDING IN VITRO

The refolding of proteins from denaturant solutions is a spontaneous process directed by the amino acid sequence and the solvent conditions (Matthews 1993; Fersht, 1993). However, even though folding is thermodynamically favored, the yield of the native protein upon refolding in vitro can range from almost 0 to 100%, and the time required for renaturation from milliseconds to days. The reason for such differences relates to the kinetics of the folding process. Exciting recent studies by Fersht and coworkers and others (Otzen et al., 1994; Kuszewski et al., 1994) suggest that the folding of protein subdomains proceeds according to the global collapse model (Dill et al., 1993), via a transition state resembling an expanded form of the native conformation but with no fully formed elements of secondary or tertiary structure. However, for more complex proteins other processes such as the alignment of subdomains or covalent changes introduce rate limiting steps. Covalent changes that limit folding include: cis-trans isomerization of peptidylproline bonds, formation of disulfide bonds, proteolytic processing of proproteins, heme ligation, etc. In the cell most, if not all of these rate limiting processes are facilitated by accessory proteins known as foldases and chaperones (Gething and Sambrook, 1992). Foldases have a clearly defined catalytic activity whereas chaperones perform multiple functions, the most important of which is providing an environment for nascent proteins to fold without the competing process of self-association. The distinction is somewhat artificial because some proteins like protein disulfide isomerase function both as foldases and chaperones, at least in vitro.

The presence of accessory proteins underlies one of the fundamental differences between refolding studies and the way in which folding proceeds in the cell. In addition, in vitro studies are conducted with highly purified polypeptides that are first unfolded and then allowed to relax to their native conformation in dilute solutions. In contrast, the folding of proteins in the cell is probably coupled to protein synthesis, takes place in a much more concentrated environment and is affected by compartmentalization. To complicate matters even more, the growth conditions affect folding directly, by influencing the rates of conformational and covalent changes, and indirectly, by modulating the expression and activity of accessory proteins.

A central question in protein folding is to what extent in vitro studies reflect the physiological folding pathway. In the cell, newly synthesized polypeptides can interact with a variety of chaperones and foldases and, quite possibly, with other cellular components such as membranes, ligand or substrate molecules, and low-molecular-weight solutes. Furthermore, because of the vectorial nature of ribosomal synthesis, and of the export apparatus in the case of secreted proteins, the initial state from which folding commences is non-random.

The denatured state of the protein can exert a significant influence on the folding pathway. Unfortunately, determining the folding pathway in vivo is not a straightforward matter because of the paucity of methods for isolating partially folded proteins. Progress in the elucidation of in vivo folding processes has been possible only for proteins which form exceedingly stable intermediates, such as the P22 endoramnosidase (Goldenberg and King, 1982; Mitraki et al., 1991) and for those where partially folded molecules can be trapped by blocking the formation of disulfide bonds. Studies by the groups of Helenius and Ruddon have employed chemical modification of free thiols to quench folding and dissect the pathway of disulfide bond formation in influenza hemagglutin and human chorionic gonadotropin, respectively (Braakman et al., 1992; Bedows et al., 1992). However, only for the latter protein is the in vitro folding pathway sufficiently well characterized to allow a direct comparison with results of in vivo studies (Huth et al., 1993). Furthermore, the folding of H. influenza hemagglutin and human gonadotropin has been studied in mammalian cells in which the use of genetic techniques for dissecting the role of cellular factors is technically difficult.

The periplasmic space is the cellular compartment defined by the inner and outer membranes of Gram-negative bacteria (Pugsley, 1993). Unlike the cytoplasm, the periplasmic space is maintained under strongly oxidizing conditions, thus facilitating the formation of disulfide bonds in secreted proteins (Walker and Gilbert, 1995; Wülfing and Plückthun, 1994). The majority of periplasmic proteins are exported across the cytoplasmic membrane via the general secretion pathway (Pugsley, 1993) whose components include the proteins SecA, SecY, SecE, SecD, SecF and the recently discovered SecG (Nishiyama et al., 1994). Newly translocated polypeptides are often transiently associated with the external face of the cytoplasmic membrane before they are released into the periplasm. There is evidence that this transient association with the membrane may be important for protein folding (Matsuyama et al., 1993).

The bacterial periplasmic space is topologically equivalent to the endoplasmic reticulum (ER) of eukaryotic cells and, just like in the ER, folding is modulated by the action of several proteins. In addition, the periplasmic PapD chaperone is essential for the assembly of type I pili (Hultgren et al., 1993) and it has been proposed that CIpB may also function as a chaperone (Wülfing and Plückthun, 1994). An important difference between periplasmic and cytoplasmic chaperones is that, unlike GroEL and DnaK, the binding and release of polypeptide substrates from periplasmic chaperones cannot involve ATP binding/hydrolysis since there is no evidence for a high energy phosphate donor in the periplasm.

A protein with cis-trans proline isomerase activity (rotamase) has been isolated from *E. coli* periplasmic fractions and has been shown to be active in a protein refolding assay (Wülfing and Plückthun, 1994). However, the in vivo function of this protein has not yet been elucidated.

The formation of disulfide bonds is catalyzed by the multicomponent dsb system. The dsb genes have been identified by genetic analysis. So far three proteins, DsbA, DsbB and DsbC have been characterized in some detail (Bardwell, 1994, Shevchik et al., 1994, Missiakas et al, 1994). Three additional genes that confer resistance to DTT have been isolated and named dsbD, dsbE and dsbF. Null mutations in dsbD, dsbE and dsbF are known to affect the formation of disulfide bonds in native proteins but little other information is currently available.

4.3 BOVINE PANCREATIC TRYPSIN INHIBITOR

One of the best characterized folding pathways in vitro is that of BPTI. The folding pathway has been elucidated through the isolation and characterization of the one- and two-disulfide intermediates that occur during folding (Creighton and Goldenberg, 1984; Weissman and Kim, 1991; Goldenberg, 1992). The main steps in this pathway are shown below:

Scheme 1

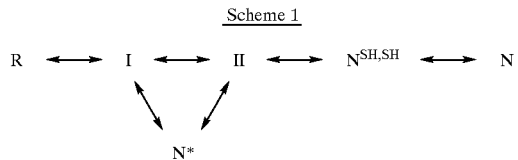

where R is the fully reduced protein, I represents the various one-disulfide species, II represents the native like intermediate N'(30–51, 14–38) as well as two-disulfide species with one non-native and one native disulfide, N* represents the kinetic trap (5–55, 14–38), $N^{SH,SH}$ is the native-like species (3051, 5–55) and N is the native protein with three disulfides. The rate-limiting step in folding is the conversion of II to $N^{SH,SH}$ which is then rapidly oxidized to the native protein. The structure of all major doling intermediates has been extensively characterized using $^1H$ and $^{15}N$ NMR (Van Mierlo et al, 1993). N*, and to a lesser extent N', have a native-like conformation and therefore the activation energy for the conformational change required to position the two thiols in close proximity is high and thus the rate of rearrangement to $N^{SH,SH}$ is slow. The unpaired cysteines of N* are buried within the interior of the protein. Consequently, N* is exceedingly slow to rearrange to other species and is described as a kinetic trap in the folding pathway (Creighton and Goldenberg, 1984).

4.4 EUKARYOTIC PDI

PDI is an endoplasmic reticulum enzyme that catalyzes cysteine oxidation and disulfide bond rearrangement and is essential for cell viability in *Saccharomyces cerevisiae* (Freedman, 1989; Novia et al., 1991). In vitro, PDI has been shown to catalyze all steps in the BPTI folding pathway (Creighton et al., 1980) including the rearrangement of N' and N* to the labile intermediate $N^{SH,SH}$ under conditions that resemble those of the endoplasmic reticulum (Weissman and Kim, 1993). The folding of BPTI is accelerated by the presence of total protein from the endoplasmic reticulum, a phenomenon which has been shown to be totally accounted for by the activity of protein disulfide isomerase (Zapun et al., 1992). Creighton and co-workers (1993) studied the folding of proBPTI produced by an in vitro translation system and imported into microsomes. proBPTI consists of the mature protein with a 13-residue extension on the N-terminal and 7 residue extension at the C-terminal. Its folding was found to be dependent on the presence of GSSG. The formation of native protein was found to be substantially higher than in vitro with complete folding occurring within I min under strongly oxidizing conditions (10 mM GSSG) and within 2 min with 4 mM GSSG. It was postulated that the higher rate of folding in microsomes was due to PDI which was shown to catalyze both disulfide bond formation and rearrangement in proBPTI (Creighton et al., 1993).

The periplasmic space of *E. coli* is topologically equivalent to the endoplasmic reticulum. It is maintained at a redox state favoring the formation of disulfide bonds, a process which is accelerated by at least two interacting proteins, DsbA and DsbB (Bardwell and Beckwith, 1993; Bardwell et al., 1993). The three-dimensional structure of DsbA was solved recently and shown to consist of a thioredoxin-like domain joined to a second domain which may be responsible for substrate specificity (Martin et al., 1993). Similarly, PDI has also been predicted to contain thioredoxin-like domains. Given the analogies between the endoplasmic reticulum and the bacterial periplasmic space, it is not surprising that native BPTI can form in *E. coli* provided it is expressed with a bacterial leader peptide (Marks et al., 1986; Goldenberg, 1988).

Eukaryotic PDI is a 55 kDa enzyme with cysteine oxidoreductase, chaperon and antichaperon activities that catalyzes disulfide formation and rearrangement in the eukaryotic endoplasmic reticulum. In sharp contrast, in Gram-negative bacteria, the formation of disulfide bonds in the periplasm is mediated by DsbA, a strong cysteine oxidase but an inefficient catalyst of disulfide bond isomerization with no known chaperon activity.

The prokaryotic analog was utilized in Eur. Pat. Appl. No. EP 510,658 to direct the expression of a single disulfide bond-containing polypeptide, α-amylase/trypsin inhibitor (RBI), but unfortunately the method required the addition of critical amounts of thiol reagents to the culture medium. The present inventors have shown, however, that the prokaryotic enzyme disclosed in Eur. Pat. Appl. No. EP 510,658 was unable to direct the secretion of significant quantities of either active tPA or active BPTI from bacterial host cells.

Surprisingly, however, when the inventors genetically engineered recombinant host cells to contain a eukaryotic foldase, namely, a disulfide isomerase, the mammalian enzyme was not only secreted into the periplasmic space of bacterial cells, but was also able to catalyze the formation of disulfide bonds, and complement several dsbA mutants which lacked the bacterial enzyme. The function of rPDI was dependent on the dsbB gene suggesting that the reoxidation of this eukaryotic enzyme involves direct interactions with bacterial redox proteins.

Even more importantly, the inventors have demonstrated that co-expression of the eukaryotic rPDI increased the yield of eukaryotic proteins such as BPTI several fold. Whereas PDI is thought to function primarily as an isomerase in the eukaryotic endoplasmic reticulum, rPDI failed to decrease the accumulation of two disulfide folding intermediates of BPTI and thus did not appear to appreciably catalyze the rate limiting step in the oxidative folding pathway of BPTI.

In a breakthrough for protein production in bacterial hosts, the present invention now provides novel methods and compositions to facilitate the expression of eukaryotic foldases in bacterial cells and provides new expression systems which may now be exploited to increase the yield of biologically-valuable eukaryotic proteins which have not been previously been produced in prokaryotic hosts in biologically-active forms.

4.5 METHODS OF NUCLEIC ACID DELIVERY AND DNA TRANSFORMATION

In yet another embodiment, the present invention provides recombinant host cells transformed with polynucleotides which encode an eukaryotic foldase, and particular disulfide bond-containing polypeptides of interest, as well as transgenic cells derived from those transformed or transfected cells. Preferably, a recombinant host cell of the present invention is transformed with a polynucleotide comprising a sequence encoding PDI and a polynucleotide comprising a sequence encoding either tPA or PTI. Means of transforming cells with exogenous polynucleotide such as DNA molecules are well known in the art and include techniques such as calcium-phosphate- or DEAE-dextranmediated transfection, protoplast fusion, electroporation, liposome mediated transfection, direct microinjection and adenovirus infection (Sambrook et al., 1989).

The application of brief, high-voltage electric pulses to a cell culture leads to the formation of nanometer-sized pores in the cell membrane. DNA is taken directly into the cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium chloride-mediated transformation, frequently gives rise to high numbers of target cells being transformed with the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

4.6 DNA SEGMENTS

In other embodiments, it is contemplated that certain advantages will be gained by positioning the DNA segment encoding the fusion polypeptides under the control of a recombinant, or heterologous, promoter. As used herein, a recombinant or heterologous promoter is intended to refer to a promoter that is not normally associated with a DNA segment encoding the eukaryotic peptide in its natural environment. Such promoters may include promoters normally associated with other genes, and/or promoters isolated from any viral, prokaryotic (e.g., bacterial), eukaryotic (e.g., fungal, yeast, plant, or animal) cell, and particularly those of mammalian cells. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to, the Pichia expression vector system (Pharmacia LKB Biotechnology), a baculovirus system for expression in insect cells, or any suitable yeast or bacterial expression system.

The ability of nucleic acid segments to be used as probes to specifically hybridize to the disclosed DNA sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, 15–20, 30, 40, 50, or even of about 100 to about 200 nucleotides or so, identical or complementary to the DNA sequences disclosed herein, are particularly contemplated as hybridization probes for use in, e.g., Southern and Northern blotting. Smaller fragments will generally find use in hybridization embodiments, wherein the length of the contiguous complementary region may be varied, such as between about 10 and about 14 or even up to about 25, 50, or 100 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 25 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as PCR™ (exemplified in U.S. Pat. Nos. 4,683,202 and 4,683,195), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating MSCRAMM-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy, 1990; Maloy et al., 1994; Segal, 1976; Prokop, 1991; and Kuby, 1994, are particularly relevant, providing detailed methods and protocols for molecular biology methods, hybridization and instruction enzyme digestion, plasmid construction, DNA and RNA sequencing mutant construction and analysis and other related methods.

Of course, for some applications, for example, where one desires to prepare mutants employing a mutant primer strand hybridized to an underlying template or where one seeks to isolate eukaryotic polypeptide-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.7 EXPRESSION OF EUKARYOTIC DISULFIDE-BOND CONTAINING PROTEINS

The present inventors contemplate cloning the recombinant polypeptides identified herein, and in particular recombinant tPA and PTI polypeptides. A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule. Techniques such as these would also, of course, be appropriate for the production of a disulfide bond-containing polypeptide in accordance with the present invention.

The first step in such cloning procedures is the screening of an appropriate DNA library, such as, in the present case, a rat, human, bovine, or other mammalian-derived library. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. The operation of such screening protocols are well known to those of skill in the art and are described in detail in the scientific literature, e.g., in Sambrook et al.

(1989) specifically incorporated herein by reference. Moreover, as the present invention encompasses the cloning of genomic segments as well as cDNA molecules, it is contemplated that other suitable methods known to those in the art, such as, e.g., those described by Spoerel et al. (1987), may also be used in connection with cloning a disulfide bond-containing polypeptide, or alternatively an eukaryotic foldase to direct the folding and isomerization of disulfide bonds contained within such polypeptides of interest.

After identifying appropriate DNA molecules, they may be inserted into any one of the many vectors currently known in the art and transferred to a prokaryotic or eukaryotic host cell where it will direct the expression and production of the so-called recombinant version of the protein. This is also, of course, routinely practiced in the art and described in various publications, such as, e.g., Sambrook et al. (1989). Such DNA segments may be contained on a single plasmid vector, or alternatively, the foldase may be encoded by nucleic acid sequences on one vector and the disulfide bond-containing polypeptide of interest may be present on a second plasmid vector which is compatible for co-residence in a single host cell with the first plasmid vector comprising the foldase sequence. The selection of plasmid vectors is well-known to those of skill in the art, and such a selection may be based on the incompatibility grouping of such vectors (IncP, IncQ, etc.). Virtually any such plasmid vectors may be used in the practice of the invention so long as they are replicable in the appropriate prokaryotic host cell employed. In one embodiment, preferred replicons include pACYC184 and pTI103, and in particular, the pACYCBPTI and pLPPsOmpArPDI plasmid constructs derived respectively, therefrom.

It will be understood that recombinant disulfide bond-containing polypeptides may differ from naturally-produced polypeptides in certain ways. In particular, the degree of post-translational modifications, such as, for example, glycosylation and phosphorylation may be different between the recombinant and natural forms.

Recombinant clones expressing nucleic acid segments which encode eukaryotic disulfide-bond containing polypeptides may be used to prepare purified recombinant polypeptides, purified polypeptide-derived antigens as well as mutant or variant recombinant protein species in significant quantities. In particular, the invention provides for the production of recombinant tPA (rtPA) or recombinant PTI (rPTI) in substantial quantities from bacterial host cells.

Additionally, by application of techniques such as DNA mutagenesis, the present invention allows the ready preparation of so-called "second generation" molecules having modified or simplified protein structures. Second generation proteins will typically share one or more properties in common with the full-length polypeptides, such as a particular antigenic/immunogenic epitopic core sequences, or particular catalytic sites, active sites, or ligand binding domains, etc. Epitopic sequences can be provided on relatively short molecules prepared from knowledge of the peptide, or encoding DNA sequence information. Such variant molecules may not only be derived from selected immunogenic/antigenic regions of the protein structure, but may additionally, or alternatively, include one or more functionally equivalent amino acids selected on the basis of similarities or even differences with respect to the natural sequence. This is particularly desirable in the preparation of recombinant polypeptides having enhanced or superior stability, activity, binding, or affinity for substrates and the like.

The general process of recombinant expression of proteins in bacterial hosts, and particularly Gram-negative hosts, is well-known to those of skill in the art. It is generally preferred for the methods described herein that the DNA sequence encoding the particular eukaryotic protein of interest to be secreted be operatively linked to a DNA sequence which encodes a signal peptide sufficient for the translocation of the recombinant polypeptide to the periplasmic space of the bacterial host cell. As it is well-known, operative links between such DNA sequences mean that a translational fusion exists between the heterologous protein and the signal peptide. As a rule, such signal peptides form the N-terminal portion of the secreted heterologous protein. Signal sequences which promote protein translocation to the periplasmic space of Gram-negative bacterial are well-known, as exemplified by those described herein. The *E. coli* OmpA, Lpp, LamB, MalE, PelB, and StII leader peptide sequences have been successfully used in many applications as signal sequences to promote protein secretion in bacterial cells such as those used herein, and are all contemplated to be useful in the practice of the invention.

4.8 PROMOTERS, ENHANCERS, AND SIGNAL SEQUENCE ELEMENTS

The promoters and enhancers that control the transcription of protein-encoding genes are composed of multiple genetic elements. The cellular machinery is able to gather and integrate the regulatory information conveyed by each element, allowing different genes to evolve distinct, often complex patterns of transcriptional regulation.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between elements is flexible, so that promoter function is preserved when elements are inverted or moved relative to one another. In the tk promoter, the spacing between elements can be increased to 50 bp apart before activity begins to decline. Depending on the promoter, it appears that individual elements can function either cooperatively or independently to activate transcription.

Enhancers were originally detected as genetic elements that increased transcription from a promoter located at a distant position on the same molecule of DNA. This ability to act over a large distance had little precedent in classic studies of prokaryotic transcriptional regulation.

Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Aside from this operational distinction, enhancers and promoters are very similar entities. They have the same general function of activating transcription in the cell. They are often overlapping and contiguous, often seeming to have a very similar modular organization. Taken together, these considerations suggest that enhancers and promoters are homologous entities and that the transcriptional activator proteins bound to these sequences may interact with the cellular transcriptional machinery in fundamentally the same way.

Particularly preferred promoters include the lac-lpp promoter which is well-known in the art. Other promoters contemplated to be useful in the practice of the invention include the ara, lac, tac, trc, trp, phoA, $P_{BAD}$, $\lambda_{PL}$, lpp, and the T7 promoter.

4.9 SITE-SPECIFIC MUTAGENESIS

Site-specific mutagenesis is a technique useful in the preparation of individual peptides, or biologically functional equivalent proteins or peptides, through specific mutagenesis of the underlying DNA. The technique, well-known to those of skill in the art, further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 14 to about 25 nucleotides in length is preferred, with about 5 to about 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially-available and their use is generally well-known to those skilled in the art. Double-stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double-stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants. Specific details regarding these methods and protocols are found in the teachings of Maloy (1990); Maloy et al. (1994); Segal (1976); Prokop and Bajpai (1991); Maniatis et al. (1982); and Sambrook et al. (1989), each incorporated herein by reference, for that purpose.

The PCR™-based strand overlap extension (SOE) for site-directed mutagenesis is particularly preferred for site-directed mutagenesis of the nucleic acid compositions of the present invention. The techniques of PCR™ are well-known to those of skill in the art, as described hereinabove. The SOE procedure involves a two-step PCR™ protocol, in which a complementary pair of internal primers (B and C) are used to introduce the appropriate nucleotide changes into the wild-type sequence. In two separate reactions, flanking PCR™ primer A (restriction site incorporated into the oligo) and primer D (restriction site incorporated into the oligo) are used in conjunction with primers B and C, respectively to generate PCR™ products AB and CD. The PCR™ products are purified by agarose gel electrophoresis and the two overlapping PCR™ fragments AB and CD are combined with flanking primers A and D and used in a second PCR™ reaction. The amplified PCR™ product is agarose gel purified, digested with the appropriate enzymes, ligated into an expression vector, and transformed into E. coli JM101, XL1-BLUE™ (Stratagene, La Jolla, Calif.), JM105, TG1 (Carter et al., 1985), or other such suitable cells as deemed appropriate depending upon the particular application of the invention. Clones are isolated and the mutations are confirmed by sequencing of the isolated plasmids. Beginning with the native gene sequences, for example, the nucleic acid sequences encoding eukaryotic disulfide-bond-containing polypeptides such as PTI or tPA and the like, suitable clones and subclones may be made in the appropriate vectors from which site-specific mutagenesis may be performed.

4.10 BIOLOGICAL FUNCTIONAL EQUIVALENTS

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to Table 1.

TABLE 1

| Amino Acids | | | Codons | | | | |
|---|---|---|---|---|---|---|---|
| Alanine | Ala | A | GCA | GCC | GCG | GCU | |
| Cysteine | Cys | C | UGU | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |

TABLE 1-continued

| Amino Acids | | | Codons | | | | | |
|---|---|---|---|---|---|---|---|---|
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUC | GUU | | |
| Tryptophan | Trp | W | UGG | | | | | |
| Tyrosin | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred. It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0 ±1); glutamate (+3.0 ±1); serine (+0.3); asparagine (+0.2); glutamine (+0.2); glycine (0); threonine (−0.4); proline (−0.5 ±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.11 PHARMACEUTICAL COMPOSITIONS

In certain embodiments, the inventors contemplate the formulation of the eukaryotic polypeptides produced in bacteria using the methods disclosed herein into pharmaceutically-acceptable compositions for administration to an animal, and in particular, a mammal such as a human.

Such pharmaceutical compositions may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.12 LIPOSOMES AND NANOCAPSULES

In certain aspects, it may be desirable to formulate the novel fusion proteins of the present invention into formulations for administration to an animal or other organism. The administration of the compositions disclosed herein may be accomplished with pharmaceutical formulations of these eukaryotic polypeptides in the form of liposomes or nanocapsules for either general administration or for specific targeting to certain areas, cells, or tissues of an animal.

The formation and use of liposomes is generally known to those of skill in the art (see e.g., Couvreur et al., 1977; 1988, which describe the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987).

Liposomes have been used successfully with a number of cell types that are normally resistant to transfection by other procedures including T cell suspensions, primary hepatocyte cultures and PC 12 cells (Muller el al., 1990). In addition, liposomes are free of the DNA length constraints that are typical of viral-based delivery systems. Liposomes have been used effectively to introduce genes, drugs (Heath and Martin, 1986; Heath et al., 1986; Balazsovits et al., 1989), radiotherapeutic agents (Pikul et al., 1987), enzymes (Imaizumi et al., 1990a; Imaizumi et al., 1990b), viruses (Faller and Baltimore, 1984), transcription factors and allosteric effectors (Nicolau and Gersonde, 1979) into a variety of cultured cell lines and animals.

In addition to the teachings of Couvreur et al. (1977; 1988), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for phannaceutically-acceptable nanocapsule formulations of dopamine receptor agonists. Nanocapsules can generally entrap compounds in a stable and reproducible way (Henry-Michelland et al., 1987). To avoid side effects due to intracellular polymeric overloading, such ultrafine particles (sized around 0.1:m) should be designed using polymers able to be degraded in vivo. Biodegradable polyalkylcyanoacrylate nanoparticles that meet these requirements are contemplated for use in the present invention, and such particles may be are easily made, as described (Couvreur et al., 1984; 1988).

4.13 ANTIBODY COMPOSITIONS

In another aspect, the present invention contemplates an antibody that is immunoreactive with one of the recombinant eukaryotic polypeptides obtained by the disclosed methods of producing such fusion peptides in a bacterial host. Reference to antibodies throughout the specification includes whole polyclonal and monoclonal antibodies, and parts thereof, either alone or conjugated with other moieties. Antibody parts include Fab and F(ab)$_2$ fragments and single chain antibodies. The antibodies may be made in vivo in suitable laboratory animals or in vitro using recombinant DNA techniques. An antibody can be a polyclonal or a monoclonal antibody. In a preferred embodiment, an antibody is a polyclonal antibody.

Means for preparing and characterizing antibodies are well known in the art (See, e.g., Harlow and Lane, 1988). Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately about $5 \times 10^7$ to about $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al. (1977). The use of electrically induced fusion methods is also appropriate (Goding, 1986).

Antibodies, both polyclonal and monoclonal, specific for the eukaryotic fusion proteins may be prepared using conventional immunization techniques, as will be generally known to those of skill in the art. A composition containing antigenic epitopes of particular eukaryotic fusion protein can be used to immunize one or more experimental animals, such as a rabbit or mouse, which will then proceed to produce specific antibodies against epitope-containing eukaryotic fusion proteins. Polyclonal antisera may be obtained, after allowing time for antibody generation, simply by bleeding the animal and preparing serum samples from the whole blood.

When peptides are used as antigens to raise polyclonal sera, one would expect considerably less variation in the clonal nature of the sera than if a whole antigen were employed. Unfortunately, if incomplete fragments of an epitope are presented, the peptide may very well assume multiple (and probably non-native) conformations. As a result, even short peptides can produce polyclonal antisera with relatively plural specificities and, unfortunately, an antisera that does not react or reacts poorly with the native molecule.

Polyclonal antisera according to present invention is produced against peptides that are predicted to comprise whole, intact epitopes. It is believed that these epitopes are, therefore, more stable in an immunologic sense and thus express a more consistent immunologic target for the immune system. Under this model, the number of potential B-cell clones that will respond to this peptide is considerably smaller and, hence, the homogeneity of the resulting sera will be higher. In various embodiments, the present invention provides for polyclonal antisera where the clonality, i.e., the percentage of clone reacting with the same molecular determinant, is at least 80%. Even higher clonality—90%, 95% or greater—is contemplated.

It is proposed that the monoclonal antibodies of the present invention will find useful application in standard immunochemical procedures, such as ELISA and Western blot methods, as well as other procedures which may utilize antibody specific to the particular epitopes. Additionally, it is proposed that monoclonal antibodies specific to the particular eukaryotic fusion peptide may be utilized in other useful applications. For example, their use in immunoabsorbent protocols may be useful in purifying native or recombinant peptide species or synthetic or natural variants thereof. In general, both poly- and monoclonal antibodies against these peptides may be used in a variety of embodiments. For example, they may be employed in antibody cloning protocols to obtain cDNAs or genes encoding the peptides disclosed herein or related proteins. They may also be used in inhibition studies to analyze the effects of particular peptides in cells or animals. A particularly useful application of such antibodies is in purifying the fusion protein, for example, using an antibody affinity column. The operation of all such immunological techniques will be known to those of skill in the art in light of the present disclosure.

4.14 DETECTION OF PEPTIDE AND ANTIBODY COMPOSITIONS

It will be further understood that certain of the polypeptides may be present in quantities below the detection limits of typical staining procedures such as Coomassie brilliant blue or silver staining, which are usually employed in the analysis of SDS/PAGE gels, or that their presence may be masked by an inactive polypeptide of similar $M_r$. Although not necessary to the routine practice of the present invention, it is contemplated that other detection techniques may be employed advantageously in the visualization of particular polypeptides of interest. Immunologically-based techniques such as Western blotting using enzymatically-, radiolabel-, or fluorescently-tagged antibodies described herein are considered to be of particular use in this regard. Alternatively, the peptides of the present invention may be detected by using antibodies of the present invention in combination with secondary antibodies having affinity for such primary antibodies. This secondary antibody may be enzymatically- or radiolabeled, or alternatively, fluorescently- , or colloidal gold-tagged. Means for the labeling and detection of such two-step secondary antibody techniques are well-known to those of skill in the art.

4.15 PROTEIN PURIFICATION METHODS

Further aspects of the present invention concern the purification, and in particular embodiments, the substantial purification, of the recombinant eukaryotic fusion proteins produced in bacterial host cells. The phrase "purified protein" as used herein, is intended to refer to a polypeptide composition, isolatable from the soluble fraction or cell culture supernatant of a recombinant bacterial cell, wherein the protein is purified to any degree relative to its naturally-obtainable state, i.e., in this case, relative to its purity within the soluble fraction or cell culture supernatant of a recombinant bacterial cell. A purified protein, therefore, also refers to isolated protein, free from the environment in which it may naturally occur.

Generally, "purified" will refer to a protein composition which has been subjected to fractionation to remove various non-polypeptide components, and which composition substantially retains its normal ability. For example, in the case of enzymes such as tPA or BPTI, that the purified protein retain its biological or enzymatic activity. Where the term "substantially purified" is used, this will refer to a composition in which F factor forms the major component of the composition, such as constituting from about 50% to about 60% of the protein in the composition or more.

Various methods for quantifying the degree of purification of the recombinant polypeptides of the present invention will be known to those of skill in the art in light of the present disclosure. These include, for example, determining the specific activity of an active fraction, or assessing the number of polypeptides within a fraction by SDS/PAGE analysis. A preferred method for assessing the purity of the protein fraction is to calculate the specific activity of the fraction, to compare it to the specific activity of the initial source (e.g., the soluble fraction or cell culture supernatant, and to thus calculate the degree of purity, herein assessed by a "-fold purification number." The actual units used to represent the amount of inhibitory activity will, of course, be dependent upon the particular assay technique chosen to follow the purification. For example, in the case of tPA, the inventors prefer to use a commercially-available chromogenic assay (SPECTROLYSE™, American Diagnostics, Inc., Greenwich, TC).

Likewise, in the case of BPTI, the inventors have quantitated the enzyme using the ELISA assay as described in Section 5.

As is generally known in the art, to determine the specific activity, one would calculate the number of units of activity per milligram of total protein. In the purification procedure, the specific activity of the starting material, i.e., of the soluble fraction or culture supernatant containing the desired recombinant, would represent the specific activity of the protein in its natural state. At each step, one would generally expect the specific activity of the protein to increase above this value, as it is purified relative to its natural state. In preferred embodiments, it is contemplated that one would assess the degree of purity of a given protein fraction by comparing its specific activity to the specific activity of the starting material, and representing this as X-fold purification. The use of "-fold purification" is advantageous as the purity of an inhibitory fraction can thus be compared to another despite any differences which may exist in the actual units of activity or specific activity.

It is contemplated that the eukaryotic fusion polypeptides of the present invention be purified to between about 10-fold and about 200-fold, and preferably, between about 30-fold and about 150-fold.

Generally, "purified" will refer to a composition comprising a eukaryotic fusion protein which has been subjected to fractionation to remove various non-polypeptide components such as other cell components. Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. A specific example presented herein is the purification of the proteins using gel filtration chromatography.

The preferred purification method disclosed hereinbelow contains several steps and represents the best mode presently known by the inventors to prepare a substantially purified protein. This method is currently preferred as it results in the substantial purification of the polypeptide, as assessed by gel filtration, in yields sufficient for further characterization and use. This preferred mode of protein purification involves the execution of certain purification steps in the order described hereinbelow. However, as is generally known in the art, it is believed that the order of conducting the various purification steps may be changed, or that certain steps may be omitted, and still result in a suitable method for the preparation of a substantially purified recombinant protein.

As mentioned above, although preferred for use in certain embodiments, there is no general requirement that the protein always be provided in its most-purified state. Indeed, it is contemplated that less substantially purified proteins, which is nonetheless enriched in the desired recombinant protein activity relative to the natural state, will have utility in certain embodiments. For example crude tPA may be employed in assay kits for determining the activity of tPA inhibitors. Similarly, BPTI may be employed to detect trypsin activity.

One important technique in the art for the purification of polypeptides is the method of affinity chromatography. Affinity chromatography is generally based on the recognition of a protein by a substance such as a ligand or an antibody. The column material may be synthesized by covalently coupling a binding molecule, such as an activated dye, for example to an insoluble matrix. The column material is then allowed to adsorb the desired substance from solution. Next, the conditions are changed to those under which binding does not occur and the substrate is eluted. The requirements for successful affinity chromatography are:

1) that the matrix must specifically-adsorb the molecules of interest;
2) that other contaminants remain unadsorbed;
3) that the ligand must be coupled without altering its binding activity;
4) that the ligand must bind sufficiently tight to the matrix; and
5) that it must be possible to elute the molecules of interest without destroying them.

A preferred embodiment of the present invention is an affinity chromatography method for purification of the recombinant eukaryotic polypeptides from solution (including cell culture supernatant, and cell soluble extracts) wherein the matrix contains an antibody specific for the particular polypeptide, covalently-coupled to a Sepharose CL6B or CL4B. Such an affinity matrix would then bind the polypeptides of the present invention directly and allows their separation by elution with an appropriate gradient such as a buffer, salt, GuHCl, pH, or urea.

4.16 CHROMATOGRAPHY AND SDS-PAGE OF THE RECOMBINANT POLYPEPTIDES

The recombinant polypeptides of the present invention may be particularly characterized based on a number of physical, chemical, and biophysical properties. For example, the molecular weight of a given protein may be determined using conventional means known to those of skill in the art, e.g. as determined by gel filtration column chromatography.

Gel filtration chromatography is a means of determining molecular weight of protein species, and is a well-known technique. In general, a preferred gel to be used in the procedures of the present invention is a three dimensional network which has a random structure. Molecular sieve gels consist of cross-linked polymers that do not bind or react with the material being analyzed or separated. For gel filtration purposes, the gel material is generally uncharged. The space within the gel is filled with liquid and the liquid phase constitutes the majority of the gel volume. Materials commonly used in gel filtration columns include dextran, agarose and polyacrylamide.

Dextran is a polysaccharide composed of glucose residues and is commercially available under the names SEPHADEX (Phamacia Fine Chemicals, Inc.). The beads are prepared with various degrees of cross-linking in order to separate different sized molecules by providing various pore sizes. The size of the cross-linking molecule can also be increased to obtain larger pore sizes. Alkyl dextran is cross-linked with N, N'-methylenebisacrylamide to from SEPHACRYL-S300 which allows strong beads to be made that fractionate in larger ranges than SEPHADEX can achieve.

The most preferred method of gel filtration in the present invention is agarose gel filtration. Agarose is a linear polymer of D-galactose and 3,6 anhydro-1-galactose and the gel polymer is formed by hydrogen bonds. In gel filtration applications the agarose is provided as porous beads and the concentration of agarose determines pore size. This type of gel is useful for the separation of large, globular molecules such as proteins and for long linear molecules such as DNA. Agarose is commercially available under the name Sepharose (Sigma) in several pore sizes. In the procedures of the present invention, SEPHAROSE 4B which fractionates in the molecular weight range of $3 \times 10^5$ to $3 \times 10^6$ is the most preferred agarose preparation.

Polyacrylamide is a polymer of cross-linked acrylamide prepared with N, N'-methylenebisacrylamide as the cross-linking agent. Polyacrylamide is available in a variety of pore sizes from Bio-Rad Laboratories (USA) to be used for separation of different size particles.

The gel material swell in water and in a few organic solvents. Swelling is the process by which the pores become filled with liquid to be used as eluant. As the smaller molecules enter the pores, their progress through the gel is retarded relative to the larger molecules which do not enter the pores. This is the basis of the separation. The beads are available in various degrees of fineness to be used in different applications. The coarser the bead, the faster the flow and the poorer the resolution. Superfine is to be used for maximum resolution, but the flow is very slow. Fine is used for preparative work in large columns which require a faster flow rate. The coarser grades are for large preparations in which resolution is less important than time, or for separation of molecules with a large difference in molecular weights.

However, it is, of course, generally understood by those of skill in the art that both the migration of a polypeptide using SDS/PAGE, and the mobility of a polypeptide using different sizing columns can vary with different experimental conditions (Capaldi et al., 1977). It will therefore be appreciated that under differing electrophoretic and chromatographic conditions, the molecular weight assignments quoted above may vary.

It will be further understood that certain of the polypeptides may be present in quantities below the detection limits of the Coomassie brilliant blue staining procedure usually employed in the analysis of SDS/PAGE gels, or that their presence may be masked by an inactive polypeptide of similar Mr. Although not necessary to the routine practice of the present invention, it is contemplated that other detection techniques may be employed advantageously in the visualization of each of the polypeptides present within the growth factor. Immunologically-based techniques such as Western blotting using enzymatically-, radiolabel-, or fluorescently-tagged secondary antibodies are considered to be of particular use in this regard.

4.17 MODES FOR CARRYING OUT THE INVENTION

In the process herein, expression of the pdi gene is induced just before (immediately prior to) heterologous gene expression. The heterologous eukaryotic polypeptide and the PDI or rPDI protein are both secreted into the periplasm or the heterologous polypeptide is secreted into the culture medium of the bacteria into which nucleic acid encoding these polypeptides has been introduced. Preferably, the polypeptide is recovered from the periplasm of the bacteria.

The pdi nucleic acid may be from any eukaryotic source, but preferably human, rat, or yeast, and is generally the native sequence. It is suitably separately placed from the nucleic acid encoding the heterologous polypeptide if nucleic acids are on the same vector, i.e., they are not linked. In addition, the nucleic acid encoding PDI and the nucleic acid encoding the heterologous polypeptide are under separate, different inducible promoters so that induction of expression can occur in the required sequential order. The nucleic acid encoding PDI and the nucleic acid encoding the heterologous polypeptide may be integrated into the host cell genome or contained on autonomously replicating plasmids.

In one alternative, the recombinant host cell comprises two separate vectors respectively containing the nucleic acid encoding PDI and the nucleic acid encoding the heterologous polypeptide.

In another alternative, the nucleic acid encoding PDI and the nucleic acid encoding the heterologous polypeptide are contained on the same vector but are under the control of separate inducible promoters and separate signal sequences.

The heterologous nucleic acid (e.g., cDNA or genomic DNA) is suitably inserted into a replicable vector for expression in the bacterium under the control of a suitable promoter for bacteria. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more marker genes, and an inducible promoter.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells.

The DNA encoding the polypeptide of interest herein may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, penicillinase, lpp, or heat-stable enterotoxin II leaders.

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria. The origin of replication from either pBR322 or pACYC184 is suitable for most Gram-negative bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen.

The expression vector for producing a heterologous polypeptide also contains an inducible promoter that is recognized by the host bacterial organism and is operably linked to the nucleic acid encoding the polypeptide of interest. It also contains a separate inducible promoter operably linked to the nucleic acid encoding PDI. Inducible promoters suitable for use with bacterial hosts include the b-lactamase and lactose (lac) promoter systems (Chang et al., 1978; Goeddel et al., 1979), the arabinose (ara) promoter system (Guzman et al., 1992), alkaline phosphatase (phoA), a tryptophan (trp) promoter system (Goeddel, 1980; Eur. Pat. Appl. Publ. No. EP 36,776), $\lambda_{PL}$ promoter, and hybrid promoters such as the tac promoter (deBoer et al., 1983). However, other known bacterial inducible promoters are suitable. Their nucleotide sequences have been published, thereby enabling a skilled worker operably to ligate them to DNA encoding the polypeptide of interest or to the pdi gene (Siebenlist et al., 1980) using linkers or adaptors to supply any required restriction sites.

Promoters for use in bacterial systems also generally contain a Shine-Dalgarno (S.D.) sequence operably linked to the DNA encoding the polypeptide of interest. The promoter can be removed from the bacterial source DNA by restriction enzyme digestion and inserted into the vector containing the desired DNA. Construction of suitable vectors containing one or more of the above-listed components employs standard ligation techniques. Isolated plasmids or DNA fragments are cleaved, tailored, and re-ligated in the form desired to generate the plasmids required.

For analysis to confirm correct sequences in plasmids constructed, the ligation mixtures are used to transform *E. coli* K12 strain 294 (ATCC 31446), SF103, SF110, UT5600, RB791, or any other suitable strain, and successful transformants are selected using antibiotic resistance where appropriate. Plasmids from the transformants are prepared, analyzed by restriction endonuclease digestion, and/or sequenced by the method of Sanger et al. (1977) or Messing et al. (1981) or by the method of Maxam et al. (1980).

Suitable bacteria for this purpose include Archaebacteria and Eubacteria, especially Eubacteria, and most preferably Enterobacteriaceae. Examples of useful bacteria include Escherichia, Enterobacter, Azotobacter, Erwinia, Bacillus, Pseudomonas, Klebsiella, Proteus, Salmonella, Serratia, Shigella, Rhizobia, Vitreoscilla, and Paracoccus. Suitable *E. coli* hosts include *E. coli* SF103, SF110, UT5600, RB791, W3110 (ATCC 27325), *E. coli* 294 (ATCC 31446), *E. coli* B, and *E. coli* $\lambda^{1776}$ (ATCC 31537). These examples are illustrative rather than limiting. Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYC177, or pKN410 are used to supply the replicon.

*E. coli* strains such as ATCC 98380, or those disclosed in U.S. Pat. No. 5,508,192 (SF103, SF110, UT5600, and RB791) are preferred hosts or parent hosts for the practice of the invention, because they are protease deficient recombinantly engineered host cells which provide excellent recovery of recombinant polypeptides. Preferably, the host cell should secrete minimal amounts of proteolytic enzymes. Alternatively, other *E. coli* strains, for example, *E. coli* strain W3110, may be modified to effect a genetic mutation in the genes encoding proteins, with examples of such hosts including *E. coli* W3110 strain 1A2, which has the complete genotype tonAD; *E. coli* W3110 strain 9E4, which has the complete genotype tonAD ptr3; *E. coil* W3110 strain 27C7 (ATCC 55,244), which has the complete genotype tonAD ptr3 phoADE15 D(argF-lac)169 ompTD degP41kan$^r$; *E. coil* W3110 strain 37D6, which has the complete genotype tonAD ptr3 phoADE15 D(argF-lac)169 ompTD degP41kan$^r$ rbs7D ilvG; *E coli* W3110 strain 40B4, which is strain 37D6 with a non-kanamycin resistant degP deletion mutation; *E. coli* W3110 strain 33D3, which has the complete genotype tonA ptr3 lacIq LacL8 ompT degP kan$^r$; *E. coil* W3110 strain 36F8, which has the complete genotype tonA phoA D(argF-lac) ptr3 degP kan$^R$ ilvG$^+$, and is temperature resistant at 37° C.; and an *E. coil* strain having the mutant periplasmic protease(s) disclosed in U.S. Pat. No. 4,946,783.

Host cells are transfected and preferably transformed with the above-described expression vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., (1989), is generally used for bacterial cells that contain substantial cell-wall barriers. Another method for transformation employs polyethylene glycol/DMSO, as described in Chung and Miller (1988). Yet another method is the use of the technique termed electroporation.

Bacterial cells used to produce the polypeptide of interest for purposes of this invention are cultured in suitable media in which the promoters for the nucleic acid encoding the heterologous polypeptide and for the nucleic acid encoding PDI can be artificially induced as described generally, e.g., in Sambrook et al (1989). Examples of suitable media are given in U.S. Pat. Nos. 5,304,472 and 5,342,763.

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5–9, depending mainly on the host organism. Optionally the culture medium may contain one or more reducing agents selected from the group consisting of glutathione, cysteine, cystamine, thioglycollate, dithioerythritol, dithiothreitol and dithioerythritol. Preferably, the bacteria arc not cultured so as to over-express nucleic acid encoding the heat-shock transcription factor, RpoH.

For induction, typically the cells are cultured until a certain optical density is achieved, e.g., a $A_{550}$ of about 60–80, at which point induction is initiated (e.g., by addition of an inducer, by depletion of a medium component, etc.), to induce expression of the pdi gene. When the optical density reaches a higher amount, e.g., a $A_{550}$ of about 80–100, induction of the second promoter for the heterologous polypeptide is effected.

Gene expression may be measured in a sample directly, for example, by conventional northern blotting to quantitate the transcription of mRNA (Thomas, 1980). Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like.

Procedures for observing whether an expressed or over-expressed gene product is secreted are readily available to the skilled practitioner. Once the culture medium is separated from the host cells, for example, by centrifugation or filtration, the gene product can then be detected in the cell-free culture medium by taking advantage of known properties characteristic of the gene product. Such properties can include the distinct immunological, enzymatic, or physical properties of the gene product.

For example, if an over-expressed gene product has a unique enzyme activity, an assay for that activity can be performed on the culture medium used by the host cells. Moreover, when antibodies reactive against a given gene product are available, such antibodies can be used to detect the gene product in any known immunological assay (e.g., as in Harlow and Lane, 1988).

The secreted gene product can also be detected using tests that distinguish polypeptides on the basis of characteristic physical properties such as molecular weight. To detect the physical properties of the gene product, all polypeptides newly synthesized by the host cell can be labeled, e.g., with a radioisotope. Common radioisotopes that can be used to label polypeptides synthesized within a host cell include tritium ($^3H$), carbon-14 ($^{14}C$), sulfur-35 ($^{35}S$), and the like. For example, the host cell can be grown in $^{35}S$-methionine or $^{35}S$-cysteine medium, and a significant amount of the $^{35}S$ label will be preferentially incorporated into any newly synthesized polypeptide, including the over-expressed heterologous polypeptide. The $^{35}S$-containing culture medium is then removed and the cells are washed and placed in fresh non-radioactive culture medium. After the cells are maintained in the fresh medium for a time and under conditions sufficient to allow secretion of the $^{35}S$-radiolabeled expressed heterologous polypeptide, the culture medium is collected and separated from the host cells. The molecular weight of the secreted, labeled polypeptide in the culture medium can then be determined by known procedures, e.g., polyacrylamide gel electrophoresis. Such procedures, and/or other procedures for detecting secreted gene products, are provided in Goeddel (1990), and Sambrook et al. (1989).

For secretion of an expressed or over-expressed gene product, the host cell is cultured under conditions sufficient for secretion of the gene product. Such conditions include, e.g., temperature, nutrient, and cell density conditions that permit secretion by the cell. Moreover, such conditions are those under which the cell can perform basic cellular functions of transcription, translation, and passage of proteins from one cellular compartment to another, as are known to those skilled in the art.

In practicing the process of this invention, the yield of total polypeptide is generally increased, while yield of insoluble polypeptide is not changed or is decreased, i.e., yield of soluble polypeptide is increased.

The polypeptide of interest is recovered from the periplasm or culture medium as a secreted soluble polypeptide. It is often preferred to purify the polypeptide of interest from recombinant cell proteins or polypeptides and from PDI to obtain preparations that are substantially homogeneous as to the polypeptide of interest. As a first step, the culture medium or lysate is centrifuged to remove particulate cell debris. The membrane and soluble protein fractions may then be separated if necessary. The polypeptide may then be purified from the soluble protein fraction and from the membrane fraction of the culture lysate, depending on whether the polypeptide is membrane associated or, more preferably, completely soluble in the periplasm or culture supernatant. The polypeptide thereafter may be further solubilized and/or refolded, if necessary, and purified from contaminant soluble proteins and polypeptides.

The types of phase-forming species to employ herein depend on many factors, including the type of polypeptide and the ingredients in the fermentation broth being treated. The species must be selected so that the polypeptide does not precipitate and one phase is more hydrophobic than the other phase so that the polypeptide will be located in the more hydrophobic phase and the biomass solids and nucleic acids will settle to the less hydrophobic phase.

The phase-forming species may be a combination of agents, including polymer combinations (polymer-polymer), polymer-salt combinations, solvent-salt, and polymer-solvent combinations. Suitable polymers are both highly hydrophilic polymers and less hydrophilic polymers, i.e., any phase-forming polymers that are known in the art. Examples include polyethylene glycol or derivatives thereof, including various molecular weights of PEG such as PEG 4000, PEG 6000, and PEG 8000, derivatives of PEG described, for example, in Grunfeld et al. (1992), polyvinylpyrrolidone (PVP), in a preferable molecular weight range of about 36,000 to 360,000, starches such as dextran (e.g., dextran 70 and 500), dextrins, and maltodextrins (preferable molecular weight between about 600 and 5,000), sucrose, and FICOLL-400™ polymer (a copolymer of sucrose and epichlorohydrin). The preferred polymer herein is polyethylene glycol, polypropylene glycol, polyvinylpyrrolidone, or a polysaccharide such as a dextran. The most preferred polymer herein is PEG of different molecular weights or a PEG-polypropylene glycol combination or copolymer.

Examples of suitable organic solvents include ethylene glycol, glycerol, dimethyl sulfoxide, polyvinylalcohol, dimethylformamide, dioxane, and alcohols such as methanol, ethanol, and 2-propanol. Such solvents are such that, when added to aqueous solution, they increase the hydrophobicity of the solution.

The salts can be inorganic or organic and preferably do not act to precipitate the polypeptide. Salts containing transition elements are not preferred as they tend to precipitate the polypeptide. Anions are selected that have the potential for forming aqueous multiple-phase systems. Examples include ammonium sulfate, sodium dibasic phosphate, sodium sulfate, ammonium phosphate, potassium citrate, magnesium phosphate, sodium phosphate, calcium phosphate, potassium phosphate, potassium sulfate, magnesium sulfate, calcium sulfate, sodium citrate, manganese sulfate, manganese phosphate, etc. Types of salts that are useful in forming bi-phasic aqueous systems are evaluated more fully by Zaslavskii et al. (1988). Preferred salts herein are sulfates, phosphates, or citrates and are alkali or alkaline earth metals. More preferred are sulfates and citrates, and most preferred are sulfates since there are fewer pH limitations with sulfates. The most preferred salts herein are sodium sulfate and sodium citrate.

The amounts of phase-forming species to add to the polypeptide of interest to obtain a satisfactory multiple-phase system are those known in the art. The amount of phase-forming species added to the polypeptide will depend on such factors as, for example, the amount of chaotropic agent and reducing agent, if any, already present in the fermentation broth, the nature of the cell culture media, the type of cells used in the fermentation, the type of polypeptide being treated, whether the polypeptide will be recovered from the lower or upper phase, and the type(s) of phase-forming species being added. The general concentration of polymer employed is about 5% (w/w) up to the limit of solubility for the polymer and the concentration of salt employed is about 3% (w/w) up to the limit of solubility for the salt, depending on the size of the phase-volume ratio needed. The phase-volume ratio must be sufficient to accommodate the biomass solids. The types and amounts of phase-forming species that are effective can be determined by phase diagrams and by evaluating the final result, i.e., the degree of purity and the yield of the polypeptide of interest. If the phase-forming species are a polymer-salt combination, preferably the concentration of salt added is about 4–15% (wt./wt.) and the concentration of polymer is 5–18% (wt./wt.) so that the desired polypeptide will be in an opposite phase from that in which the biomass solids and nucleic acids are present.

If the system desired is one where the polypeptide is distributed in the top phase and the biomass solids and nucleic acids are in the bottom phase, then there is a window of concentrations of phase-forming species. When higher amounts of chaotropic agent are added to maintain solubilization, the higher the amount of phase-forming species required. However, a high concentration of all these reagents will increase the density of the solution. A high density will cause the biomass solids to settle less readily. An overly high density will cause biomass solids to float on the surface. Hence, the concentrations of chaotropic agent and phase-forming species must be sufficiently high to maintain a fully solubilized polypeptide, but low enough to allow the biomass solids to sediment to the opposite (lower) phase.

If the polypeptide is to be recovered in the upper phase, typically the salt concentration will be about 4–7% (wt./wt.) and the polymer concentration will be about 12–18% (wt./wt.), depending, e.g., on the type of salt, polymer, and polypeptide. If an organic solvent is added as a phase-forming species, such as ethanol, it is preferably added in a concentration of about 10 to 30% (vol./vol.) of the solution, depending, e.g., on the type of polypeptide and alcohol and if any other phase-forming species is present, preferably at a concentration of about 20% (vol./vol.).

The exact conditions for contacting the cell culture with the various reagents will depend on, e.g., the pH of the buffer, the types of phase-forming reagents, and the types and concentrations of polypeptide and chaotropic and reducing agents. The reaction temperature is generally about 20 to about 40° C., more preferably room temperature. The contacting step will generally be carried out for at least about 30 min., preferably about 30 min. to about 12 hr depending on whether side-reactions will occur, more preferably about 30 min. to about 8 hr, and most preferably about 30 min. to about 1.5 hr.

Once the multiple-phase system is established, one phase will be enriched in the polypeptide and depleted in the disrupted particles and cells comprising the biomass solids and nucleic acids. In a two-phase system, preferably the top phase is enriched in the polypeptide whereas the bottom phase is enriched in the disrupted particles and cells. The polypeptide can be easily recovered by separation of the phases. This recovery step may be accomplished by decanting the upper phase, by draining the lower phase, or by centrifugation. The polypeptide can then be isolated from the phase in which it is contained by changing the pH of the phase so as to precipitate the polypeptide or by adding a suitable solvent, whereupon the precipitated polypeptide is suitably recovered by centrifugation or filtration or as a slurry. Alternatively, the polypeptide can be recovered from the polymer-containing phase by re-extraction by addition of a suitable polymer, salt, or solvent. The PDI protein may also be separated from the recombinant tPA or PTI polypeptide at this stage.

Once obtained from the liquid phase of the multiple-phase system, or at a later stage of purification, the polypeptide may be suitably stored in an appropriate buffer. The buffer can be any buffer known to those of skill in the art to preserve the biological activity and integrity of the isolated recombinant polypeptide. Such buffers include those listed below in Section 5, or alternatively, CAPSO, glycine, CAPS, MOPS, HEPES, etc. may be employed preferably at a pH of from between about pH 6 and pH 11, particularly at a concentration of about 20 mM. The polypeptide may be diluted with the buffer, or alternatively, the polypeptide may be dialyzed against fresh buffer.

5. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 EXAMPLE 1—PRODUCTION OF BPTI IN E. COLI HOST CELLS

The present work shows that rat rPDI expressed in the E. coli periplasmic space is able to catalyze the formation of disulfide bonds in bacterial proteins, and to complement several of the phenotypes of dsbA mutants. Expression of rPDI in the E. coli periplasm enhances expression of the recombinant multi-disulfide pancreatic trypsin inhibitor, BPTI.

5.1.1 MATERIALS AND METHODS 5.1.1.1 BACTERIAL STRAINS AND PLASMIDS

The E. coli K12 strains used were JCB570 [MC1000 phoR zih12::Tn10], JCB571 [JCB570 dsbA::kan1], JCB789 [JCB570 dsbB::kan], JCB758 [JCB570 dsbA::kan dsbB::kan], JCB502[(ID69), lacZ::Tn10 (Tet$^S$ by fusaric acid)] and JCB572 [JCB502 dsbA::kan1] (Bardwell et al., 1991; Bardwell et al., 1993). The last two strains contained F'[proAB, lacIq, lacZ ΔM15, Tn10]. pTI103 contains the OmpA leader-BPTI gene fusion and has been described previously (Goldenberg, 1988). pLPPsOmpArPDI contains the gene for the mature rat PDI, fused to the OmpA signal sequence, under the control of the lpp-lac promoter (De Sutter et al., 1994). pACYCBPTI contains the OmpA leader-BPTI gene fusion and the origin of replication of pACYC184.

5.1.1.2 GENERAL METHODS

Unless otherwise specified, cells were grown at 37° C. in M9 minimal salts media, adjusted to pH 7.0, and supplemented with 0.2% glucose, and 0.2% casein. For labeling studies, cultures were supplemented with 50 μg/ml L-amino acids [except cysteine and methionine] instead of casein. Amp (50 μg/ml) and/or chloramphenicol (Cam) (40 μg/ml) was added as required. In the BPTI production studies, 100 μg/ml Amp and 170 μg/ml Cam were used to maintain the co-transformants.

Fractionation by osmotic shock was carried out essentially as described by Neu and Heppel (1965). Sensitivity to filamentous phages was tested by diluting overnight cultures, grown without IPTG, to an $OD_{600\ nm}$=0.005, followed by infection with phage JB4 (a $Cam^R$, M13 derivative). Subsequently the cells were plated on LB with 0.2% glucose and 20 μg/ml Cam. Conjugation studies using SF103 (F$^-$ ΔlacX74 galE galK thi rpsL(strA) Δ phoA(PvuII) ptr-32::ΩCam$^R$) as the recipient strain were conducted as described (Silhavy et al., 1983). Rabbit polyclonal antisera against native BPTI (Boehringer-Mannheim) and rPDI were prepared using standard protocols (Ausubel et al., 1989).

5.1.1.3 PULSE-CHASE STUDIES, IMMUNOPRECIPITATION AND ELECTROPHORESIS

For monitoring the oxidative state of alkaline phosphatase and OmpA, mid-exponential phase cells were labeled with 100 μCi/ml TRANS $^{35}$S LABEL (ICN Biomedicals Inc.) for 45 sec and chased with 20 mM methionine and 3 mM cysteine. Samples (1 ml) were withdrawn at various times and added to trichloroacetic acid on ice at a final concentration of 10%. The protein pellets obtained by centrifugation at 12,000×g for 10 min were resuspended in 0.5 ml of 100 mM Tris-HCl (pH 9.0), 1.5% SDS, 5 mM EDTA and 35 mM iodoacetamide. Samples were then diluted 4-fold in immunoprecipitation buffer (10 mM Tris-HCl, pH 8.0, 0.1% TRITON X-100®, 0.14 M NaCl, and 0.025% NaN$_3$) and immunoprecipitated with antisera to alkaline phosphatase (from 5' Prime 3' Prime, Boulder, Colo.) and OmpA as previously described (Ostermeier and Georgiou, 1994). Oxidized and reduced proteins were resolved by SDS-PAGE in 20 cm non-reducing gels essentially as described (Pollitt and Zalkin, 1983). Pulse-chase studies for following the kinetics of folding of BPTI were carried out as previously described (Ostermeier and Georgiou, 1994) except the chase contained 3 mM cysteine.

5.1.1.4 DETECTION OF BPTI BY ELISA

Cells were induced with 0.1 mM IPTG at $OD_{600\ nm}$=0.3–0.35, and, for some samples, GSH and/or GSSG was added twenty min later at the concentrations indicated. Five hours after induction, samples were frozen at −70° C., then thawed to 4° C., lysed by French press (20,000 psi) and fractionated into insoluble and soluble fractions by centrifugation at 12,000×g for 10 min. The protein concentration of the soluble fraction was measured by the Bio-Rad Protein Assay (Bio-Rad, Richmond, Calif.). Next, 100 μl of soluble protein diluted to a concentration of 2.5 μg protein/ml in ELISA coating buffer (32 mM Na$_2$CO$_3$/68 mM NaHCO$_3$) was added to 96-well plates. After incubation overnight at 4° C., the wells were washed three times with washing buffer (0.5% Tween-20® in phosphate buffer saline) and three times with ddH$_2$O, blocked with 200 μl of 2% bovine serum albumin (Boehringer Mannheim) in phosphate buffered saline for 1 hour at 37° C., and washed again.

Subsequently, 100 μl/well of BPTI antisera (diluted 1:1000 in phosphate buffer saline with 0.05% Tween-20® and 0.25% bovine serum albumin) was added to the plate and incubated for 1 hr at 37° C. The plate was then washed again as before and 100 μl of goat anti-rabbit horseradish peroxidase conjugate (diluted 1:1000 in phosphate buffer saline with 0.05% Tween-20® and 0.25% bovine serum albumin) was added to each well. After 30 min at 37° C. and a final wash, 100 μl of Peroxidase Substrate ABTS (Bio-Rad) was added. Developing was stopped with 100 μl 2% oxalic acid after 5 min. and the $A_{410}$ was measured on a MR300 MicroElisa Reader (Dynatech Laboratories Inc., Chantilly, Va.). The soluble fraction of cells without plasmid was spiked with known amounts of BPTI and used as standards.

5.1.1.5 AFFINITY PRECIPITATION OF BPTI WITH TRYPSIN-AGAROSE

Soluble fractions from 1.5 ml culture volume were mixed with 1.5 ml of 50 mM Tris HCl (pH 8.0) buffer and 12.5 μl trypsin-agarose beads (Sigma, 20 units/ml) and incubated on a rotator at 4° C. Subsequently, the beads were resuspended in SDS loading buffer, boiled for 5 min, centrifuged, and the soluble fractions were loaded onto 16% Tricine SDS-PAGE (Novex, San Diego, Calif.). Electrophoresis was carried out under reducing conditions. The proteins were then transferred to a PVDF membrane for 45 min at 2.5 mA/cm$^2$ using the MILLIBLOT-GRAPHITE ELECTROBLOTTER System (Millipore, Bedford, Mass.) and immunologically detected with the anti-BPTI primary antibody (1:1000 dilution) followed by horseradish peroxidase-conjugated goat anti-rabbit IgG (1:3000 dilution) (Bio-Rad, Hercules, Calif.) (Ausubel et al., 1989).

5.1.2 RESULTS

The gene encoding the complete sequence of mature rat PDI has been fused to the bacterial OmpA leader peptide and expressed from the strong lac-lpp promoter (De Sutter et al., 1994). Even in the absence of the inducer IPTG, a 55-kDa band corresponding to the mature rPDI is readily visible in SDS-PAGE gels of the osmotic shock fraction of E. coli (FIG. 1) and is the only band detected by Western blot analysis using rPDI-specific sera. Upon induction with 0.5 mM IPTG, rPDI was overexpressed and became the most prominent protein in the periplasmic space. In addition to the intact rPDI monomer, a lower molecular weight product, designated rPDIf, was evident in induced but not in uninduced cultures (FIG. 1). De Sutter et al. (1994) have shown that rPDIf corresponds to a polypeptide synthesized from an internal translation initiation codon in the rPDI gene. Although rPDIf is found predominantly in the spheroplast fraction, a portion is released by osmotic shock, as is evident from FIG. 1. Western blotting of samples from induced cultures also revealed several minor lower molecular weight species, presumably degradation products. The level of expression was identical in both the dsbA mutant strain JCB571 and in the isogenic control strain JCB570. Furthermore, western blot demonstrated that rPDI production was not substantially affected by the dsba, dsbB or dsbAdsbB mutations under either induced or uninduced conditions. This is in contrast to other disulfide bond-containing secreted proteins such as alkaline phosphatase, β-lactamase, urokinase and BPTI (Bardwell, 1994; Ostermeier and Georgiou, 1994). The production of these proteins is substantially reduced in dsbA and dsbB mutants, presumably because inefficient formation of disulfide bonds results in increased susceptibility to proteolytic degradation.

While dsbA is not essential for cell viability, null mutants exhibit pleiotropic phenotypes including resistance to filamentous phages, impaired motility and conjugation, poor growth in minimal media and formation of mucoid colonies when grown with sub-lethal concentrations of antibiotics (Bardwell, 1994; Bardwell et al., 1991). As shown in FIG.

2A and FIG. 2B, transformation with pLPPsOmpArPDI resulted in complementation of several dshA phenotypes. Basal expression of rPDI in cells grown without inducer was sufficient to restore conjugation competence and sensitivity to f1 phage to about 20% and 35% of the level in the parental strain, respectively. Expression of rPDI also restored the growth rate of dsbA⁻ cells in minimal media to that of dsbA⁺ cells (FIG. 2B). Complementation of the dsbA phenotypes is not merely due to the expression of a heterologous secreted protein since it was not observed in cells producing preOmpA-BPTI which is also exported in the *E. coli* periplasmic space via the OmpA leader peptide and, like rPDI, contains six cysteines. It should be noted that in these studies, cells were not induced with IPTG because (a) rPDI was already expressed at significant levels without induction and (b) the overproduction of rPDI in induced cultures was found to negatively affect the efficiency of conjugation in wild type cells.

In some genetic backgrounds a null dsbA allele confers sensitivity to DTT (Missiakas et al., 1993). However, the growth of JCB570 and JCB571 were similarly affected by the presence of reduced DTT or GSH in both rich and minimal media. Thus, in the JCB570 genetic background, it was not possible to determine whether the expression of rPDI affects the sensitivity of dsbA⁻ cells to reducing agents.

The ability of rPDI to complement the phenotypes of dsbA null mutants suggested that it must be able to catalyze the formation of disulfide bonds in the periplasmic space. Direct evidence for the function of rPDI in vivo was obtained by examining the kinetics of oxidation of two bacterial exported proteins, alkaline phosphatase and OmpA. Cultures were radiolabeled with 100 $\mu$Ci/ml Trans $^{35}$Label for 45 sec and then samples were added to iodoacetamide at different times to carboxymethylate free cysteine residues. Subsequently, reduced and oxidized alkaline phosphatase were resolved electrophoretically in 20 cm polyacrylamide gels. The formation of disulfide bonds in dsbA⁺ cells was very rapid and was largely completed within one min, whereas in dsbA⁻ cells, no oxidized alkaline phosphatase was detectable even after 10 min (FIG. 3A). However, in cells expressing basal levels of rPDI, the formation of disulfide bonds was restored and oxidized alkaline phosphatase was the only species detectable after 10 min of chase. Transformation with a control plasmid (pTI103) did not have any effect on the oxidation state of alkaline phosphatase. Similar results were observed with the oxidation of the outer membrane protein OmpA which contains a single disulfide bond in the putative C-terminal periplasmic domain.

For PDI to be functional as a direct oxidase, its active site must be regenerated through disulfide exchange with an appropriate donor/acceptor. Whereas in the ER the redox state of PDI is determined by the ratio of reduced to oxidized glutathione, there is no evidence for an analogous low molecular weight redox buffer in the periplasmic space. In *E. coli*, the reoxidation of DsbA is thought to be mediated by DsbB, a cytoplasmic membrane protein that contains at least four, and possibly five, cysteines within two periplasmic exposed loops (Guilhot et al., 1995; Bardwell et al., 1993; Missiakas et al., 1993; Dailey and Berg, 1993; Jander et al., 1994). dsbB mutants exhibit a defect in disulfide bond formation, though not as severe as dsbA mutants. To determine whether the active state of rPDI may also be dependent on DsbB, the oxidation of alkaline phosphatase was monitored in dsbB mutants transformed with pLPPs OmpArPDI. In dsbB mutants less than 30% of the alkaline phosphatase was found in the oxidized form even after 10 min post-chase (FIG. 3B). Expression of rPDI was largely unable to rescue the formation of oxidized alkaline phosphatase as only 50% of the alkaline phosphatase was oxidized after ten min. Furthermore, no oxidized protein was detected in dsbA dsbB double mutants with or without pLPPsOmpArPDI. Further evidence of rPDI's dependence on DsbB came from studying the production of the heterologous protein BPTI. As discussed in greater detail below, although rPDI could rescue the formation of BPTI in dsbA mutants, rPDI could not rescue the formation of BPTI in dsbB mutants. Thus, the catalysis of disulfide formation by rPDI in *E. coli* is dependent on a functional dsbB gene.

In dsbB mutants, but not in dsbA mutants or in wild type cells, the expression of rPDI appeared to mildly interfere with the processing of the leader peptide as evidenced by the presence of a band corresponding to the alkaline phosphatase precursor one min after the chase. A faint band corresponding to the precursor was also evident even after ten min (FIG. 3B).

Under physiological conditions, the periplasmic space of *E. coli* is rather poor in disulfide isomerase activity, a function that is thought to be mediated primarily by DsbC (Bardwell, 1994). Since a major role of PDI in the endoplasmic reticulum appears to be the catalysis of disulfide bond isomerization (Bardwell and Beckwith, 1993; Wittrup, 1995), it was reasoned that the presence of rPDI in the *E. coli* periplasm may facilitate the expression of heterologous proteins whose folding requires the rearrangement of disulfide bonds. The rate limiting step in the in vitro folding of BPTI (Creighton, 1992; Weissman and Kim, 1992; Goldenberg, 1992). In vitro, the presence of PDI modestly increases the rate of formation of two disulfide intermediates but greatly increases their rate of intramolecular rearrangement (Weissman and Kim, 1993) and possibly direct oxidation (Creighton et al., 1980). Expression of secreted BPTI in *E. coli* results in low levels of native protein and is accompanied by the accumulation of two disulfide intermediates in the periplasmic space (Ostermeier and Georgiou, 1994). To measure the effect of rPDI on BPTI expression, cells were co-transformed with pLPPsOmpArPDI and pACYCBPTI, a compatible plasmid carrying the BPTI gene. The cells were grown in minimal media supplemented with chloramphenicol and Amp to maintain both plasmids. Because the standard assay for BPTI, which is based on trypsin inhibition, is not very sensitive and suffers in part from interference from endogenous proteases and trypsin inhibitors, BPTI was quantified by ELISA using a primary polyclonal antibody raised against native BPTI.

Coexpression of rPDI in wild type cells resulted in a six fold increase in BPTI in the absence of glutathione and a fifteen fold increase in its presence (FIG. 4). The increased yield with rPDI coexpression was not due to a higher rate of BPTI synthesis. If anything, co-expression of rPDI resulted in a slightly lower rate of BPTI synthesis as determined by radiolabeling studies. This slight reduction in the rate of protein synthesis cannot account for the increased efficiency of native BPTI formation since in the absence of rPDI, BPTI production was not found to improve in cells where the synthesis of BPTI was reduced by lowering the amount of inducer, IPTG.

To confirm that the increased level of BPTI detected by ELISA was due to the production of native protein, BPTI was affinity precipitated with trypsin immobilized on agarose beads and detected by Western blotting. The interaction between trypsin and native BPTI is exceedingly strong (dissociation constant $6\times10^{-14}$ M) and the complex is stable for weeks at 4° C. (Vincent and Lazdunski, 1972). Reduced, carboxymethylated BPTI does not bind to trypsin. Coomassie staining of trypsin-precipitated samples from wild type cells not bearing any plasmid detected a band at approximately 16-kDa, the molecular weight of the E. coli trypsin inhibitor ecotin which has no homology with BPTI (McGrath et al., 1991). Several other faint bands were also visible, but none of these bands crossreacted with anti-BPTI sera on Western blots (FIG. 5A, lane 2). When such E. coli extracts were spiked with high levels of purified BPTI and trypsin affinity precipitated more than one band was detected by Western blotting (FIG. 5A and FIG. 5B). At lower protein loading, however, only a single band was visible.

Western blots showing the level of BPTI in wild type, dsbA and dsbB cultures, with or without co-expression of rPDI, and in the presence of various amounts of reduced or oxidized glutathione are shown in FIG. 5A and FIG. 5B. These studies confirmed that coexpression of rPDI increases the level of native BPTI production several fold and that production could be further enhanced by supplementing the growth media with moderate amounts of GSH. In the absence of rPDI co-expression, glutathione alone did not increase the production of BPTI. A modest increase was somewhat variable. The presence of high concentrations of GSH (25 mM) was found to adversely affect the production of BPTI both with and without rPDI co-expression.

Cells lacking a functional DsbA or DsbB were found to be completely impaired in BPTI production, a deficiency which could not be alleviated by the addition of reduced or oxidized glutathione or a mixture thereof (FIG. 5B). Although exogenous oxidized glutathione can partially oxidize DsbA and thus complement some of the phenotypes of dsbB mutants, in this case it was not sufficient to rescue BPTI production. Coexpression of rPDI was able to restore BPTI production in dsbA mutants but not dsbB mutants, further illustrating that rPDI complements the dsbA mutation and that rPDI's oxidase activity is dependent on a functional DsbB protein. In dsbB mutants, BPTI was detected only in cells coexpressing rPDI and supplemented with 10 mM oxidized glutathione. The addition of 10 mM cystamine to cultures expressing rPDI could also complement the dsbB mutation. Since PDI has been shown to have a specificity for glutathione in forming the mixed disulfide in dithiol-mediated oxidation (Darby et al., 1994), these results suggest that the likely role of the added dithiols is to oxidize the active site of rPDI which then carries out direct oxidation of the protein substrate. Finally, is should be mentioned that 10 mM oxidized DTT, which is a much weaker oxidizer that GSSG or cystamine, could not rescue BPTI dsbB mutants coexpressing rPDI.

In mutant cells, particularly dsbB mutants, the induction of rPDI resulted in the accumulation of two higher molecular weight species, one of which migrated with an electrophoretic mobility identical to the BPTI precursor. Both of these species were recognized by an antiserum against BPTI obtained from a different laboratory and are unlikely to represent crossreacting E. coli proteins. As was discussed above, the expression of rPDI in dsbB mutants results in some retardation of precursor processing. Therefore, it is possible that the higher molecular weight species detected in the dsbB mutants where rPDI was overproduced correspond to preOmpA-BPTI species. Such preOmpA-BPTI species must contain at least some of the native disulfides since otherwise they could not have been bound by the immobilized trypsin.

To elucidate the role of PDI in the folding of BPTI, the kinetics of folding were monitored in pulse chase studies where folding intermediates were trapped by blocking free cysteines with iodoacetamide and separated by non-reducing gel electrophoresis. In the electrophoretic system used here, all two-disulfide intermediates (designated as *) are well resolved from the native protein and from other folding species (Ostermeier and Georgiou, 1994). Without coexpressing rPDI, these two disulfide intermediates accumulate during folding, and the rate limiting step in the formation of native protein is their isomerization. In cells expressing rPDI, two disulfide intermediates were still observed to accumulate (FIG. 6). Furthermore, when reduced glutathione is added to the cells two disulfide intermediates accumulated to an even greater extent. In this case over 50% of the BPTI is found as two-disulfide intermediate species after 20 min of chase. It appears that under these conditions rPDI in the E. coli periplasm did not have a noticeable effect on the rearrangement and/or direct oxidation of kinetically trapped two-disulfide intermediates. The exact fate of the * band is not known at present, but it must be degraded and/or eventually fold to native protein. When lysates of wild type cells or dsbA mutants expressing rPDI (which had been labeled with $^{14}$C-L-amino acids for 5 hours and protein free cysteines blocked with 100 mM iodoacetamide) were immunoprecipitated and resolved on non-reducing Reisfeld-Urea gels, only native BPTI with three disulfides was found to be present.

In cells co-expressing rPDI the half-life for the formation of the native protein was approximately 6–7 min independent of whether GSH/GSSG had been added. This is experimentally indistinguishable from the rate of BPTI folding without rPDI (Ostermeier and Georgiou, 1994) and consistent with rPDI not having an effect on the rate limiting step: disulfide isomerization. For comparison, the folding of BPTI in eukaryotic microsomes, which are rich in PDI, can occur with a half life of less than one min at 30° C. and is accompanied by relatively little accumulation of two-disulfide intermediates, depending on the redox conditions employed (Creighton et al., 1993).

Rat protein disulfide isomerase is expressed at a high level in the E. coli periplasm even in dsbA mutants. Besides restoring normal growth in minimal media, expression of rPDI restores conjugation competence and sensitivity to filamentous phages. These phenotypes are dependent on the presence of correctly assembled F pili, a process which is impaired when disulfide bond formation is compromised in dsbA mutants. Ostensibly, rPDI restores pili assembly by facilitating disulfide bond formation. Indeed, rPDI could catalyze the oxidation of native E. coli proteins such as alkaline phosphatase and OmpA in cells lacking DsbA, albeit at a rate somewhat slower than DsbA's.

Although these results strongly suggest that rPDI functions as a cysteine oxidase in the periplasmic space of gram-negative bacteria, another explanation is that rPDI does not function catalytically, but instead it somehow induces the synthesis of other E coli proteins that are responsible for disulfide bond formation. For example, Missiakas et al. (1994) have shown that overexpression of DsbC can complement dsbA mutations and it may be possible that the phenomenon observed arose indirectly due to the induction of DsbC. This is not the case for the following reasons: (a) The oxidation of alkaline phosphatase in dsbA mutants expressing rPDI is dependent on DsbB. However, high levels of DsbC in fact complement dsbB mutations (Missiakas et al, 1994). Thus, the function of rPDI cannot merely be due to the induction of DsbC since then it would not be expected to be dsbB dependent. (b) As shown in FIG. 5A and FIG. 5B and discussed further below, expression of rPDI is essential for the formation of native BPTI in dsbA mutants. In the absence of rPDI, no BPTI is formed in dsbA mutants even when the cells are grown with a wide range of concentrations of exogenous thiols and disulfides. Thus it cannot be argued that rPDI simply changes the redox state of the periplasm; rather its enzymatic activity per se catalyzes the formation of disulfide bonds in BPTI.

Given the presence of millimolar concentrations of glutathione in the ER (Hwang et al., 1992) and PDI's specificity for glutathione (Darby et al., 1994) it appears that in eukaryotes the active state of PDI is maintained by glutathione. Since there is no evidence for the presence of glutathione or other low molecular weight thiols in the bacterial periplasmic space (Wülfing and Plückthun, 1994), it is reasonable to assume that for rPDI to be functional in the periplasm, it must be able to interact directly with a component of the prokaryotic disulfide forming machinery. Indeed, the rPDI-mediated formation of disulfide bonds in alkaline phosphatase and BPTI was found to be dependent on DsbB. This is interesting given that rPDI, apart from its thioredoxin active site, shows little homology to DsbA or to other bacterial proteins. It may be that the active site of rPDI, whose three dimensional structure has not yet been solved, conforms to the thioredoxin fold as is the case with DsbA. If the active sites of the two proteins are structurally similar, then it is reasonable to expect that a protein such as DsbB, which normally interacts with DsbA, may also be able to interact with rPDI. Alternatively, rPDI's dependence on DsbB may be an indirect effect.

In catalytic amounts and in the presence of glutathione or other small molecular weight thiols, PDI primarily catalyzes the formation of mixed disulfides with model peptide substrates (Darby et al., 1994). However, the lack of a periplasmic low molecular weight redox couple in bacteria and rPDI's dependence on DsbB implies that rPDI catalyzes disulfide bond formation by direct transfer of its own disulfide bonds to protein substrates. Direct formation of disulfide bonds form PDI to reduced proteins has been observed in vitro with stoichiometric quantities of the enzyme and in the absence of other oxidants (Darby et al., 1994; Zapun and Creighton, 1994). It should be noted that DsbA also normally transfers its disulfide bond directly to reduced protein substrates (Zapun and Creighton, 1994), but unlike with PDI, this reaction is not enhanced by the addition of glutathione redox buffers (Joly and Swartz, 1994).

Gram-negative bacterial proteins fold faster under very oxidizing conditions. For example, the optimal rate for folding of alkaline phosphatase in vitro occurs in 6 mM GSSG and proceeds at 50% the maximal rate in 30 mM GSSG (Walker and Gilbert, 1994). Accordingly, there is evidence that the periplasmic space is indeed highly oxidizing environment. Most, if not all, of the DsbA molecules have been shown to be in the oxidized form in the periplasm of wild type cells (Kishigami et al., 1995). The highly oxidized state of the periplasm can in part explain why eukaryotic proteins containing multiple disulfides are often poorly expressed. In the endoplasmic reticulum, these proteins normally fold in a relatively reduced environment which affords the opportunity for reduction of incorrect disulfides and disulfide rearrangement, processes catalyzed by PDI (Freedman et al., 1994; Wittrup, 1995). Disulfide bond isomerization is likely to be relatively unimportant to E. coli as periplasmic and outer membrane proteins with more than two disulfides are rare (Joly and Swartz, 1994).

For rPDI to be efficient in the oxidation of alkaline phosphatase in dsbA mutants, it must provide a redox environment comparable to that afforded by DsbA, an equivalent $[GSH]^2/[GSSG]$ equilibrium constant of around 20 μM (Walker and Gilbert, 1994). The redox potential of PDI at near physiological pH is equivalent to $[GSH]^2/[GSSG]$ of around 40–80 μM. Thus, a significant fraction, if not the majority, of the rPDI molecules in the periplasm must be present in the oxidized form in order to effectively facilitate disulfide formation. This is quite different from the endoplasmic reticulum where the redox state is believed to be $[GSH]^2/[GSSG]$=0.5–3.3 mM and PDI would be present almost exclusively in reduced form (Hwang et al., 1992).

To examine whether rPDI can catalyze disulfide bond isomerization in the periplasm, the oxidative folding of BPTI was monitored. BPTI is a three disulfide protease inhibitor which is very poorly expressed in E. coil and whose in vitro folding pathway involves disulfide rearrangement as shown in Scheme 1 (Goldenberg, 1992).

PDI has been shown to catalyze virtually all of the steps in the in vitro folding pathway of BPTI (Weissman and Kim, 1993; Creighton et al., 1980). In the presence of catalytic amounts of protein disulfide isomerase and a suitable redox buffer, the rate of formation of N' and N* from reduced protein is increased by about three-fold whereas the subsequent folding of these two kinetically trapped intermediates to N is accelerated by more than 3,000 fold (Weissman and Kim, 1993) resulting in a dramatic decrease in the amount of two disulfide intermediates observed during folding. Catalysis also appears to occur in vivo as evidenced by the fact that relatively small amounts of two disulfide intermediates were detected during the folding of BPTI in microsomes (Creighton et al., 1993).

Co-expression of rPDI in wild type E. coli increased the steady-state level of BPTI by fifteen fold in the presence of glutathione and six fold in its absence. However, pulse chase studies revealed that the presence of rPDI does not decrease the accumulation of two-disulfide intermediates. In fact, in the presence of glutathione, two disulfide intermediates accumulated to a greater extent. Thus, in wild type E. coli, rPDI does not facilitate the isomerization of N' and N* to $N^{SH,SH}$ anymore than the formation of N' and N*.

In wild type cells, rPDI does not function as an appreciable isomerase or direct oxidant of the final disulfide in the two disulfide intermediates, the rate limiting step in folding. rPDI's apparent lack of isomerase activity in the periplasm is not surprising since evidence suggests that the active sites of rPDI in the periplasm are predominantly oxidized and therefore can only catalyze direct oxidation and not disulfide rearrangement. Attempts to improve BPTI production in vivo by making the periplasm more reducing (i.e., by adding reducing agents or by using dsb mutants) in order to elicit rPDI isomerase activity were unsuccessful, but should not be construed as evidence of an inability of rPDI to exhibit isomerase activity in the periplasm. In a more reducing periplasm, the rates of formation of the first and second disulfides in BPTI should decrease and thus the competing process of proteolysis is likely to limit the yield of correctly folded protein. It may be that the conditions for eliciting rPDI's isomerase activity leave the periplasm too reducing for any BPTI molecules to efficiently form disulfides in order to avoid proteolysis.

The increase in two disulfide intermediates with added glutathione indicates that rPDI is functioning as an oxidase that supplements DsbA in forming the two disulfide intermediates. In vitro, PDI's oxidase activity has been found to be enhanced by the addition of a redox buffer of glutathione (Darby et al., 1994).

Increased steady state levels of BPTI appear to be the result of the faster formation of two disulfide intermediates from reduced protein thus avoiding proteolysis. It is also conceivable that the chaperon-like activity of PDI may play a role in the increased levels of BPTI (Puig and Gilbert, 1994; Cai et al., 1994). Studies have determine the effect of PDI mutants with (a) only chaperon activity and (b) primarily isomerase activity on the folding of BPTI in order to further elucidate the mechanism by which its co-expression facilitates the production of multi-disulfide containing proteins.

5.2 EXAMPLE 2—METHODS FOR EXPRESSION OF TPA IN BACTERIAL CELLS

This example describes the production of soluble, active, secreted tPA in bacterial host cells by the co-expression of rPDI. Remarkably, rPDI coexpressed with rtPA significantly increases yields of tPA in the bacterial host cell.

Strains RB791 and UT5600 were co-transformed with a pACYC184 derivative vector expressing tPA from the phoA promoter and with a pBR322 recombinant vector carrying a transcriptional unit comprising the PDI gene expressed downstream from either the lac-lpp or the $P_{BAD}$ promoter (Guzman et al., 1995). The latter construct was designated pBAD-StII-tPA.

Expression of the two proteins was induced by the addition of inducers, IPTG, and arabinose, as appropriate. The cells were harvested after overnight growth and the level of tPA was determined by three methods.

In the first method, a calorimetric assay was used in which the rate of plasmin formation from plasminogen was measured (American Diagnostics, Inc.). The second method was the fibrin plate assay, in which tPA-containing cell extracts were spotted on agar plates containing fibrin and plasminogen and the zone of clearance was determined. Finally, in the third method, Western blots were performed using anti-tPA antibodies.

Active tPA was detected by both the fibrin plate assay and by the plasmin activation assay in cells co-expressing PDI. The level of active tPA protein was between about 5 and about 12 $\mu$g/L/OD$_{600\ nm}$ units of protein depending upon the strain background and particular growth conditions used. Importantly, practically no active tPA could be detected in cultures that did not co-express PDI. The co-expression of PDI increased the amount of soluble, active tPA, but did not affect the total amount (soluble+insoluble) detected by Western blotting.

5.3 EXAMPLE 3—CLONING AND EXPRESSION OF THE YEAST PDI IN E. COLI

The mature yeast PDI sequence was cloned by PCR™ amplification of the gene from an *S. cerevisiae* cDNA library (obtained from Professor K.D. Wittrup, Department of Chemical Engineering, University of Illinois, Urbana-Champaign) using the following primers: GG18: 5'ATATGAATTCTGGTTTTCGCCCAACAAGAAGCT-GTGGCC-3' (SEQ. ID NO.:1) and GG28: 5-'GGACGGAGGATCCTTACAATTCATGGTG-3' (SEQ. ID: 2).

The amplified DNA product contains a XbaI and BamHI restriction sites allowing the insertion of the gene into the expression vector pJG105 (Grayeb et al., 1984). The resulting plasmid was designated pLpplac-YPDI-I. In pLpplac-YPDI-1 the yeast PDI gene is fused in frame to the OmpA leader peptide. The ompA-ypdi gene is downstream from a strong ribosomal binding site and the IPTG-inducible lpp-lac promoter. pLpplac-YPDI-1 was transformed into a variety of *E. coli* strains including RB791, R189 and R190 (Bardwell etal., 1991). Induction of ypdi syntheses by I PTG resulted in somewhat slower growth. A band corresponding to the full length yeast PDI was detected by Western blotting using a polyclonal antiserum raised against the yeast PDI.

The pLpplac-YPDI-1 plasmid and pJG105 as a control were transformed in the dsbA$^+$ and dsbA$^-$ strains R189 and R190, respectively (FIG. 8). dsbA$^-$ mutant cells do not express alkaline phosphatase activity. Expression of the rat PDI in *E. coli* restores alkaline phosphatase activity in dsbA$^-$ mutants and a similar effect was seen in cells transformed with pLpplac-YPDI-1 and inducted with IPTG. Thus, the yeast PDI is functional when expressed in bacteria and can complement the defect in dsbA$^-$ cells. In separate studies, RB791 cells were transformed with pACYCBPTI and pLpplac-YPDI-1. Induction of BPTI and yPDI with 0.5 MM IPTG resulted in f-fold higher specific BPTI levels (per mg of total soluble protein) compared to cells that did not coexpress the yeast PDI. Importantly, unlike the case with rate PDI, the effect of years PDI could not be improved further by the additional of reductants such as glutathione.

6. REFERENCES

The following literature citations as well as those cited above are incorporated in pertinent part by reference herein for the reasons cited in the above text:

U.S. Pat. No. 4,196,265.
U.S. Pat. No. 4,431,740.
U.S. Pat. No. 4,554,101.
U.S. Pat. No. 4,652,525.
U.S. Pat. No. 4,661,453.
U.S. Pat. No. 4,683,195.
U.S. Pat. No. 4,683,202.
U.S. Pat. No. 4,965,188.
U.S. Pat. No. 5,077,392.
U.S. Pat. No. 5,176,995.
U.S. Pat. No. 5,304,472.
U.S. Pat. No. 5,336,602.
U.S. Pat. No. 5,342,763.
U.S. Pat. No. 5,508,192.
U.S. Pat. No. 60/014,950.
Eur. Pat. Appl. No. EP 510,658.
Adelman et al., DNA, 2/3:183–193,1983.
Allen and Choun, "Large unilamellar liposomes with low uptake into the reticuloendothelial system," *FEBS Lett.*, 223:42–46, 1987.
Altschul, Stephen F. et al., "Basic local alignment search tool," *J. Mol. Biol.*, 215:403–410, 1990.
Ausubel et al., *Current Protocols in Molecular Biology*, John Wiley and Sons, New York, N.Y., 1989.
Balazsovits et al., "Analysis of the effect of liposome encapsulation on the vesicant properties, acute and cardiac toxicities, and antitumor efficacy of doxorubicin, "*Cancer Chemother. Pharmacol.*, 23:81–86, 1989.
Baneyx and Georgiou, In: *Stability of Protein Pharmaceuticals: Chemical and Physical Patterns of Protein Degradation*, (Ahern and Manning, eds), Plenum Press, New York, 69–96, 1992.
Bardwell and Beckwith, Cell, 74:769–771, 1993.
Bardwell et al., *Proc. Natl. Acad. Sci. USA*, 90:1038–1042, 1993.
Bardwell et al., "A Pathway for Disulfide Bond Formation In Vivo," *Proc. Natl. Acad. Sci. USA*, 90:1–5, 1993.
Bardwell et al., "Identification of a Protein Required for Disulfide Bond Formation In Vivo," *Cell*, 67:581–589, 1991.
Bardwell, "Building Bridges: Disulphide Bond Formation in the Cell," *Mol. Microbiol.*, 14:199–205, 1994.
Baron et al., "Bailey & Scott's Diagnostic Microbiology" 9th Edition, Mosby-Year Book, Inc., St. Louis, Mo., 1994.
Bedows et al., "Kinetics of Folding and Assembly of the Human Chorionic Gonadotropin β Subunit in Transfected Chinese Hamster Ovary Cells," *J. Biol. Chem.*, 267:8880–8886, 1992.

Bolivar et al., *Gene*, 2:95, 1977.

Braakman et al., *EMBO J.*, 11:1717–1722, 1992.

Braig et al., "The Crystal Structure of the Bacterial Chaperonin GroEL at 2.8 Å" *Nature*, 371:578–586, 1994.

Brock et al., "Biology of Microorganisms" 7th Edition, Prentice Hall, Inc., Engelwood Cliffs, N.J., 1994.

Cai et al., "Chaperone-Like Activity of Protein Disulfide Isomerase in the Refolding of a Protein with no Disulfide Bonds," *J. Biol. Chem.*, 269:24550–24552, 1994.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capecchi, M. R., "High efficiency transformation by direct microinjection of DNA into cultured mammalian cells," Cell 22(2):479–488, 1980.

Carter et al., *Nucl. Acids Res.*, 12:4431–4443, 1985.

Chang et al., *Nature*, 375:615, 1978.

Chou and Fasman, "Conformational Parameters for Amino Acides in Helical, $-Sheet, and Random Coil Regions Calculated from Proteins," *Biochemistry*, 13(2):211–222, 1974b.

Chou and Fasman, "Empirical Predictions of Protein Conformation," *Ann. Rev. Biochem.*, 47:251–276, 1978b.

Chou and Fasman, "Prediction of $-Turns," *Biophys. J.*, 26:367–384, 1979.

Chou and Fasman, "Prediction of Protein Conformation," *Biochemistry*, 13(2):222–245, 1974a.

Chou and Fasman, "Prediction of the Secondary Structure of Proteins from Their Amino Acid Sequence," *Adv. Enzymol. Relat. Areas Mol. Biol.*, 47:45–148, 1978a.

Chun et al., *J. Biol. Chem.*, 268:20855–20862, 1993.

Clapp, D. W., "Somatic gene theraphy into hematopoietic cells. Current status and future implications," *Clin. Perinatol.* 20(1):155–168, 1993.

Coune, "Liposomes as drug delivery system in the treatment of infectious diseases: potential applications and clinical experience," *Infection* 16(3):141–147, 1988.

Couvreur et al., "Nanocapsules, a new lysosomotropic carrier," *FEBS Lett.*, 84:323–326, 1977.

Couvreur, "Polyalkyleyanoacrylates as colloidal drug carriers," *Crit. Rev. Ther. Drug Carrier Syst.*, 5:1–20, 1988.

Creighton and Goldenberg, "Kinetic Role of a Meta-Stable Native-Like Two-Disulfide Species in the Folding Transition of Bovine Pancreatic Trypsin Inhibitor," *J. Mol. Biol.*, 179:497–526, 1984.

Creighton et al., *J. Mol. Biol.*, 142:43–62, 1980.

Creighton et al., "On the Biosynthesis of Bovine Pancreatic Trypsin Inhibitor (BPTI)," *J. Mol. Biol.*, 232:1176–1196, 1993.

Curiel, D. T., Agarwal, S., Wagner, E., and Cotten, M., "Adenovirus enhancement of transferrin-polylysine-mediated gene delivery," *Proc. Natl. Acad. Sci. USA* 88(19):8850–8854, 1991.

Curiel, D. T., Wagner, E., and Cotten, M., Birnstiel, M. L., Agarwal, S., Li, C.M., Loechel, S., and Hu, P. C. high-efficiency gene transfer mediated by adenovirus coupled to DNA-polylysine complexes," *Hum. Gen. Ther.* 3(2):147–154, 1992.

Dailey and Berg, "Mutants in Disulfide Bond Formation that Disrupt Flagellar Assembly in *Escherichia coli,*" *Proc. Natl. Acad. Sci.* USA, 90:1043–1047, 1993.

Darby et al., "Dissecting the Mechanism of Protein Disulfide Isomerase: Catalysis of Disulfide Bond Formation in a Model Peptide," *Biochemistry*, 33:7937–7947, 1994.

De Sutter et al., *Gene*, 141:163–170, 1994.

De Sutter et al., *Mol. Micro.*, 6:2201–2208, 1992.

Desiderio and Campbell, "Liposome-encapsulated cephalothin in the treatment of experimental murine-salmonellosis," *J. Reticuloendothel. Soc.*, 34:279–287, 1983.

Eglitis, M. A., and Anderson, W. F., "Retroviral vectors for introduction of genes into mammalian cells," *Biotechniques* 6(7):608–614, 1988.

Eglitis, M. A., Kantoff, P. W., Kohn, D. B., Karson, E., Moen, R. C., Lothrop, C. D., Blaese, R. M., and Anderson, W. F., "Retroviral-mediated gene transfer into hemopoietic cells," *Avd. Exp. Med. Biol.* 241:19–27, 1988.

Eichenlaub, R., *J. Bacteriol.*, 138(2):559–566, 1979.

Faller and Baltimore, "Liposome encapsulation of retrovirus allows efficient super infection of resistant cell lines," *J. Virol.*, 49(1):269–272, 1984.

Fersht, "Protein Folding and Stability: the Pathway of Folding of Barnase," *FEBS*, 325:5–16, 1993.

Fiers et al., *Nature*, 273:113, 1978.

Freedman et al., "Protein Disulphide Isomerase: Building Bridges in Protein Folding," *TIBS*, 19:331–336, 1994.

Freedman, *Cell*, 57:1069–1072, 1989.

Fynan, E. F., Webster, R. G., Fuller, D. H., Haynes, J. R., Santoro, J. C., and Robinson, H. L., "DNA vaccines: protective immunizations by parenteral, mucosal, and gene gun inoculations," *Proc. Natl. Acad. Sci. USA* 90(24):11478–11482, 1993.

Gabizon and Papahadjopoulos, "Liposomes formulations with prolonged circulation time in blood and enhanced uptake by tumors," *Proc. Natl. Acad. Sci. USA*, 85:6949–6953, 1988.

Goding, "Monoclonal Antibodies: Principles and Practice," pp. 60–74. 2nd Edition, Academic Press, Orlando, Fla., 1986.

Goeddel et al., *Nature*, 281:544, 1979.

Goeddel et al., *Nucl. Acids Res.*, 8:4057, 1980.

Goldenberg and King, *Proc. Natl. Acad. Sci. USA*, 79:3403–3407, 1982.

Goldenberg, "Kinetic analysis of the folding and unfolding of a mutant form of bovine pancreatic trypsin inhibitor lacking the cysteine-14 and -38 thiols," *Biochemistry*, 27:2481–2489, 1988.

Goldenberg, "Native and Non-Native Intermediates in the BPTI Folding Pathway," TIBS, 17:257–261, 1992.

Graham, F. L., and van der Eb, A. J., "Transformation of rat cells by DNA of human adenovirus 5," Virology 54(2):536–539, 1973.

Green, *Nucl. Acids Res.* 16(1):369. 1988.

Guilhot et al., *Pro. Natl. Acad. Sci. USA*, in press, 1995.

Guzman et al., "Tight regulation, modulation, and high-level expression by vectors containing the arabinose pBAD promoter," *J. Bacteriol.* 177:4121–30, 1995.

Harlow, E. and Lane, D. "Antibodies: A Laboratory Manual," Cold Spring Harbor Laboratory, Cold Spring Harbor, N.Y., 1988.

Heath and Martin, "The development and application of protein-liposome conjugation techniques," *Chem. Phys. Lipids* 40:347–358, 1986.

Heath et al., "Liposome-mediated delivery of pteridine antifolates to cells: in vitro potency of methotrexate and its alpha and gamma substituents," *Biochim. Biophys. Acta*, 862:72–80, 1986.

Henry-Michelland et al., "Attachment of antibiotics to nanoparticles; Preparation, drug-release and antimicrobial activity in vitro, *Int. J. Pharm.*, 35:121–127, 1987.

Hess et al., *J. Adv. Enzyme Reg.*, 7:149, 1968.
Hitzeman et al., *J. Biol. Chem.*, 255:2073, 1980.
Holland et al., *Biochemistry*, 17:4900, 1978.
Hopp, T. P., U.S. Pat. No. 4,554,101, Nov. 19, 1985.
Hultgren et al., "Pilus and Nonpilus Bacterial Adhesins: Assembly and Function in Cell Recognition," *Cell*, 73:887–901, 1993.
Huth et al., "Protein Folding and Assembly In Vitro Parallel Intracellular Folding and Assembly," *J. Biol. Chem.*, 268:16472–16482, 1993.
Hwang et al., "Oxidized Redox State of Glutathione in the Endoplasmic Reticulum," *Science*, 257:1496–1502, 1992.
Imaizumi et al., "Liposome-entrapped superoxide dismutase ameliorates infarct volume in focal cerebral ischemia," *Acta. Neurochirurgica Suppl.*, 51:236–238, 1990b.
Imaizumi et al., "Liposome-entrapped superoxide dismutase reduces cerebral infarction in cerebral ischemia in rats," *Stroke*, 21(9):1312–1317, 1990a.
Itakura et al., *Science*, 198:1056, 1977.
Jacob-Dubuisson et al., "PapD Chaperone Function in Pilus Biogenesis Depends on Oxidant and Chaperone-Like Activities of DsbA," *Proc. Natl. Acad. Sci. USA*, 91:11552–11556, 1994.
Jameson and Wolf, "The Antigenic Index: A Novel Algorithm for Predicting Antigenic Determinants," *Compu. Appl. Biosci.*, 4(1):181–6, 1988.
Jander et al., "Two Cysteines in Each Periplasmic Domain of the Membrane Protein DsbB are Required for its Function in Protein Disulfide Bond Formation," *The EMBO J.*, 13:5121–5127, 1994.
Joly and Swartz, "Protein Folding Activities of *Escherichia coli* Protein Disulfide Isomerase," *Biochemistry*, 33:4231–4236, 1994.
Jones, *Genetics*, 85:12 1977.
Kamitani et al., *EMBO J.*, 11:57–62, 1992.
Kingsman et al., *Gene*, 7:141, 1979.
Kishigami et al., *FEBS Letters*, 364:55–58, 1995.
Kohler and Milstein, *Eur. J. Immunol.* 6:511–519, 1976.
Kohler and Milstein, *Nature* 256:495–497, 1975.
Kuby, J., "Immunology" 2nd Edition. W. H. Freeman & Company, New York, 1994.
Kuszewski et al., "Fast Folding of a Prototypic Polypeptide: The Immunoglobulin Binding Domain of Streptococcal Protein G," *Protein Science*, 3:1945–1952, 1994.
Kyte, J., and Doolittle, R. F., A simple method for displaying the hydropathic character of a protein," *J. Mol. Biol.* 157(1):105–132, 1982.
Liddell, E. J. and Cryer, A. "A Practical Guide to: Monoclonal Antibodies," John Wiley & Sons, New York, 1991.
Lopez-Berestein et al., "Liposomal amphotericin B for the treatment of systemic fungal infections in patients with cancer: a preliminary study" *J. Infect. Dis.*, 2151:704, 1985a.
Lopez-Berestein et al., "Protective effect of liposomal-amphotericin B against C. albicans infection in mice," *Cancer Drug Delivery*, 2:183, 1985b.
Lu, L., Xiao, M., Clapp, D. W., Li, Z. H., and Broxmeyer, H. E., "High efficiency retroviral mediated gene transduction into single isolated immature and replatable CD34(3+) hematopoietic stem/progenitor cells from human umbilical cord blood," *J. Exp. Med.* 178(6):2089–2096, 1993.
Lyles and Gilbert, "Mutations in the Thioredoxin Sites of Protein Disulfide Isomerase Reveal Functional Nonequivalence of the N- and C-terminal Domains," *J. Biol. Chem.*, 269:30946–30952, 1994.
Maloy et al., "Microbial Genetics" 2nd Edition. Jones and Barlett Publishers, Boston, Mass, 1994.
Maloy, S. R., "Experimental Techniques in Bacterial Genetics" Jones and Bartlett Publishers, Boston, MA, 1990.
Maniatis et al., "Molecular Cloning: a Laboratory Manual," Cold Spring Harbor Laboratory, Cold Spring Harbor, N.Y., 1982.
Marks et al., "Production of Native, Correctly Folded Bovine Pancreatic Trypsin Inhibitor by *Escherichia coli*," *J. Biol. Chem.*, 261:7115–7118, 1986.
Martin et al., "Crystal Structure of the DsbA Protein Required for Disulphide Bond Formatin In Vivo, *Nature*, 365:464–468, 1993.
Matsuyama et al., "SecD is Involved in the Release of Translocated Secretory Proteins from the Cytoplasmic Membrane of *Escherichia coli*," *EMBO J.*, 12:265–270, 1993.
Matthews, "Pathways of Protein Folding," *Annu. Rev. Biochem.*, 62:653–683, 1993.
McGrath et al., *J. Biol. Chem.*, 266(10):6620–6625, 1991.
Missiakas et al., *EMBO J.*, 14(14):3415–3424, 1995.
Missiakas et al., "Identification and Characterization of the *Escherichia coli* Gene dsbB, Whose Product is Involved in the Formation of Disulfide Bonds In Vivo," *Proc. Natl. Acad. Sci. USA*, 90:7084–7088, 1993.
Missiakas et al., "The *Escherichia coli* dsbC (xprA) Gene Encodes a Periplasmic Protein Involved in Disulfide Bond Formation," *EMBO J.*, 13:2013–2020, 1994.
Mitraki et al., "Global Suppression of Protein Folding Defects and Inclusion Body Formation," *Science*, 253:54–58, 1991.
Muller et al., "Efficient transfection and expression of heterologous genes in PC12 cells," *DNA Cell Biol.*, 9(3):221–229, 1990.
Nakamura et al., (1987) Enzyme Immunoassays: Heterogeneous and Homogenous Systems, Chapter 27.
Nicolau and Gersonde, "Incorporation of inositol hexaphosphate into intact red blood cells, I. fusion of effector-containing lipid vesicles with erythrocytes," *Naturwissenschaften (Germany)* 66(11):563–566, 1979.
Nilsson et al., "Secretion Incompetence of Bovine Pancreatic Trypsin Inhibitor Expressed in *Escherichia coli*," *J. Biol. Chem.*, 266:2970–2977, 1991.
Nishiyama et al., "Disruption of the Gene Encoding p12 (SecG) Reveals the Direct Involvement and Important Function of SecG in the Protein Translocation of *Escherichia coli* at Low Temperature," *EMBO J.*, 13:3272–3277, 1994.
Novia et al., *J. Biol. Chem.*, 266:19645–19649, 1991.
Ostermeier and Georgiou, *J. Biol. Chem.*, 269:21072–21077, 1994.
Otzen et al., "Structure of the Transition State for the Folding/Unfolding of the Barley Chymotrypsin Inhibitor 2 and Its Implications for Mechanisms of Protein Folding," *Proc. Natl. Acad. Sci. USA*, 91:10422–10425, 1994.
Pikul et al., "In vitro killing of melanoma by liposome-delivered intracellular irradiation, *Arch. Surg.* 122(12):1417–1420, 1987.
Pollitt and Zalkin, *J. Bacteriol.*, 153:27–32, 1983.
Prokop and Bajpai, "Recombinant DNA Technology I" *Ann. N.Y. Acad. Sci.*, Vol. 646, 1991.
Pugsley, "The Complete General Secretory Pathway in Gram-Negative Bacteria," Microbiol. Rev., 57:50–108, 1993.
Puig and Gilbert, "Anti-Chaperone Behavior of BiP During the Protein Disulfide Isomerase-Catalyzed Refolding of Reduced Denatured Lysozyme," *J. Biol. Chem.*, 269:25889–25896, 1994.

Puig and Gilbert, *J. Biol. Chem.*, 269:7746–7771, 1994.

Puig et al., *J. Biol. Chem.*, 269:19128–19135, 1994.

Rawn, J. D. "Biochemistry" Harper & Row Publishers, New York, 1983.

Remington's Pharmaceutical Sciences, 15th Edition, pages 1035–1038 and 1570–1580.

Saiki et al. "Primer-directed enzymatic amplification of DNA with thermostable DNA polymerase," *Science*, 239:487–491, 1988.

Sambrook, J. et al., "Molecular Cloning: A Laboratory Manual," Cold Spring Harbor Laboratory, Cold Spring Harbor, N.Y., 1989.

Sculier et al., "Pilot study of amphotericin B entrapped in sonicated liposomes in cancer patients with fungal infections," *J. Cancer Clin. Oncol.*, 24(3):527–538, 1988.

Segal, I. H., "Biochemical Calculations" 2nd Edition. John Wiley & Sons, New York, 1976.

Shevchik et al., "Characterization of DsbC, a Periplasmic Protein of *Erwinia chrysanthemi* and *Escherichia coli* with Disulfide Isomerase Activity," *EMBO J.*, 13:2007–2012, 1994.

Silhavy et al., *Experiments with Gene Fusions*, Cold Spring Harbor Laboratory, Cold Spring Harbor, N.Y., 1983.

Spoerel, *Methods Enzymol.* 152:588–597, 1987.

Stinchcomb et al., *Nature*, 282:39, 1979.

Tschemper et al., *Gene*, 10:157, 1980. van Mierlo et al., "Partially Folded Conformation of the (30–51) Intermediate in the Disulphide Folding Pathway of Bovine Pancreatic Trypsin Inhibitor," *J. Mol. Biol.*, 229:1125–1146, 1993.

Vincent and Lazdunski, *Biochemistry*, 11:2967–2977, 1972.

Wagner, E., Zatloukal, K., Cotten, M., Kirlappos, H., Mechtler, K., Curiel, D. T., and Birnstiel, M. L., "Coupling of adenovirus to transferrin-polylysine/DNA complexes greatly enhances receptor-mediated gene delivery and expression of transfected genes," *Proc. Natl. Acad. Sci. USA* 89(13):6099–6103, 1992.

Walker and Gilbert, "Effect of Redox Environment on the In Vitro and In Vivo Folding of RTEM-1 β-Lactamase and *E. coli* Alkaline Phosphatase," *Biochemistry* (submitted), 1995.

Weissman and Kim, "Efficient Catalysis of Disulphide Bond Rearrangement by Protein Disulphide Isomerase, *Nature*, 365:185–188, 1993.

Weissman and Kim, "Kinetic Role of Nonnative Species in the Folding of Bovine Pancreatic Trypsin Inhibitor," *Proc. Natl. Acad. Sci. USA*, 89:9900–9904, 1992a.

Weissman and Kim, "Reexamination of the Folding of BPTI: Predominance of Native Intermediates," *Science*, 253:1386–1393, 1991.

Wetzel, "Mutations and Off-Pathway Aggregation of Proteins," *Trends Biotech.*, 12:193–198, 1994.

Wittrup, *Curr. Opin. Biotech.*, in press, 1995.

Wolf et al., "An Integrated Family of Amino Acid Sequence Analysis Programs," *Compu. Appl. Biosci.*, 4(1):187–91, 1988.

Wong, T. E., and Neumann, E., "Electric field mediated gene transfer," *Biochim. Biophys. Res. Commun.* 107(2):584–587, 1982.

Wülfing and Plückthun, "Protein folding in the periplasm of *Escherichia coli*," *Molec. Micro.*, 12:685–692, 1994.

Wunderlich and Glockshuber, "In Vivo Control of Redox Potential During Protein Folding Catalyzed by Bacterial Protein Disulfide-Isomerase (DsbA)," *J. Biol. Chem.*, 268:24547–24550, 1993a.

Wunderlich and Glockshuber, "Redox Properties of Protein Disulfide Isomerase (DsbA) from *Escherichia coli*," *Protein Sci.*, 2:717–726, 1993b.

Wunderlich et al., "Bacterial Protein Disulfide Isomerase: Efficient Catalysis of Oxidative Protein folding at Acidic pH," *Biochemistry*, 32:12251–12256, 1993.

Young and Davis, "Efficient Isolation of Genes by Using Antibody Probes," *Proc. Natl. Acad. Sci. USA*, 80:1194–1198, 1983.

Zapun and Creighton, "Effects of DsbA on the Disulfide Folding of Bovine Pancreatic Trypsin Inhibitor and α-Lactalbumin," *Biochemistry*, 33:5202–5211, 1994.

Zapun et al., *Biochemistry*, 32:5083–5092, 1993.

Zapun et al., "Folding In Vitro of Bovine Pancreatic Trypsin Inhibitor in the Presence of Proteins of the Endoplasmic Reticulum," *Proteins: Struct., Funct., Genet.*, 14:10–15, 1992.

Zapun et al., "Replacement of the Active-Site Cysteine Residues of DsbA, a Protein Required for Disulfide Bond Formation In Vivo," *Biochemistry*, 33:1907–1914, 1994.

Zapun et al., "The Reactive and Destabilizing Disulfide Bond of DsbA, a Protein Required for Protein Disulfide Bond Formation In Vivo," *Biochemistry*, 32:5083–5092, 1993.

Zatloukal, L., Wagner, E., Cottcn, M., Phillips, S., Plank, C., Steinlein, P., Curiel, D. T., and Birnstiel, M. L., "Transferrinfection: a highly efficient way to express gene constructs in eukaryotic cells," *Ann. N.Y. Acad. Sci.* 660:136–153, 1992.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. Accordingly, the exclusive rights sought to be patented are as described in the claims below.

What is claimed is:

1. A process for producing in a bacterial cell, a biologically-active, soluble eukaryotic polypeptide having at least about three disulfide bonds, comprising expressing in said cell a first DNA segment encoding a disulfide isomerase operably linked to a signal sequence and a second DNA segment encoding said eukaryotic polypeptide operably linked to a signal sequence under conditions effective to produce said eukaryotic polypeptide.

2. The process according to claim 1, wherein said signal sequence is selected from the group consisting of OmpA, LamB, StII, MalE, Lpp, and PelB.

3. The process according to claim 1, wherein said first and said second DNA segments are expressed from one or more promoters selected from the group consisting of lac-lpp, lac, ara, lpp, trc, tac, T7, $P_{BAD}$, phoA and $\lambda_{PL}$.

4. The process according to claim 1, wherein said first DNA segment is expressed by pLPPsOmpArPDI, or wherein said second DNA segment is expressed by pTPA177 or pACYCBPTI.

5. The process according to claim 1, wherein said eukaryotic polypeptide is secreted to the periplasm or to the outer membrane of said bacterial cell.

6. The process according to claim 1, wherein said eukaryotic polypeptide is isolatable from a culture supernatant or a soluble fraction of said bacterial cell.

7. The process according to claim 1, wherein said eukaryotic polypeptide produced in said bacterial host cell has the same conformation assumed by said polypeptide when produced in a eukaryotic host cell.

8. The process according to claim 1, wherein said eukaryotic polypeptide is a mammalian polypeptide.

9. The process according to claim 8, wherein said mammalian polypeptide is a human or bovine polypeptide.

10. The process according to claim 9, wherein said mammalian polypeptide is a tissue plasminogen activator or pancreatic trypsin inhibitor.

11. The process according to claim 1, wherein said disulfide isomerase is protein disulfide isomerase.

12. The process according to claim 11, wherein said protein disulfide isomerase is a rat, yeast, or human protein disulfide isomerase.

13. The process according to claim 1, wherein said eukaryotic polypeptide comprises at least seven disulfide bonds.

14. The process according to claim 13, wherein said eukaryotic polypeptide comprises at least twelve disulfide bonds.

15. The process according to claim 14, wherein said eukaryotic polypeptide comprises at least fourteen disulfide bonds.

16. The process according to claim 15, wherein said eukaryotic polypeptide comprises at least seventeen disulfide bonds.

17. The process according to claim 16, wherein said eukaryotic polypeptide comprises seventeen disulfide bonds.

18. The process according to claim 1, wherein said bacterial cell is an Escherichia coli or Salmonella spp. cell.

19. The process according to claim 18, wherein said bacterial cell is cultured in a medium comprising one or more reducing agents selected from the group consisting of glutathione, cysteine, cystamine, thioglycollate, dithioerythritol, dithiothreitol and dithioerythritol.

20. The process according to claim 18, wherein said Escherichia coli cell is selected from the group consisting of ATCC 98380, SF103, SF110, UT5600 and RB791.

21. The process according to claim 1, wherein said eukaryotic polypeptide produced in said bacterial cell has a specific activity equal to or greater than the specific activity of said polypeptide when produced in a eukaryotic host cell.

22. The process according to claim 21, wherein said eukaryotic polypeptide is a tissue plasminogen activator protein or a pancreatic trypsin inhibitor protein having a specific activity of at least about 1 to about 30 $\mu$g/L/OD$_{600\ nm}$ of culture.

23. An expression system for producing in a bacterial cell, a biologically-active, soluble eukaryotic polypeptide, said system comprising a first DNA segment and a second DNA segment, wherein said first segment encodes a disulfide isomerase and said second segment encodes a eukaryotic polypeptide having at least about three disulfide bonds.

24. The expression system according to claim 23, wherein said first DNA segment is expressed by pLPPsOmpArPDI or wherein said second DNA segment is expressed by pTPA177 or pACYCBPTI.

25. The expression system according to claim 23, wherein said E. coli cell is selected from the group consisting of ATCC 98380, SF103, SF110, UT5600 and RB791.

26. The expression system according to claim 23, wherein said eukaryotic polypeptide is a mammalian polypeptide.

27. The expression system according to claim 26, wherein said mammalian polypeptide is a human or bovine polypeptide.

28. The expression system according to claim 27, wherein said mammalian polypeptide is a tissue plasminogen activator or pancreatic trypsin inhibitor.

29. The expression system according to claim 23, wherein said disulfide isomerase is protein disulfide isomerase.

30. The expression system according to claim 29, wherein said protein disulfide isomerase is selected from the group consisting of rat, yeast, and human protein disulfide isomerase.

31. The expression system according to claim 23, wherein said first DNA segment or said second DNA segment further comprises a signal sequence selected from the group consisting of OmpA, LamB, StII, MalE, Lpp, and PelB.

32. The expression system according to claim 31, wherein said signal sequence is an OmpA signal sequence.

33. The expression system according to claim 23, wherein said first DNA segment or said second DNA segment is expressed from one or more promoters selected from the group consisting of lac-lpp, lac, ara, lpp, trc, tac, T7, $P_{BAD}$, phoA and $\lambda_{PL}$.

34. The expression system according to claim 33, wherein said first DNA segment or said second DNA segment is expressed from a lac-lpp promoter.

35. A recombinant vector comprising a first transcriptional unit encoding a mammalian protein disulfide isomerase operably linked to a first signal sequence and said second transcriptional unit comprises a DNA segment encoding a mammalian polypeptide having at least about three disulfide bonds operably linked to a second signal sequence.

36. The recombinant vector according to claim 35, wherein said mammalian polypeptide is a human or bovine polypeptide.

37. The recombinant vector according to claim 35, wherein said mammalian polypeptide is a tissue plasminogen activator or pancreatic trypsin inhibitor.

38. The recombinant vector according to claim 35, wherein said protein disulfide isomerase is a rat, yeast, or human protein disulfide isomerase.

39. A prokaryotic cell transformed with the vector according to claim 35.

40. The cell of claim 39, further defined as *E. coli* ATCC 98380.

* * * * *

SEQUENCE LISTING

<160> NUMBER OF SEQ ID NOS: 2

<210> SEQ ID NO 1
<211> LENGTH: 39
<212> TYPE: DNA

-continued

```
<213> ORGANISM: Artificial Sequence
<220> FEATURE:
<223> OTHER INFORMATION: Description of Artificial Sequence:  Synthetic
      Primer

<400> SEQUENCE: 1
atatgaattc tggttttcgc ccaacaagaa gctgtggcc                             39

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
ggacggagga tccttacaat tcatggtg                                         28
```